US009046527B2

(12) United States Patent
Galisson et al.

(10) Patent No.: US 9,046,527 B2
(45) Date of Patent: Jun. 2, 2015

(54) MUTATED SUMO ISOFORMS AND USES THEREOF

(75) Inventors: Frédéric Galisson, Lyons (FR); Louiza Mahrouche, Montreal (CA); Eric Bonneil, Montreal (CA); Mounira Chelbi-Alix, Paris (FR); Sylvain Meloche, Montreal (CA); Pierre Thibault, Ile Bizard (CA)

(73) Assignee: Université De Montréal, Montreal (CA)

( * ) Notice: Subject to any disclaimer, the term of this patent is extended or adjusted under 35 U.S.C. 154(b) by 0 days.

(21) Appl. No.: 13/349,459

(22) Filed: Jan. 12, 2012

(65) Prior Publication Data

US 2012/0276529 A1 Nov. 1, 2012

Related U.S. Application Data

(63) Continuation of application No. PCT/CA2010/001100, filed on Jul. 13, 2010.

(60) Provisional application No. 61/225,072, filed on Jul. 13, 2009.

(51) Int. Cl.

| C07K 16/18 | (2006.01) |
|---|---|
| C07K 1/22 | (2006.01) |
| C12P 21/08 | (2006.01) |
| C07K 5/103 | (2006.01) |
| G01N 33/53 | (2006.01) |
| G01N 30/72 | (2006.01) |
| G01N 33/68 | (2006.01) |
| C07K 14/47 | (2006.01) |
| C12Q 1/25 | (2006.01) |
| C12Q 1/37 | (2006.01) |
| G01N 33/50 | (2006.01) |

(52) U.S. Cl.
CPC ............ G01N 33/6848 (2013.01); C07K 14/47 (2013.01); C07K 16/18 (2013.01); C12Q 1/25 (2013.01); C12Q 1/37 (2013.01); G01N 33/5008 (2013.01); G01N 33/6842 (2013.01); G01N 2333/9015 (2013.01); G01N 2440/00 (2013.01)

(58) Field of Classification Search
CPC ........ C07K 16/44; C07K 14/47; C07K 16/18; G01N 2440/36; G01N 2333/9015; G01N 33/6842; G01N 33/6848; C12Q 1/25; C12Q 1/37

See application file for complete search history.

(56) References Cited

U.S. PATENT DOCUMENTS 6,015,662 A * 1/2000 Hackett et al. .................... 435/5

FOREIGN PATENT DOCUMENTS

| WO | 01/75067 A2 | 10/2001 |
| WO | WO2004063214 | * 7/2004 |
| WO | 2006/073976 A2 | 7/2006 |

OTHER PUBLICATIONS

Witte et al., Cancer and Metastasis Reviews 17: 155-161, 1998.*
Matunis et al., J Cell Biology 135: 1457-1470, 1996.*
Hong et al., J Biol Chem 276(43): 40263-40267, 2001.*
Pichler et al., Nature Structural & Molecular Biology 12(3): 264-269; Mar. 2005.*
Knuese et al., Molecular & Cellular Proteomics 4: 1626-1636, 2005.*
Yu et al., Investigative Ophthalmology & Visual Science 49(2): 522-527, Feb. 2008.*
Bossis et al., SUMO: regulating the regulator, Cell division 1:13, pp. 1-8, 2006.
Geiss-Friedlander et al., "Concepts in sumoylation: a decade on," Nat. Rev. Mol. Cell Biol., 8, pp. 947-956, 2007.
Guo et al., "A funtional variant of SUMO4, a new IκBα modifier, is associated with type 1 diabetes," Nature Genetics, 36(8): 837-841, 2004.
Guo et al., "Signalling pathways and the regulation of SUMO modification," Biochemical Society Transations 35, part 6, pp. 1414-1418, 2007.
Hay R.T., "SUMO: a history of modification," Molecular Cell 18, pp. 1-12, 2005.
Jaffray et al., "Detection of modification by ubiquitin-like proteins," Methods, 38, pp. 35-38, 2006.
Joseph et al., "SUMO-1 targets RanGAP1 to kinetochores and mitotic spindles," The Journal of cell biology 156 (4):595-602, 2002.
Kim et al., "SUMOylotaion code in cancer development and metastasis," Molecules and cells 22(3):247-253, 2006.
Knuesel et al., "A method of mapping protein sumoylation sites by mass spectrometry using a modified small ubiquitin-like modifier (SUMO-1) and a computational program," Molecular and Cellular Proteomics, vol. 4 (10):1626-1636, 2005.
Owerbach et al., "A proline-90 residue unique to SUMO-4 prevents maturation and sumoylation," Biochem Biophys Res Commun 337, pp. 517-520, 2005.
Pedrioli et al., "Automated identification of SUMOylation sites using mass spectrometry and SUMmOm pattern recognition software," Nature Methods 3(7):533-539, 2006.
Rodriguez et al., "SUMO-1 conjugation in vivo requires both a consensus modification motif and nuclear targeting," J. Biol. Chem., 276(16):12654-12659, 2001.
Swaminathan et al., "RanGAP1*SUMO1 is phosphorylated at the onset of mitosis and remains associated with RanBP2 upon NPC disassembly," The Journal of Cell Biology, 164(7):965-971, 2004.
Vertegaal et al., "Distinct and overlapping sets of SUMO-1 and SUMO-2 target proteins revealed by quantitative proteomics," Mol Cell Proteomics 5.12, pp. 2298-2310, 2006.
Weisshaar et al., "Arsenic trioxide stimulates SUMO-2/3 modification leading to RNF4-dependent proteolytic targeting of PML," FEBS Letters 582, pp. 3174-3178, 2008.

(Continued)

Primary Examiner — Phuong Huynh
(74) Attorney, Agent, or Firm — Darlene A. Vanstone, Esq.; Carolyn S. Elmore, Esq.; Elmore Patent Law Group, P.C.

(57) ABSTRACT

Disclosed herein are substantially pure nucleic acids encoding mutated SUMO isoforms, polypeptides, vectors, cells and methods of their use to identify and quantify protein SUMOylation in mammalian cells. Also disclosed is a dual affinity method for detecting a mutated SUMOylated protein substrate fragment.

18 Claims, 39 Drawing Sheets

(56) References Cited

OTHER PUBLICATIONS

Zhang, SUMO-1 Function is Dispensable in Normal Mouse Development, Molecular and Cellular Biology, 28 (17):5381-5390, 2008.
Evdokimov et al., "Loss of SUMO1 in Mice Affects RanGAP1 Localization and Formation of PML Nuclear Bodies, but is not Lethal as it can be Compensated by SUMO2 or SUMO3," Journal of Cell Science, 121(24):4106-4113, 2008.
Pichler, et al., "SUMO Modification of the Ubiquitin-Conjugating Enzyme E2-25K," Nature Structural and Molecular Biology, 12(3):264-9, 2005.
Blomster, et al., "In Vivo Identification of Sumoylation Sites by a Signature Tag and Cysteine-targeted Affinity Purification," Journal of Biological Chemistry, 285(25):19324-19329, 2010.

* cited by examiner

SUMO4 WT cDNA sequence

```
  1 M  A  N  E  K  P  T  E  E  V  K  T  E  N  N  N  H  I  N  L
  1 ATG GCC AAC GAA AAG CCT ACA GAA GAA GTC AAG ACT GAG AAC AAC AAT CAT ATT AAT TTG

21 K  V  A  G  Q  D  G  S  V  V  Q  F  K  I  K  R  Q  T  P  L
 61 AAG GTG GCA GGA CAG GAT GGT TCT GTG GTG CAG TTT AAG ATT AAG AGG CAG ACA CCA CTT

41 S  K  L  M  K  A  Y  C  E  P  R  G  L  S  V  K  Q  I  R  F
121 AGT AAA CTA ATG AAA GCT TAT TGT GAA CCA CGG GGA TTG TCA GTG AAG CAG ATC AGA TTC

61 R  F  G  G  Q  P  I  S  G  T  D  K  P  A  Q  L  E  M  E  D
181 CGA TTT GGT GGG CAA CCA ATC AGT GGA ACA GAC AAA CCT GCA CAG TTG GAA ATG GAA GAT

81 E  D  T  I  D  V  F  Q  Q  P  T  G  G  V  Y  *  N  A  N  E
241 GAA GAT ACA ATT GAT GTG TTT CAA CAG CCT ACG GGA GGT GTC TAC TGA ATG GCC AAC GAA

101 K  P  T  E  E  V  K  T  E  N  N  N  H  I  N  L  K  V  A  G
301 AAG CCT ACA GAA GAA GTC AAG ACT GAG AAC AAC AAT CAT ATT AAT TTG AAG GTG GCA GGA

121 Q  D  G  S  V  V  Q  F  K  I  K  R  Q  T  P  L  S  K  L  M
361 CAG GAT GGT TCT GTG GTG CAG TTT AAG ATT AAG AGG CAG ACA CCA CTT AGT AAA CTA ATG

141 K  A  Y  C  E  P  R  G  L  S  V  K  Q  I  R  F  R  F  G  G
421 AAA GCT TAT TGT GAA CCA CGG GGA TTG TCA GTG AAG CAG ATC AGA TTC CGA TTT GGT GGG

161 Q  P  I  S  G  T  D  K  P  A  Q  L  E  M  E  D  E  D  T  I
481 CAA CCA ATC AGT GGA ACA GAC AAA CCT GCA CAG TTG GAA ATG GAA GAT GAA GAT ACA ATT

181 D  V  F  Q  Q  P  T  G  G  V  Y  *              (SEQ ID NO. 13)
541 GAT GTG TTT CAA CAG CCT ACG GGA GGT GTC TAC TGA  (SEQ ID NO. 14)
```

FIG. 2D

UBI    N-ter...GIPPDQQRLIFAGKQLEDGRTLSDYNIQKESTLHLVLRLRGG (SEQ ID NO. 22)

SUMO1  N-ter...GVPMNSLRFLFEGQRIADNHTPKELGMEEEDVIEVYQEQTGG (SEQ ID NO. 23)
SUMO2  N-ter...  GLSMRQIRFRFDGQPINETDTPAQLEMEDEDTIDVFQQQTGG (SEQ ID NO. 24)
SUMO3  N-ter...  GLSMRQIRFRFDGQPINETDTPAQLEMEDEDTIDVFQQQTGG (SEQ ID NO. 25)

→

........IEVYREQTGG (SEQ ID NO. 26)
                                          ........IEVYQRQTGG (SEQ ID NO. 27)
                                          ........IEVYQERTGG (SEQ ID NO. 28)
                                          ........IDVFRQQTGG (SEQ ID NO. 29)
                                          ........IDVFRNQTGG (SEQ ID NO. 30)

⇧ SUMO1 mutant Q92R
⇧ SUMO1 mutant E93R
⇧ SUMO1 mutant Q94R
⇧ SUMO2 mutant Q88R
⇧ SUMO3 mutant Q87R, Q88N

FIG. 2E

| E2-25K | EFKEVLK |
| SUMO1-Q92R | EQTGG |

| E2-25K | EFKEVLK |
| SUMO2-Q92R | QQTGG |

| E2-25K | EFKEVLK |
| SUMO3-Q92R, Q93N | NQTGG |

FIG. 12A

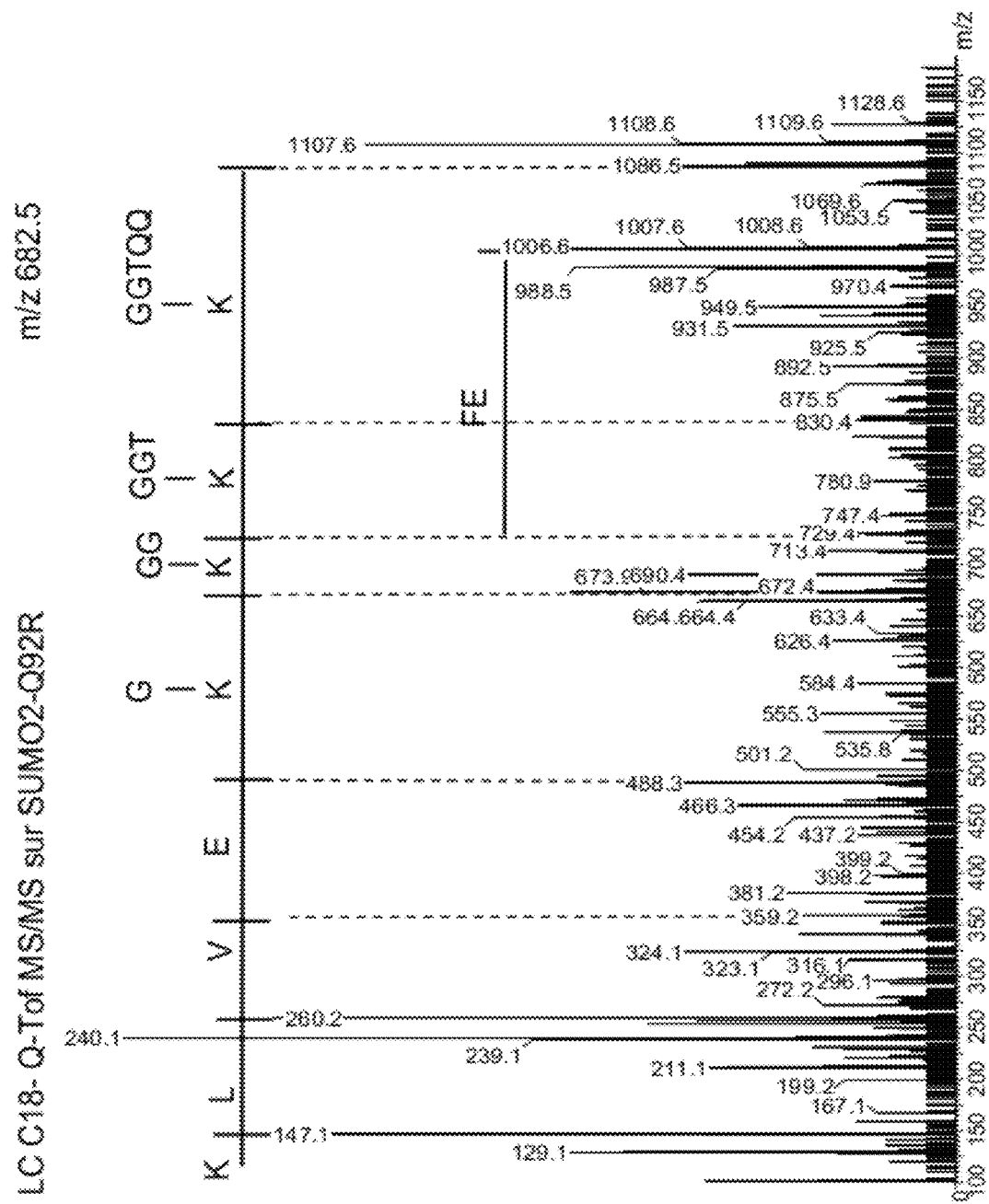

| Protein | Site | Enzyme | Function |
|---|---|---|---|
| Histone 3.2 (nuclear) | K23 | Unknown* | Nucleosome assembly |
| HSF4B (nuclear) | K288 | Unknown* | DNA-binding protein; Binds HSE; Isoform α ↓ transcription, β ↑ transcription |
| Lamin A/C (nucleus) | K420 | Unknown | Nuclear lamina |
| PML | K380, K400, K490 | Unknown/known | Probable transcription factor |
| RBM3 Protein | K1094 | Unknown | RNA binding protein |
| RSF1 (nucleus) | K327 | Unknown | Assembly of regular nucleosome by the RSF chromatin-remodeling complex |
| SAFB2 (nucleus) | K524 | Unknown | Binds to scaffold/matrix attachment region DNA. Can also inhibit cell proliferation |
| SUMO3 | K11 | Known | Cross-link |
| TRIM28 (nucleus) | K750, K779 | Known | Forms a complex with a KRAB-domain TF and ↑ KRAB-mediated repression |
| WIZ1 (nucleus) | K1323 | Unknown | May link EHMT1 and EHMT2 to the CTBP corepressor machinery |
| Ubiquitin | K11 | Unknown* | Cross-link |
| SUMO2 | K42 | Known | Cross-link |

* Known to be sumoylated but not the site

FIG. 23

| protein | Sumo site | Before IP | After IP |
|---------|-----------|-----------|----------|
| H2B     | K20       | yes       | no       |
|         | K34       | no        | yes      |
|         | K11       | no        | yes      |
|         | K116      | no        | yes      |
|         | K108      | no        | yes      |
| H2A     | K36       | no        | yes      |
| H3.1    | K9        | no        | yes      |
|         | K36       | no        | yes      |
|         | K23       | no        | yes      |
| H4      | K8        | no        | yes      |
|         | K20       | no        | yes      |

FIG. 26

MUTATED SUMO ISOFORMS AND USES THEREOF

RELATED APPLICATION(S)

This application is a continuation of International Application No. PCT/CA2010/001100, which designated the United States and was filed on Jul. 13, 2010, published in English, which claims the benefit of U.S. Provisional Application No. 61/225,072, filed on Jul. 13, 2009.

The entire teachings of the above application(s) are incorporated herein by reference.

SEQUENCE LISTING

The instant application contains a Sequence Listing which has been submitted electronically in ASCII format and is hereby incorporated by reference in its entirety. Said ASCII copy, created on Nov. 22, 2013, is named 4089.3001US_SL.txt and is 26,318 bytes in size.

TECHNICAL FIELD

The present concerns mutated SUMO isoforms, and more particularly to their use to identify and quantify protein SUMOylation in mammalian cells.

BACKGROUND

Small Ubiquitin-like Modifier (SUMO) proteins are a family of proteins which are structurally similar to ubiquitin. In lower eukaryotes a single SUMO gene is expressed (Smt3 in *Saccharomyces cerevisiae*), whereas in vertebrates three paralogs designated SUMO1, SUMO2 and SUMO3 are ubiquitously expressed in all tissues. The human genome also encodes a forth gene for SUMO4 that appears to be uniquely expressed in the spleen, lymph nodes and kidney (Guo, D. et al. A functional variant of SUMO4, a new I kappa B alpha modifier, is associated with type 1 diabetes. *Nat Genet* 36, 837-841 (2004)), though its in vivo maturation into a conjugation-competent form still remains unclear (Owerbach, D., McKay, E. M., Yeh, E. T., Gabbay, K. H. & Bohren, K. M. A proline-90 residue unique to SUMO-4 prevents maturation and sumoylation. Biochem Biophys Res Commun 337, 517-520 (2005)). Protein SUMOylation is the post-translational covalent but reversible conjugation of SUMO (SUMO-1, 2 and 3 isoforms in mammalian cells) to protein substrates. This covalent modification is obtained by the formation of an isopeptide bond between the ε-amino group of a lysine residue from the protein substrate and the C-terminus COOH group of the SUMO isoform. This modification is structurally similar to ubiquitin although it shares less than 20% amino acid sequence homology.

Protein SUMOylation is an essential cellular process conserved from yeast to mammals. It is involved in different processes including the regulation of intracellular trafficking, cell cycle, DNA repair and replication, RNA metabolism, cell signaling and stress responses (Bossis, G., and Melchior, F. (2006). SUMO: regulating the regulator. Cell division 1, 13; Hay, R. T. (2005). SUMO: a history of modification. Molecular cell 18, 1-12).

Protein SUMOylation imparts significant structural and conformational changes on the substrate protein by masking and or by conferring additional scaffolding surfaces for protein interactions.

At present, several hundred protein substrates are known to be SUMOylated. These protein targets include regulators of gene expression (e.g. transcription factors, co-activators or repressors) as well as oncogenes and tumor suppressor genes, such as promyelocytic leukaemia (PML), Mdm2, c-Myb, c-Jun, and p53 whose misregulation leads to tumorigenesis and metastasis (Kim, K. I., and Baek, S. H. (2006). SUMOylation code in cancer development and metastasis. Molecules and cells 22, 247-253).

Protein SUMOylation is a highly dynamic modification regulated by a complex network of SUMO-activating enzymes (SAE1/SAE2), conjugating enzymes (Ubc9) and SUMO-E3 ligases (PIAS1, PIAS3, PIASxα, PIASxβ, PIASy, RanBP2 and Pc2) for the transfer of SUMO isoforms to specific protein substrates (Kim, K. I., and Baek, S. H. (2006). SUMOylation code in cancer development and metastasis. Molecules and cells 22, 247-253; Guo, B., Yang, S. H., Witty, J., and Sharrocks, A. D. (2007). Signalling pathways and the regulation of SUMO modification. Biochemical Society transactions 35, 1414-1418). The dynamic changes in protein SUMOylation in response to different cell stimuli is counterbalanced by SUMO-specific proteases (SUSP's or SENPs) which cleave this modification on specific SUMO substrates (see FIG. 1).

Currently, the extent and biological significance of protein SUMOylation in cell regulation and cancer development, remains poorly understood. No efficient methods exist for the comprehensive quantitation and analysis of this modification from cell extracts. The relatively low stoichiometry of protein SUMOylation is a significant analytical challenge for its identification and quantitation in intact cells. Recent reports have described the successful identification of SUMO protein candidates by transfecting $His_6$-SUMO1 and $His_6$-SUMO-2, and quantifying their proportions using mass spectrometry (MS) and metabolic labelling in cell cultures (Vertegaal, A. C., Andersen, J. S., Ogg, S. C., Hay, R. T., Mann, M., and Lamond, A. I. (2006). Distinct and overlapping sets of SUMO-1 and SUMO-2 target proteins revealed by quantitative proteomics. Mol Cell Proteomics 5, 2298-2310).

However, the identification of SUMOylation sites by MS remains challenging due to their low occurrence and the presence of long SUMO C-termini polypeptides which lack Arg/Lys. This complicates the MS/MS assignment of the corresponding tryptic peptides (Pedrioli, P. G., Raught, B., Zhang, X. D., Rogers, R., Aitchison, J., Matunis, M., and Aebersold, R. (2006). Automated identification of SUMOylation sites using mass spectrometry and SUMmOn pattern recognition software. Nature methods 3, 533-539).

Furthermore, the lack of efficient tools and methods to identify protein SUMOylation also complicates the identification of enzymes responsible for this modification and of substrates upon which they act. Thus, there is a need for new methods to identify protein SUMOylation sites.

BRIEF SUMMARY

The present discovery addresses the shortcomings of the current methods.

In one aspect, there is provided a substantially pure nucleic acid encoding a mutated SUMO polypeptide.

In one example, the SUMO polypeptide comprises a SUMOylation site. The nucleic acid is mammalian. The mammal is a human. The nucleic acid is DNA which includes a SUMO gene. The DNA is genomic DNA or cDNA. In another example, the mutated SUMO polypeptide is mutated SUMO-1, mutated SUMO-2, or mutated SUMO-3.

In another aspect, there is provided a substantially pure nucleic acid having the sequence of SEQ ID NO: 3 and encoding the amino acid sequence of SEQ ID NO: 4.

In another aspect, there is provided a substantially pure nucleic acid having the sequence of SEQ ID NO: 7 and encoding the amino acid sequence of SEQ ID NO: 8.

In another aspect, there is provided a substantially pure nucleic acid having the sequence of SEQ ID NO: 11 and encoding the amino acid sequence of SEQ ID NO: 12.

In another aspect, there is provided a substantially pure nucleic acid having about 50% or greater nucleotide sequence identity to the sequence of SEQ ID NO: 3, SEQ ID NO: 7 or SEQ ID NO: 11.

In one example there is DNA which is operably linked to regulatory sequences for expression of the polypeptide and wherein the regulatory sequences comprise a promoter. The nucleic acid included the promoter is a constitutive promoter, is inducible by one or more external agents, or is cell-type specific.

In another aspect, there is provided a vector comprising the nucleic acid, as described above, the vector being capable of directing expression of the polypeptide encoded by the nucleic acid in a vector-containing cell.

In another aspect, there is provided a cell that contains the nucleic acid, as described above.

In another aspect, there is provided a transgenic cell that contains the nucleic acid, as described above, wherein the nucleic acid is expressed in the transgenic cell.

In another aspect, there is provided a transgenic non-human mammal generated from the cell, as described above, wherein the nucleic acid is expressed in the transgenic mammal.

In one aspect, there is provided a cell in vitro expressing a recombinant nucleic acid comprising a nucleic acid sequence encoding a mutated SUMO polypeptide.

In another aspect, there is provided a transgenic non-human mammal model for studying abnormal SUMOylation, wherein the mammal comprises a mutated SUMO polypeptide.

In one aspect, there is provided a method of producing a mutated SUMO polypeptide, the method comprising:
a) providing a cell transfected with a nucleic acid sequence encoding a mutated SUMO polypeptide positioned for expression in the cell;
b) culturing said transfected cells under conditions for expressing the nucleic acid; and
c) producing the mutated SUMO polypeptide.

In another aspect, there is provided a substantially pure mammalian mutated SUMO polypeptide, or fragment thereof.

In one example, the polypeptide is encoded by the nucleic acid sequence of SEQ ID NO: 3, SEQ ID NO: 7 or SEQ ID NO: 11. The polypeptide comprising an amino acid sequence substantially identical to an amino acid sequence of SEQ ID NO: 4, SEQ ID NO: 8 or SEQ ID NO: 12.

The polypeptide is a mammalian polypeptide. The polypeptide is a human polypeptide. The polypeptide is mutated SUMO-1, 2 or 3.

In one aspect, there is provided a method for the large-scale identification of protein SUMOylation sites, the method comprising:
proteolytically digesting a mutated SUMOylated protein substrate to release a fragment of the mutated SUMOylated protein substrate; and
identifying the fragment using mass spectral analysis.

In one example, the mutated SUMIOylated protein substrate includes E2-25 k ligase, RanGAP, or PML.

In another example, the fragments of the mutated SUMOylated protein substrate include:

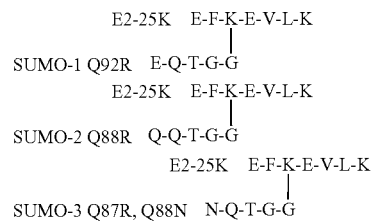

where the line between the K residue and the G residue is a covalent bond.

In one example, the fragments are identified using tandem mass spectrometry) with collisional activation and/or electron transfer dissociation. Trypsin is used to proteolytically digest the mutated SUMOylated protein substrate.

In one aspect, there is provided a method of monitoring changes in protein SUMOylation in response to chemical or environmental stimulation, the method comprising:
expressing a mutated SUMO polypeptide;
incubating the mutated polypeptide with a SUMO protein substrate in the presence of chemical or environmental stimulators to produce a mutated SUMOylated protein substrate;
proteolytically digesting the mutated SUMOylated protein substrate to release a fragment of the mutated SUMOylated protein substrate; and
measuring the abundance variation of the fragments so as to monitor the changes in protein SUMOylation in response to the chemical or environmental stimulators.

In another aspect, there is provided a dual affinity method for detecting a mutated SUMOylated protein substrate fragment, the method comprising:
expressing a mutated SUMO polypeptide;
incubating the mutated polypeptide with a SUMO protein substrate in the presence of chemical or environmental stimulators to produce a mutated SUMOylated protein substrate;
proteolytically digesting the mutated SUMOylated protein substrate to release a fragment of the mutated SUMOylated protein substrate;
purifying the fragment using an immunoaffinity reagent; and
detecting the purified fragment.

In one example, the mutated SUMO polypeptide is mutated SUMO-1, mutated SUMO-2, or mutated SUMO-3. The immunoaffinity reagent is a purified antibody which specifically binds to a mutated SUMOylated protein substrate fragment The fragment is purified using immobilized metal affinity chromatography. The fragment is detected using LC-MS.

In one aspect, there is provided a method of identifying biological agents or small molecules that modulate the SUMOylation activity in a cell, the method comprising:
expressing a mutated SUMO polypeptide;
incubating the mutated polypeptide with a SUMO protein substrate in the presence of the a biological agent or a small molecule to produce a mutated SUMOylated protein substrate;
enriching the mutated SUMOylated protein substrate;
proteolytically digesting the mutated SUMOylated protein substrate to release a fragment of the mutated SUMOylated protein substrate;
enriching the fragment of the mutated SUMOylated protein substrate; and profiling the fragment of the mutated SUMOylated protein substrate to determine whether the biological agent or a small molecule modulate the SUMOylation activity in the cell.

In another aspect, there is provided a method of monitoring disease or misregulation progression, the method comprising:

expressing a mutated SUMO polypeptide;

incubating the mutated polypeptide with a SUMO protein substrate in the presence of a potential therapeutic agent to produce a mutated SUMOylated protein substrate;

enriching the mutated SUMOylated protein substrate;

proteolytically digesting the mutated SUMOylated protein substrate to release a fragment of the mutated SUMOylated protein substrate;

enriching the fragment of the mutated SUMOylated protein substrate; and profiling the fragment of the mutated SUMOylated protein substrate to determine whether the potential thereapeutic agent has an effect on the disease or misregulation progression.

In another aspect, there is provided a method for identification of inhibitors, activators or modulators of SUMO E2 conjugating enzymes, SUMO E3 ligases or SUMO proteases, the method comprising:

expressing a mutated SUMO polypeptide;

incubating the mutated polypeptide with a SUMO protein substrate in the presence of the inhibitors, activators or modulators of SUMO E2 conjugating enzymes, SUMO E3 ligases or SUMO proteases to produce a mutated SUMOylated protein substrate;

enriching the mutated SUMOylated protein substrate;

proteolytically digesting the mutated SUMOylated protein substrate to release a fragment of the mutated SUMOylated protein substrate;

enriching the fragment of the mutated SUMOylated protein substrate; and profiling the fragment of the mutated SUMOylated protein substrate to identify inhibitors, activators or modulators of SUMO E2 conjugating enzymes, SUMO E3 ligases or SUMO proteases.

In one example, the mutated SUMOylated protein substrate, as described above, is enriched using affinity purification. The affinity purification is carried out using an NTA column. The fragment of the mutated SUMOylated protein substrate is enriched using an antibody that specially binds to the SUMO pentapeptide in the fragment.

In one aspect, there is provided a mutated SUMOylated protein substrate fragment.

In one example, the SUMOylated protein substrate fragment includes amino acid residues specific to each mutated SUMO isoform. The mutated SUMO isoform is mutated SUMO-1, mutated SUMO-2 or mutated SUMO-3. The SUMOylated protein substrate fragment includes amino acid residues specific to E2-25 k ligase, RanGAP, and PML. The fragment includes those described above.

In one aspect, there is provided a purified antibody which specifically binds to a mammalian mutated SUMO polypeptide.

In one example, the mammal is a human. The mammal is a mouse. The mutated SUMO polypeptide has a sequence of SEQ ID NO: 4, SEQ ID NO: 8 or SEQ ID NO: 12. The antibody is a polyclonal antibody. The antibody is a monoclonal antibody.

In another aspect, there is provided a kit for testing a mammal for the presence a condition or an increased likelihood of developing a condition characterized by impaired regulation of protein SUMOylation or by impaired protein SUMOylation, the kit comprising a substantially pure antibody that specifically binds to a mammalian mutated SUMO polypeptide.

In one example, the kit further comprising a means for detecting the binding of the antibody to the mammalian SUMO polypeptide.

The mammal is a human. The mammal is a mouse. The mutated SUMO polypeptide is mutated SUMO-1, mutated SUMO-2, or mutated SUMO-3. The antibody is a polyclonal antibody. The antibody is a monoclonal antibody.

In another aspect, there is provided a purified antibody which specifically binds to a mutated SUMOylated protein substrate fragment.

In one example, the mutated SUMOylated protein substrate fragment include those described above.

In another aspect, there is provided a solid support for identifying a SUMO mutation in a subject or a biological sample derived from the subject, the solid support comprises a probe for identifying a nucleic acid molecule, as described above.

In another aspect, there is provided a nucleic acid probe for the specific identification of a SUMO mutation in a subject.

In one example, the nucleic acid probe comprises a sequence annealing with or specifically hybridizing to a nucleic acid molecule, as described above.

In another aspect, there is provided a method of detecting in a subject the susceptibility to develop a condition or an increased likelihood of developing a condition characterized by impaired regulation of protein SUMOylation or by impaired protein SUMOylation, the method comprising:

obtaining from said subject a biological sample having DNA;

sequencing predetermined regions of said DNA encoding a SUMO polypeptide; and comparing the sequence obtained at (b) with a corresponding sequence from a non-susceptible control subject for identifying a SUMO mutation known to be indicative of the susceptibility.

In another aspect, there is provided a kit for detecting the presence or absence of a mutant SUMO nucleic acid molecule in a biological sample, the kit comprising: a user manual or instructions and (i) a solid support for identifying a mutant SUMO nucleic in the biological sample, the solid support comprises a probe for identifying the nucleic acid molecule, as described above.

In another aspect, there is provided a method is provided for differentiating between mutant SUMO isoforms, the method comprising:

providing a mutant strain expressing mutated SUMO-1, SUMO-2 and SUMO-3 polypeptides;

incubating mutated the SUMO polypeptides with SUMO protein substrates to produce a SUMOylated protein substrates;

enriching the SUMOylated protein substrates with affinity chromatography;

digesting the SUMOylated protein substrates with trypsin to provide SUMOylated tryptic fragments;

enriching the SUMOylated fragments with antibody that specifically binds to SUMOylated moiety; and identifying by mass spectrometry the SUMOylation sites and the type of SUMO isoform attached to the modified lysine residue.

BRIEF DESCRIPTION OF THE DRAWINGS

In order that the present discovery may be readily understood, embodiments are illustrated by way of example in the accompanying drawings.

FIG. 2A illustrates nucleotide and amino acid sequences of human His6-SUMO1 wild-type (SEQ ID NO's: 1 and 2) and the Q92R mutant (SEQ ID NO's: 3 and 4).

FIG. 2B illustrates nucleotide and amino acid sequences of human His6-SUMO2 wild-type (SEQ ID NO's: 5 and 6) and the Q88R mutant (SEQ ID NO's: 7 and 8).

FIG. 2C illustrates nucleotide and amino acid sequences of human His6-SUMO3 wild-type (SEQ ID NO's: 9 and 10) and the Q87R, Q88N mutant (SEQ ID NO's: 11 and 12).

FIG. 2D illustrates nucleotide and amino acid sequences of human SUMO4 wild-type (SEQ ID NO's: 13, 35 and 14).

FIG. 2E: Provides a comparison of C-terminal amino acid sequences of wild type and mutant SUMO isoforms.

FIG. 17 discloses "GGTQE" as SEQ ID NO: 32.

FIG. 22 discloses "EQTG" as SEQ ID NO: 33.

FIG. 23 is a table summarizing identified SUMOylation sites from NTA enriched protein extracts from in vivo HEK293 cells exposed to $As_2O_3$ (see FIGS. 20-21).

FIG. 26 is a table summarizing identified SUMOylation sites on human histones following in vitro SUMOylation with His-SUMO1 mutant with and without immunoaffinity purification (IP). The columns labeled before and after IP indicated whether or not the SUMOylated peptide was identified in the corresponding LC-MS/MS analyses. Note that H3K23 was also identified from the in vivo experiments on HEK293 cells (see FIGS. 20 and 22).

DETAILED DESCRIPTION

Figure 1:
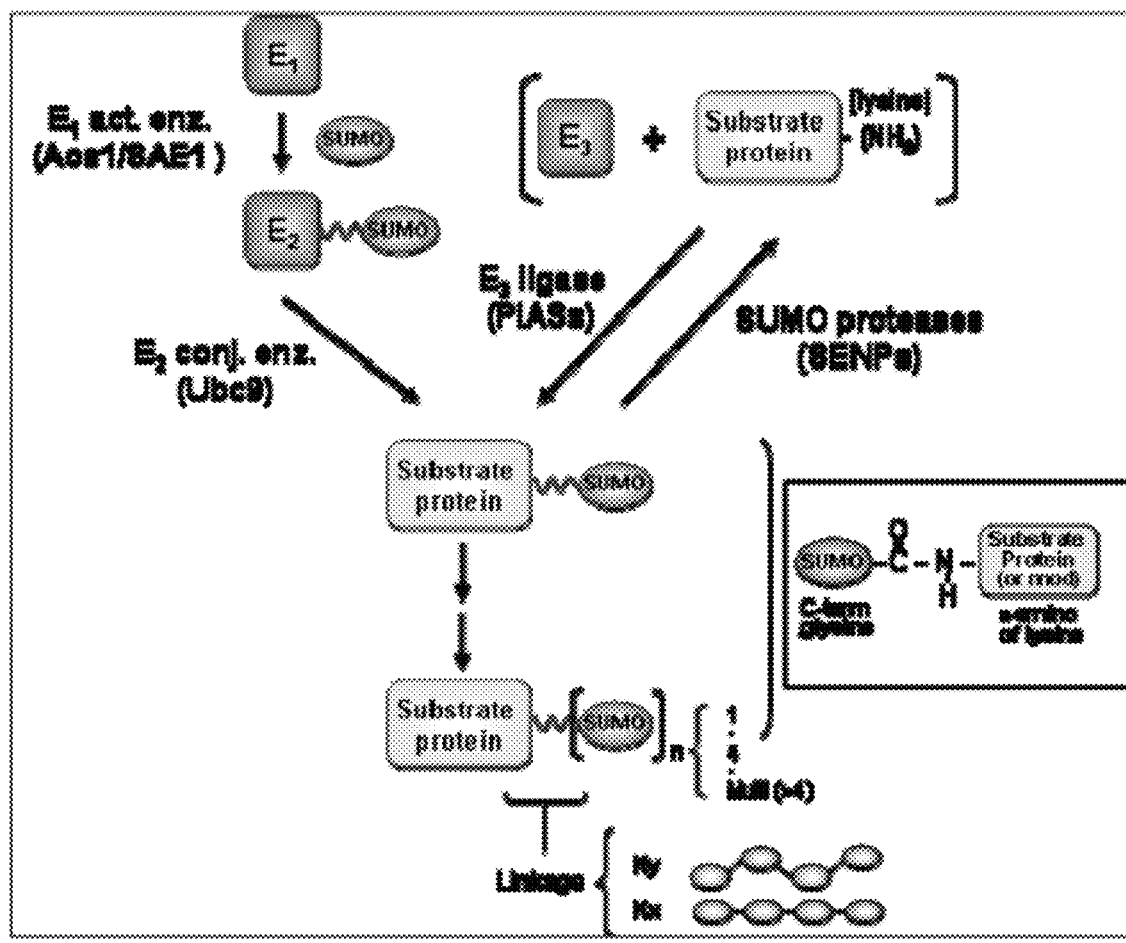
FIG. 1 is a diagram showing the regulation of the SUMO modifier system in mammalian cells.

Definitions:

Unless otherwise specified, the following definitions apply throughout:

As used herein, the singular forms "a", "an", and "the" include plural referents unless the context clearly indicates otherwise. Thus, for example, reference to "a mutation" includes one or more of such mutations and reference to "the method" includes reference to equivalent steps and methods known to those of ordinary skill in the art that could be modified or substituted for the methods described herein.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

Figure 2A:
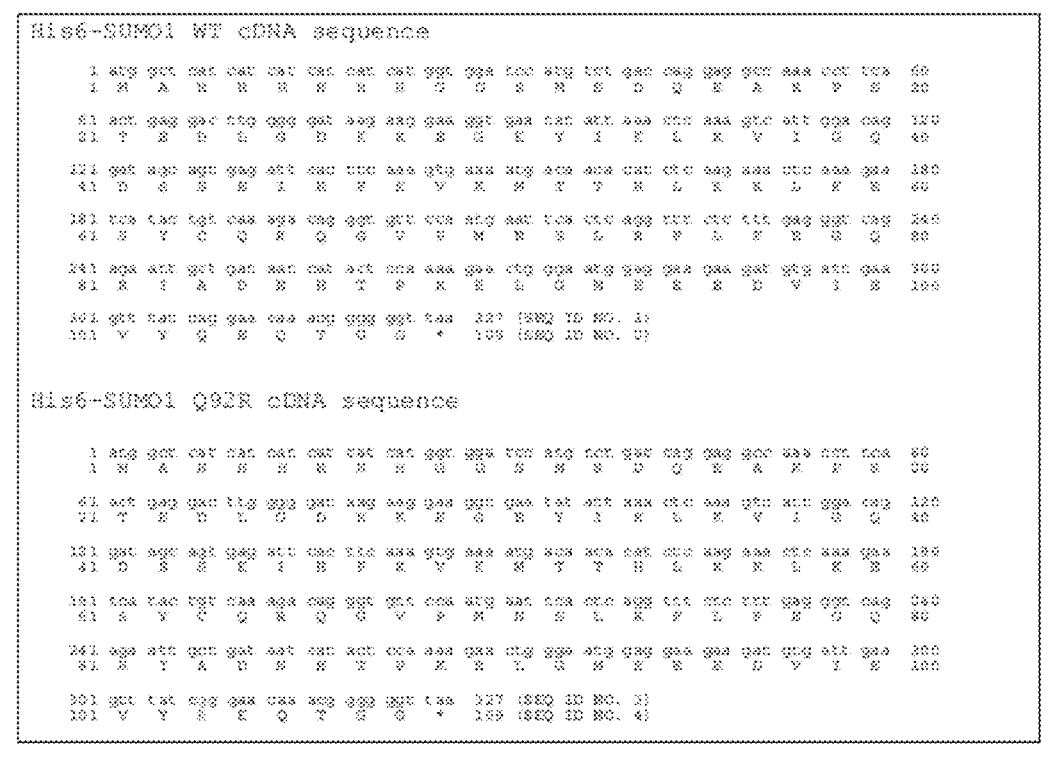

As used herein, the term "SUMO" is intended to refer to a small ubiquitin-like modified protein, a polypeptide or fragment thereof, encoded by a SUMO gene. Examples of Wild-type (WT) human SUMO proteins include the SUMO protein isoforms known as SUMO-1, SUMO-2, SUMO-3 and SUMO-4, as illustrated in FIGS. 2A (top: SEQ ID NO's: 1 and 2), 2B (top: SEQ ID NO's: 5 and 6), 2C (top: SEQ ID NO's: 9 and 10) and 2D (SEQ ID NO's: 13 and 14). Human SUMO-1 and SUMO-2 are identical to those of murine SUMO-1 and SUMO-2. Referring to FIG. 2, SUMO2 and 3 share 96% sequence homology whereas 52% is obtained between SUMO1 and SUMO3. The polypeptide sequence of murine SUMO-3 differs from human SUMO-3 at position 93-103, although residues 1-92 are identical.

The terms "mutated SUMO protein" and "mutated SUMO polypeptide" are used interchangeably throughout and are intended to mean a WT SUMO protein in which one or more of the last 25 C-terminus amino acid residues have been changed. In certain examples described herein, glutamine and glutamic acid residues in the C-terminal site of the WT SUMO isoforms, have been replaced by arginine or asparagine residues, but other amino acid substitutions can be considered to provide convenient cleavage sites (e.g. methionine, cysteine, aspartic acid, glutamic acid, lysine or arginine) in the expressed proteins. The location of the mutation sites refer to the endogenous expressed WT product (including the N-term Met residue) of each paralog. SUMO1 is slightly longer than SUMO2 and SUMO3. For each construct, we introduced a His6 (SEQ ID NO: 31) at the N-terminus plus mutations specific to each paralog. The nomenclature is:

His6-SUMO1 Q92R mutant: Substitution of the Gln (Q) residue for Arg (R) at position 92 in the endogenous SUMO1 protein.

His6-SUMO2 Q88R mutant: Substitution of the Gln (Q) residue for Arg (R) at position 88 in the endogenous SUMO2 protein.

His6-SUMO3 Q87R, Q88N mutant: Substitution of the Gln (Q) residue for Arg (R) at position 87 and Gln (Q) residue for Asn (N) at position 88 in the endogenous SUMO3 protein.

Specific examples of mutated SUMO isoforms are illustrated in FIGS. 2A (bottom: SEQ ID NO: 3 and 4), 2B (bottom: SEQ ID NO's: 7 and 8), and 2C (bottom: SEQ ID NO's: 11 and 12). The corresponding substitutions in amino acid sequence are illustrated in FIG. 2E.

As used herein, the term "SUMO gene" is intended to mean a gene encoding a SUMO polypeptide having a SUMOylation site. The SUMO gene is a gene having about 50% or greater nucleotide sequence identity to at least one of human SUMO-1, SUMO-2, SUMO-3 and SUMO-4, as illustrated in FIGS. 2A through 2E. The region of sequence over which identity is measured is a region encoding the SUMOylation site. Mammalian SUMO genes include nucleotide sequences isolated from any mammalian source. Human SUMO-1 and SUMO-2 are identical to those of murine SUMO-1 and SUMO-2.

As used herein, the term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

As used herein, the term "SUMOylation site" is intended to mean a site in the WT SUMO polypeptide sequence or the mutated SUMO polypeptide sequence, which reacts with a SUMO substrate. Based on experimental observations, the known SUMOylation sites are classified into two clusters, including Type I (consensus) and Type II (non-consensus) sites. Type I sites followed the ψKXE (ψ is A, I, L, M, P, F, or V and X is any amino acid residue) motif [Geiss-Friedlander, R., Melchior, F., Concepts in sumoylation: a decade on. *Nat. Rev. Mol. Cell Biol.* 2007, 8, 947-956; Rodriguez, M. S., Dargemont, C., Hay, R. T., SUMO-1 conjugation in vivo requires both a consensus modification motif and nuclear targeting. *J. Biol. Chem.* 2001, 276, 12654-12659.], while Type II sites contained other non-canonical sites.

As used herein, the term "nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids described herein, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Whenever applicable, the term "isolated nucleic acid" may also refer to a RNA molecule encoded by an isolated DNA molecule as defined above. Alternatively, the term may refer to an RNA molecule that has been sufficiently separated from other nucleic acids with which it would be associated in its natural state (i.e. in cells or tissues). An "isolated nucleic acid" (either DNA or RNA) may further represent a molecule produced directly by biological or synthetic means and separated from other components present during its production.

As used herein, the term "vector" is intended to mean a replicon, such as a plasmid, cosmid, bacmid, phage or virus, to which another genetic sequence or element (either DNA or RNA) may be attached so as to bring about the replication of the attached sequence or element.

As used herein, the terms "percent similarity", "percent identity" and "percent homology" when referring to a particular sequence are used as set forth in the University of Wisconsin GCG software program.

As used herein, the term "substantially pure" is intended to refer to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). The present discovery encompasses substantially pure mutated SUMO 1, 2 and 3 isoforms (e.g., nucleic acids, oligonucleotides, proteins, fragments, mutants, etc.).

As used herein, the term "oligonucleotide" is intended to refer to sequences, primers and probes of the present discovery, and is defined as a nucleic acid molecule comprised of two or more ribo- or deoxyribonucleotides, preferably more than three. The exact size of the oligonucleotide will depend on various factors and on the particular application and use of the oligonucleotide.

As used herein, the term "primer" is intended to refer to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically about 20-40, or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. According to some embodiments, primers are selected from Table 1 provided in the examples herein below.

As used herein, the term "probe" is intended to refer to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains about 20-40 or more nucleotides in length, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the discovery, to the substantial exclusion of hybridization of the oligonucleotide with single-stranded nucleic acids of non-complementary sequence. Appropriate conditions enabling specific hybridization of single-stranded nucleic acid molecules of varying complementarity are well known in the art. For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5 with every 1% decrease in homology. Thus, targets with greater than about 75% sequence identity would be observed using a hybridization temperature of 42° C.

The stringency of the hybridization and wash depends primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. With regard to the nucleic acids of the present discovery, a moderate stringency hybridization is defined as hybridization in 6×SSC, 5×Denhardt's solution, 0.5% SDS and 100 µg/ml denatured salmon sperm DNA at 42° C. and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

As used herein, the term "isolated protein" or "isolated and purified protein" is intended to refer to a protein produced by expression of an isolated nucleic acid molecule of the present discovery. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

As used herein, the term "amino acid" is intended to mean a radical derived from the corresponding α-amino acid by eliminating the hydroxyl of the carboxy group and one hydrogen of the alpha-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively. Amino Acid residues are provided below:

Three and single letter abbreviations for α-amino acids used throughout are as follows:

| Amino acid | Abbreviation | Abbreviation |
|---|---|---|
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Isoleucine | Ile | I |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "subject" is intended to mean humans and non-human mammals such as primates, cats, dogs, swine, cattle, sheep, goats, horses, rabbits, rats, mice and the like.

As used herein, the term "solid support" refers to any solid or stationary material to which reagents such as antibodies, antigens, and other test components can be attached. Examples of solid supports include, without limitation, microtiter plates (or dish), microscope (e.g. glass) slides, coverslips, beads, cell culture flasks, chips (for example, silica-based, glass, or gold chip), membranes, particles (typically solid; for example, agarose, sepharose, polystyrene or magnetic beads), columns (or column materials), and test tubes. Typically, the solid supports are water insoluble.

As used herein, the term "instructional material" or a "user manual" includes a publication, a recording, a diagram, or any other medium of expression which can be used to communicate the usefulness of reagents for performing a method according to the present discovery.

As used herein, the term "biological sample" is intended to refer to a subset of the tissues of a biological organism, its cells or component parts (e.g. body fluids, including but not limited to, blood, mucus, lymphatic fluid, synovial fluid, cerebrospinal fluid, saliva, amniotic fluid, amniotic cord blood, urine, vaginal fluid and semen).

As used herein, the term "mutation" is intended to mean any alteration in a gene which alters function or expression of the gene products, such as mRNA and the encoded for protein. This include but is not limited to altering mutation, point mutation, truncation mutation, deletion mutation, frameshift mutation, and null mutation.

Figure 2B:
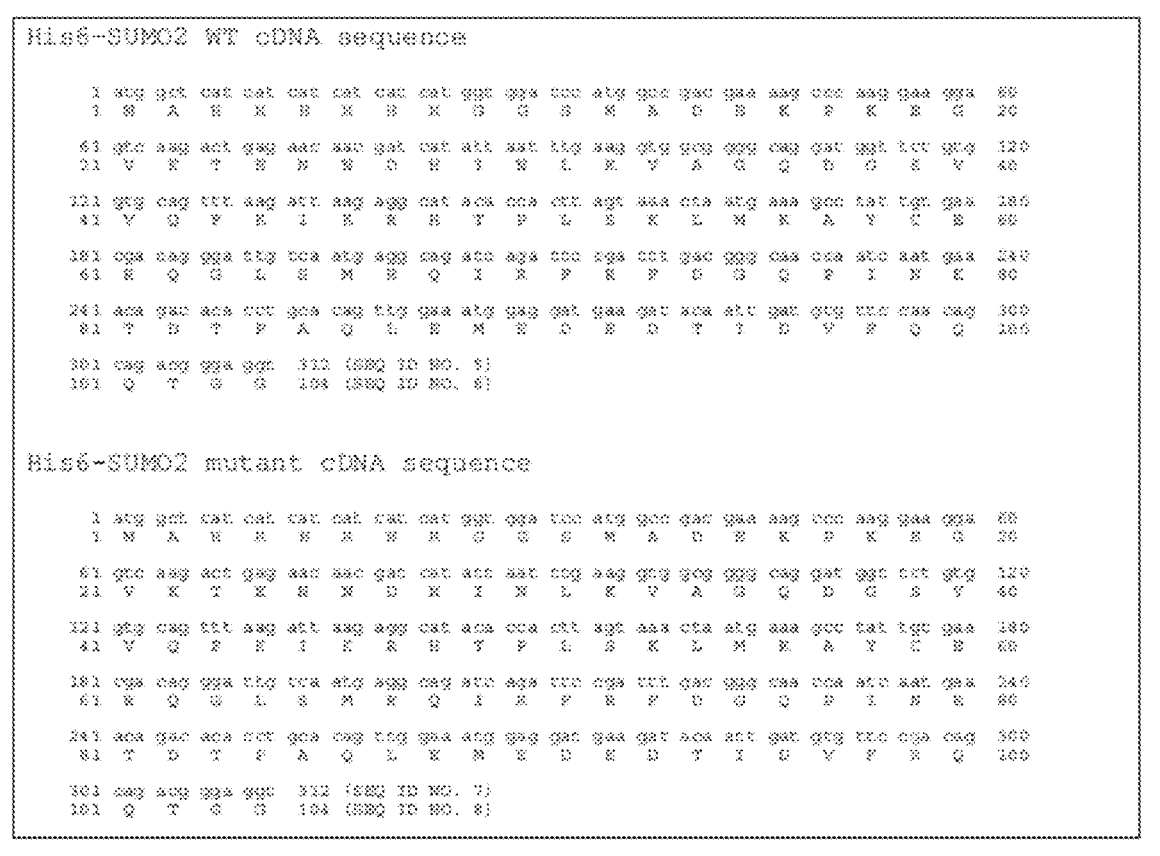
Figure 2C:
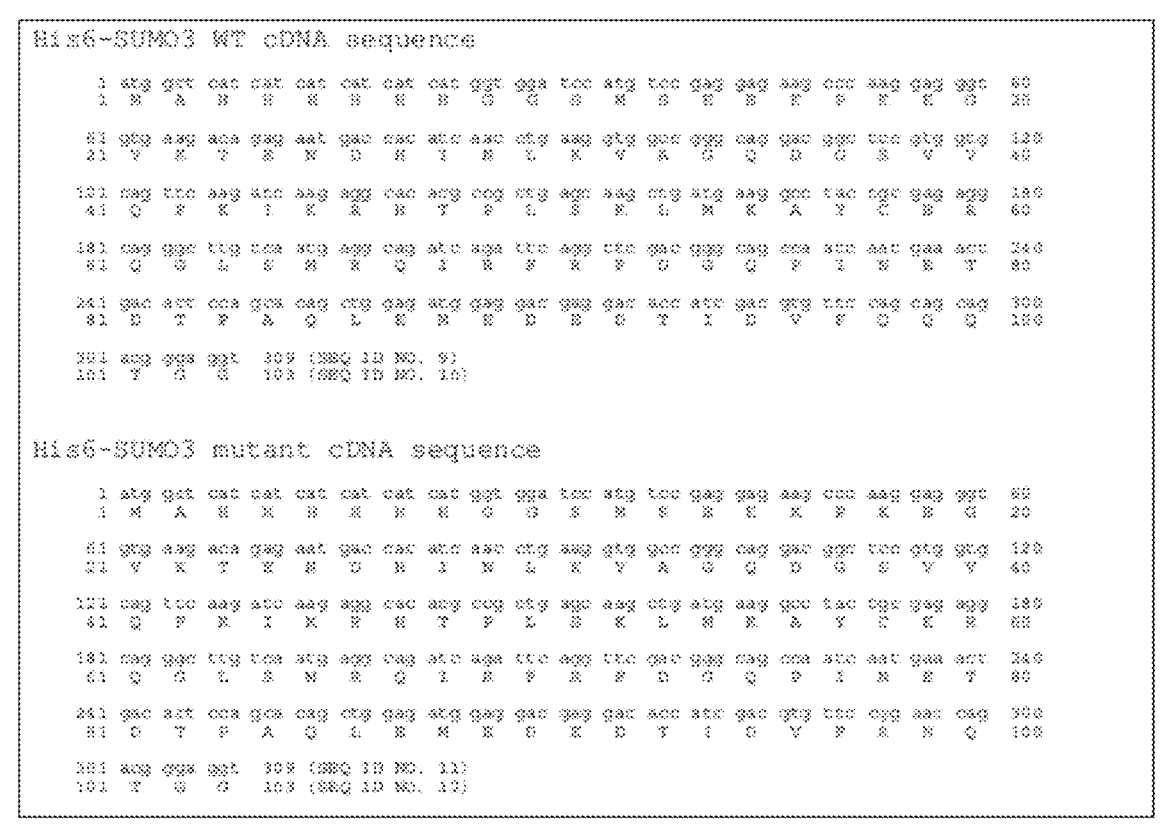
Figure 5:
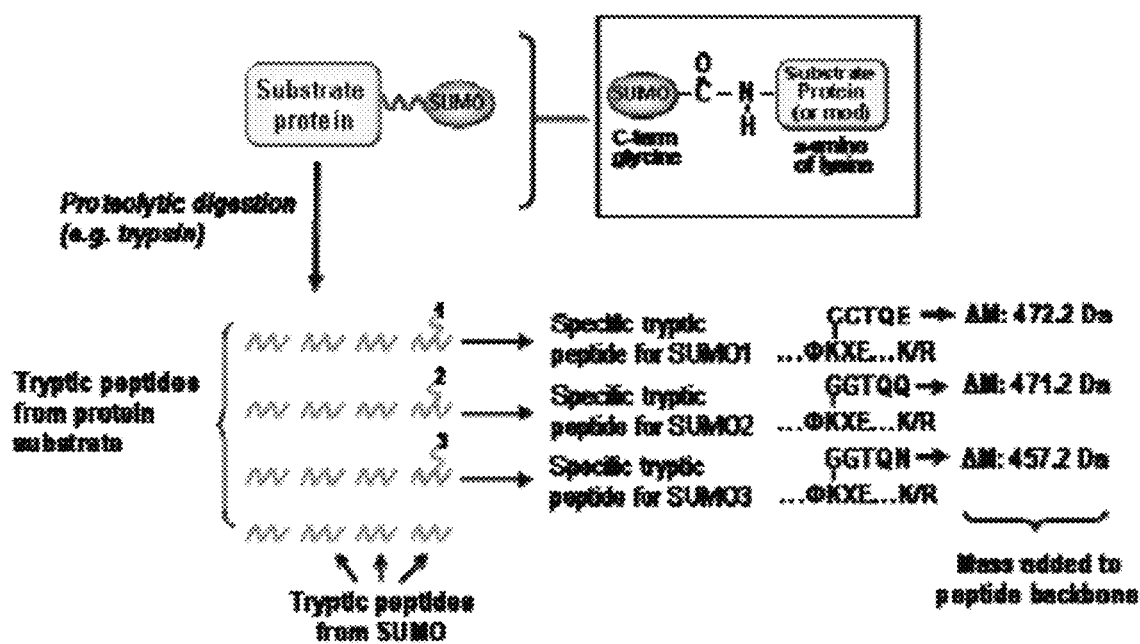
FIG. 5 illustrates the generation of tryptic peptides peptides (SEQ ID NOS 34, 36 and 37, respectively in order of appearance) from SUMO-modified proteins. A specific combination of amino acid residues unique to each SUMO isoform identifies the nature of the SUMO modification at the relevant lysine residue.

I: Nucleic Acid Molecules, Vectors, Cells, Transgenes and Transgenic Non-Human Mammals The discovery generally features mutated isoforms of SUMO proteins and a mass spectrometry-based proteomics approach for the large scale identification of protein SUMOylation sites. The mutant SUMO isoforms were characterized to facilitate the identification and quantitation of protein SUMOylation in mammalian cells. Gene constructs of SUMO isoforms were engineered to include a His6 affinity tag (SEQ ID NO: 31) and a mutated amino acid of position 5 from the C-terminus of the extracted protein (FIGS. 2A through 2C). The mutated isoforms of SUMO proteins retain their activity, when compared to Wild-type SUMO proteins. In particular, the discovery features a substantially pure DNA molecule, such as genomic, cDNA, or a synthetic DNA molecule, that encodes one of the mammalian SUMO isoforms in which one or more nucleotide substitutions have been incorporated near the end of its expressed sequence, as illustrated in FIGS. 2A (top), 2B (top), and 2C (top). Advantageously, the nucleotide substitution is different for each SUMO isoform and therefore each mutated SUMO isoform provides a convenient site for proteolytic cleavage by trypsin in the expressed protein product, which generates small and distinct SUMO stubs (or SUMOylated protein substrate fragment), as illustrated in FIG. 5 and below, and which are readily and easily detectable. Moreover, the methods described below can be used to easily and simultaneously differentiate between the mutated SUMO isoforms. For example, protein substrates comprising different SUMO isoforms can be distinguished by the specific mass of the five amino acid segment attached to the modified lysine residue, as shown below:

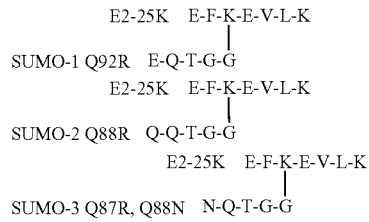

where the line between the K residue and the G residue is a covalent bond.

In certain embodiments, the discovery features DNA sequences substantially identical to the DNA sequences, or a fragment thereof, as illustrated in FIGS. 2A through 2C (SEQ ID NO's: 3, 7 and 11). In another aspect, the discovery also features RNA which is encoded by the DNA described herein. In one example, the RNA is mRNA. In another example, the RNA is antisense RNA.

Also contemplated in the scope of the present discovery are oligonucleotide probes, which specifically hybridize with the nucleic acid molecules of the discovery. In certain examples, the probe specifically hybridizes with mutated SUMO nucleic acid molecules (e.g. a nucleic acid having a sequence encoding a mutated SUMO protein) while not hybridizing with the wild type or "normal" sequence under high or very high stringency conditions. Primers capable of specifically amplifying mutated SUMO encoding nucleic acids described herein are also contemplated herein. As mentioned previously, such oligonucleotides are useful as probes and primers for detecting, isolating or amplifying mutated SUMO genes.

Nucleic acid molecules encoding the mutated SUMO proteins of the discovery can be prepared by known general methods or isolated from appropriate biological sources using methods known in the art. Additionally, cDNA or genomic clones having homology with human and other known mammalian SUMO, for example, mouse, rat, and the like, may be isolated from other species using oligonucleotide probes corresponding to predetermined sequences within the human SUMO encoding nucleic acids.

Nucleic acids of the present discovery may be maintained as DNA in any convenient vector. Accordingly, the discovery encompasses vectors comprising a nucleic acid molecule of the discovery, and more particularly a plasmid expression vector. The present discovery also encompasses host cells transformed with such vectors and transgenic animals comprising such a nucleic acid molecule of the present discovery. Those cells and animals could serve as models of disease in order to study the mechanism of the function of the SUMO gene and also allow for the screening of therapeutics.

In some embodiments, the vector, host cell or transgenic animal comprise a nucleic acid molecule (a transgene) encoding a mutated SUMO protein that is expressed or delivered to tissues. The host cell is a transformed and stable cell line constitutively expressing the mutant SUMO isoform.

Methods for producing host cells and transgenic animals are known in the art. Host cells include, but are not limited to mammalian, yeast or bacterial cells Transgenic animals can be selected from non-human mammals such as farm animals (such as pigs, goats, sheep, cows, horses, rabbits, and the like), rodents (such as rats, guinea pigs, mice, and the like), non-human primates (such as baboon, monkeys, chimpanzees, and the like), and domestic animals (such as dogs, cats, and the like) and wild and domestic (such as swans, ducks, fowl and the like). A transgenic animal according to the present discovery is an animal having cells that contain a transgene which was introduced into the animal or an ancestor of the animal at a prenatal (embryonic) stage. The cells and transgenic animals can be useful to identify sumoylated proteins specific to each organ in response to therapeutic treatment.

II: Mutated SUMO Polypeptides

A mutated SUMO polypeptide sequence may have 80% homology or more with any of the amino acid sequences disclosed herein. A mutated SUMO polypeptide sequence according to the present discovery may also comprise at least 50 or more contiguous amino acids of any of sequences disclosed herein.

In some embodiments, the mutated SUMO polypeptide is an isolated mutated SUMO-1, SUMO-2 or SUMO-3 protein. In certain examples, the mutated SUMO polypeptide comprises one or more mutations selected from Q92R, E93R, Q94R (SUMO-1); Q88R (SUMO-2); and Q87R, Q88N (SUMO-3). In specific examples, the mutated SUMO polypeptides include SEQ ID NO's: 4, 8 and 12.

Mutated SUMO proteins or polypeptides of the present discovery may be prepared in a variety of ways, according to known methods. The proteins may be purified from appropriate sources, e.g., transformed bacterial or animal cultured cells or tissues, by immunoaffinity purification. The availability of nucleic acid molecules encoding mutated SUMO protein enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Alternatively, larger quantities of mutated SUMO proteins or polypeptides may be produced by expression in a suitable prokaryotic or eukaryotic system. For example, part or all of a DNA molecule encoding for mutated SUMO may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences. Mutated SUMO proteins or polypeptides produced by gene expression in a recombinant prokaryotic or eukaryotic system may be purified according to methods known in the art.

Thus, an embodiment of the present discovery includes a method of producing a mammalian mutated SUMO polypeptide includes providing a cell transformed with a nucleic acid sequence encoding a mammalian mutated SUMO polypeptide positioned for expression in the cell. The mutated SUMO polypeptide has the sequence as illustrated in FIGS. 2A (bottom: SEQ ID NO: 4), 2B (bottom: SEQ ID NO: 8), and 2C (bottom: SEQ ID NO: 12). The transformed cell is cultured under conditions for expressing the nucleic acid; which then produces the mammalian mutated SUMO polypeptide.

III: Detection Methods

One embodiment features a method for the large-scale identification of protein SUMOylation sites. The method comprises proteolytically digesting a mutated SUMOylated protein substrate, for example, E2-25 k ligase, RanGAP, PML, and the like, to release a fragment of the mutated SUMOylated protein substrate. Certain examples of fragments of the mutated SUMOylated protein substrate include, but are not limited to, the following:

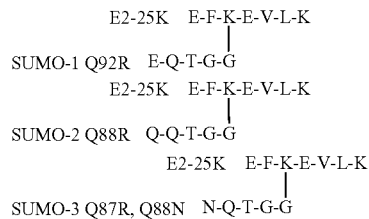

where the line between the K residue and the G residue is a covalent bond.

Specific fragment ions (e.g. m/z 275, 376, 433 or neutral loss of E (129 Da), EQ (257 Da), EQT (358 Da), EQTG (SEQ ID NO: 33) (405 Da), EQTGG (SEQ ID NO: 34) (462 Da)) corresponding to the cleavage of the mutated SUMO side chain can be used as signature ions to identify protein substrate and SUMOylation sites. The fragments are then detected using methods described herein below.

Figure 16A:
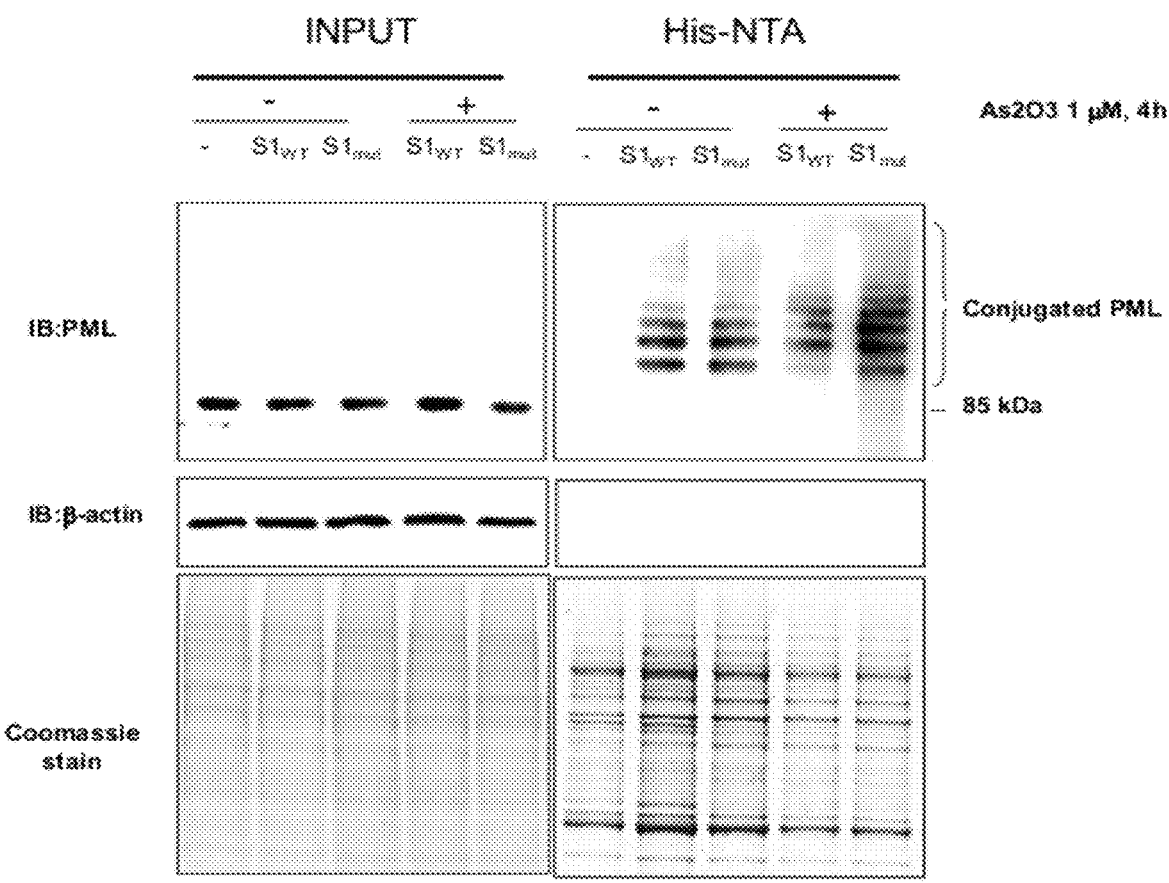
FIG. 16A illustrates His-SUMO pull downNTA protein enrichment experiments with His-SUMO1 WT and mutant. Immunoblots anti-PML shows the conjugations of His-SUMO1 WT and mutant to PML III protein with and without $As_2O_3$.
Figure 16B:
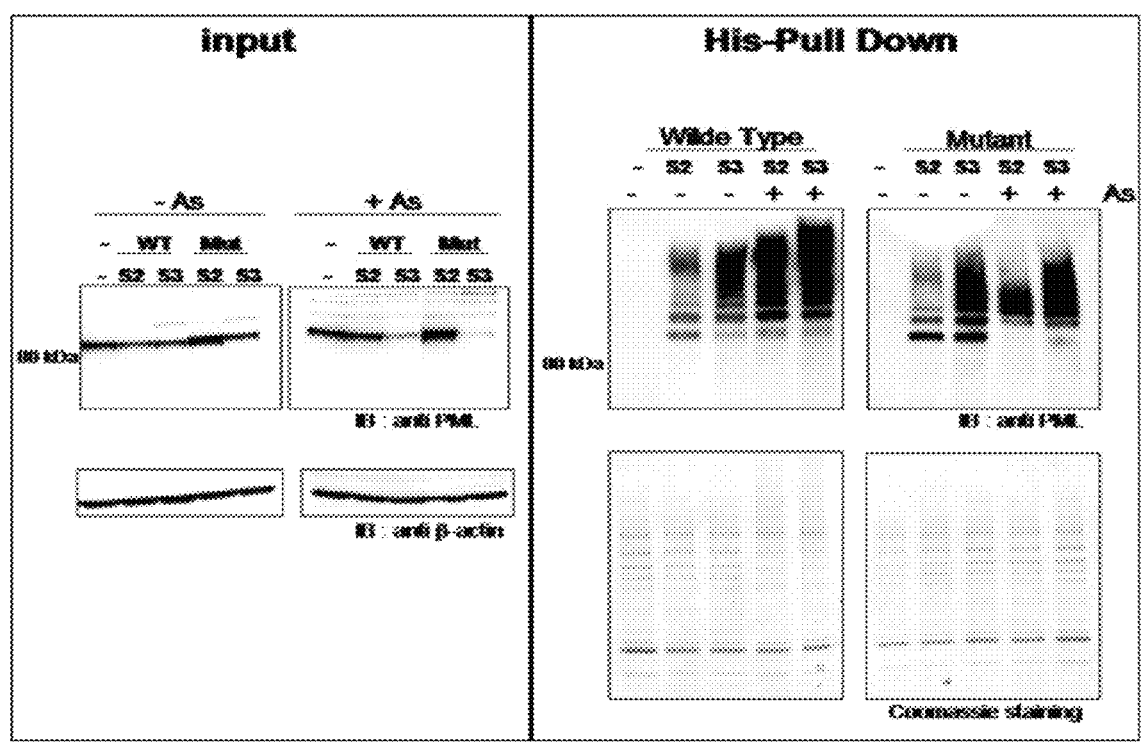
FIG. 16B illustrates His-SUMO Pull downNTA protein enrichment with His-SUMO 2,3 WT and mutant. Immunoblots anti-PML shows the conjugations of His-SUMO2 and SUMO3 WT and mutant to PML III protein with and without $As_2O_3$.

Another aspect of the discovery features an affinity enrichment method to facilitate protein SUMOylation in large-scale experiments performed on crude cell extracts. This is achieved using a dual affinity purification method. In the dual affinity method include expressing mutated SUMO isoforms, which comprise a His-tag at the N-terminus and mutations near the end of the C-terminus of the expressed protein, as illustrated in FIGS. 2A (bottom), 2B (bottom), 2C (bottom) and 2E. The mutations introduce an arginine residue near the C-terminus and do not compromise the function of the respective SUMO isoforms. The mutated SUMO isoforms are proteolytically digested to release the short amino acid fragments covalently attached to the lysine of SUMOylated protein targets, as illustrated above. The fragments are then purified using antibodies that specifically bind to the fragment, as illustrated in FIG. 16. The immunoaffinity extracts are then analyzed using LC-MS. In specific embodiments, the discovery features SUMOylated protein substrates that can be identified following proteolytic digestions (e.g. trypsin) to release branched tryptic peptides comprising small and distinct five amino acid residues specific to each of the three SUMO isoforms as illustrated in FIG. 5.

Figure 6:
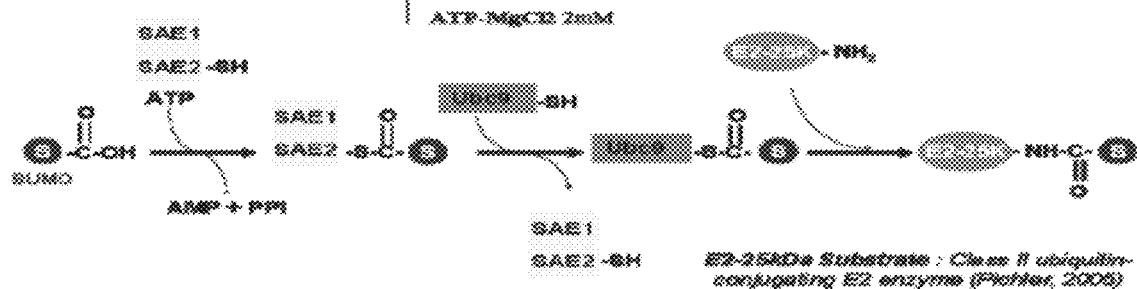
FIG. 6 is a diagram showing in vitro SUMOylation assay using Ubiquitin-conjugating enzyme E2 as protein substrate.
Figure 7:
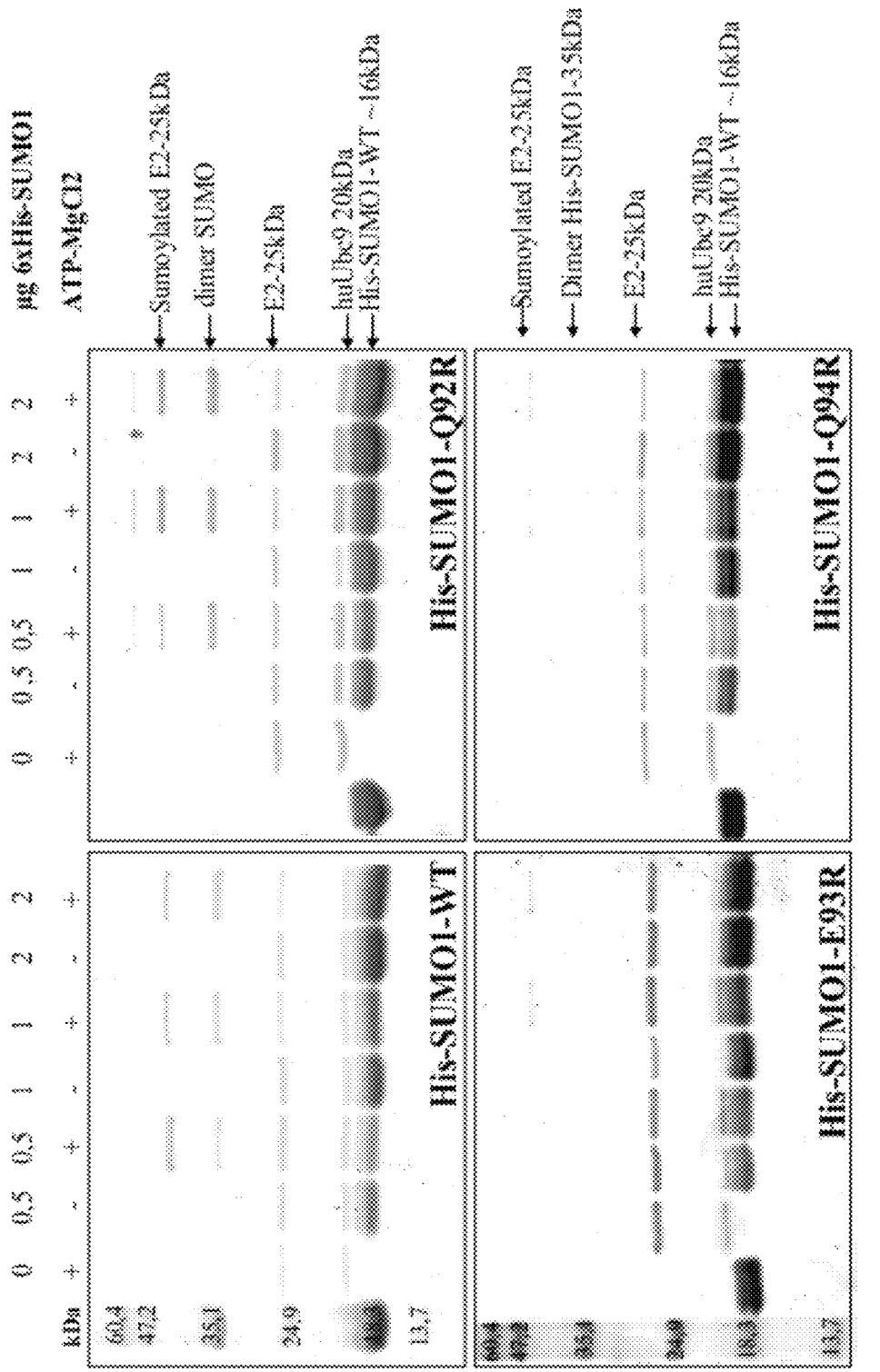
FIG. 7 illustrates Coomassie stained gel of in vitro SUMOylation assay using Ubiquitin-conjugating enzyme E2 as protein substrate. Each panel represent a different recombinant His6-SUMO1 (wild type, mutant Q92R, E93R and Q94R). In each case the SUMOylated E2 is observed as the highest molecular weight band.
Figure 8:
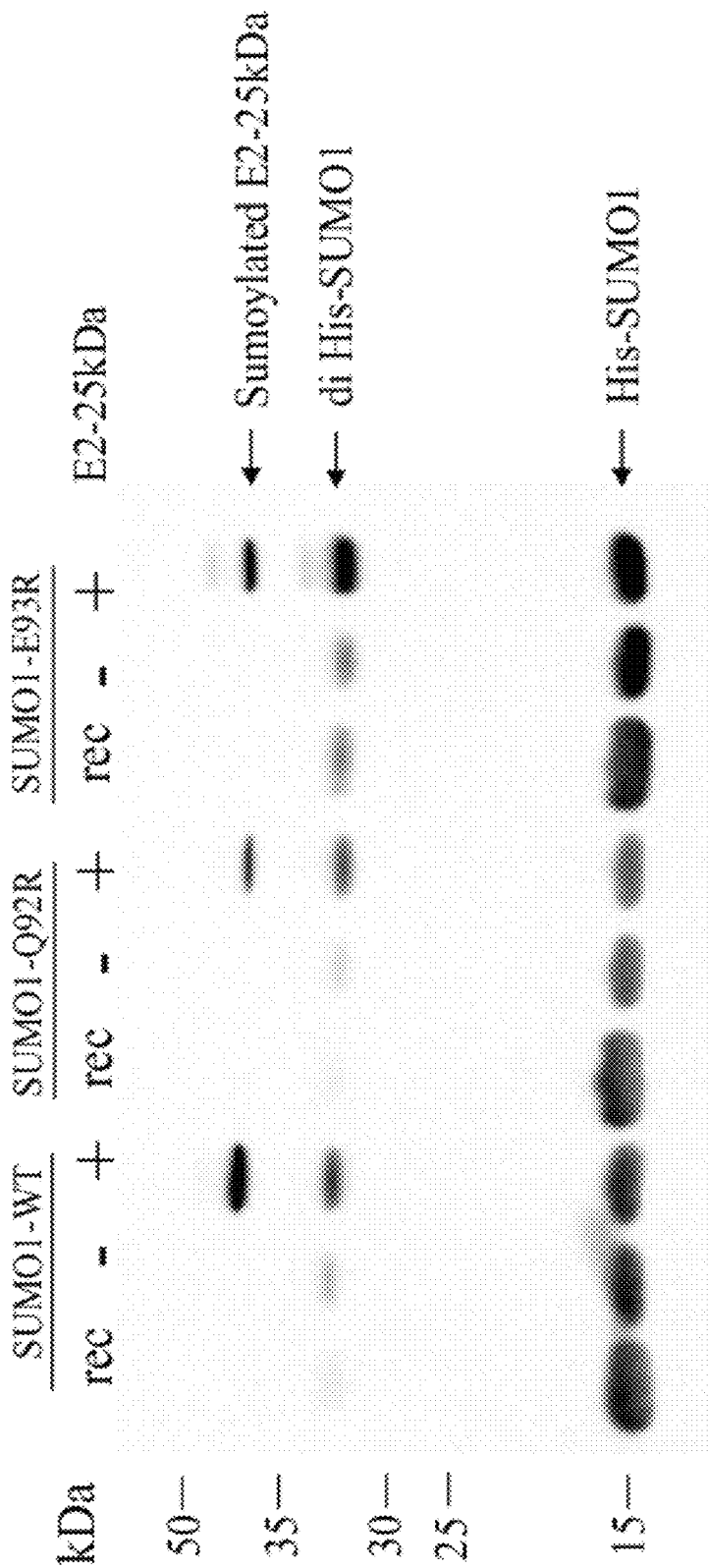
FIG. 8 Illustrates immunoblot of in vitro SUMOylation assay using Ubiquitin-conjugating enzyme E2 as protein substrate. Immunoblot is performed using an antibody that recognized the His6 epitope (SEQ ID NO: 31). Immunoblots are presented for different recombinant His6-SUMO1 (wild type, mutant Q92R, and E93R). In each case the SUMOylated E2 is observed as the highest molecular weight band.
Figure 12D:
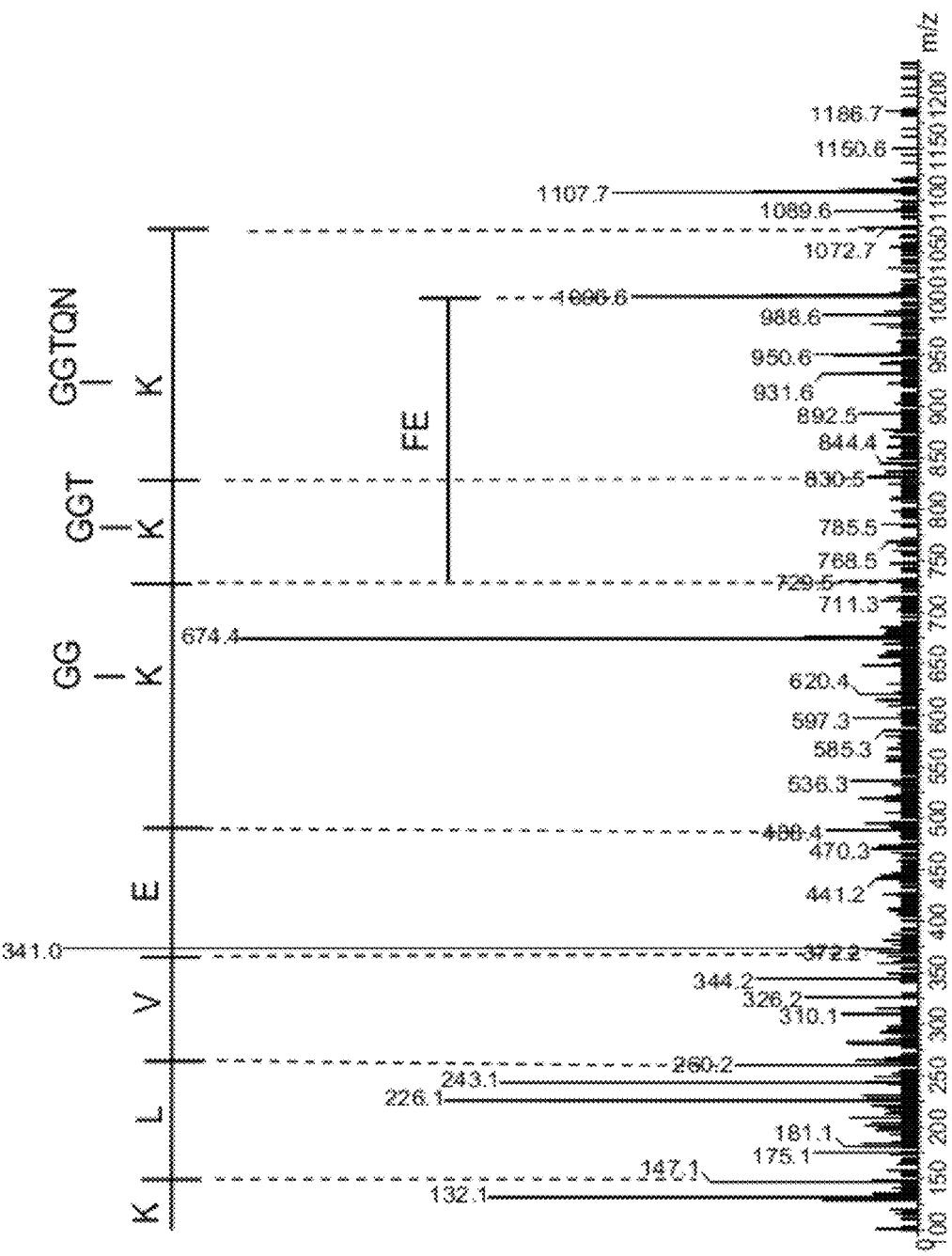
FIG. 12 illustrates tandem mass spectra of SUMOylated E2-ligase substrates. Mass spectrometry identification of SUMOylated lysine14 of Ubiquitin-conjugating enzyme E2 protein substrate from in gel digestion of the protein band from in vitro SUMOylation experiments (see FIG. 10). The CID MS/MS spectrum of the modified tryptic peptides comprising the SUMO side chain characteristic of each isoform is shown for each doubly-charged precursor ion (ie m/z 682.8 for SUMO1, m/z 682.5 for SUMO2, and m/z 675.3 for SUMO3).
Figure 13:
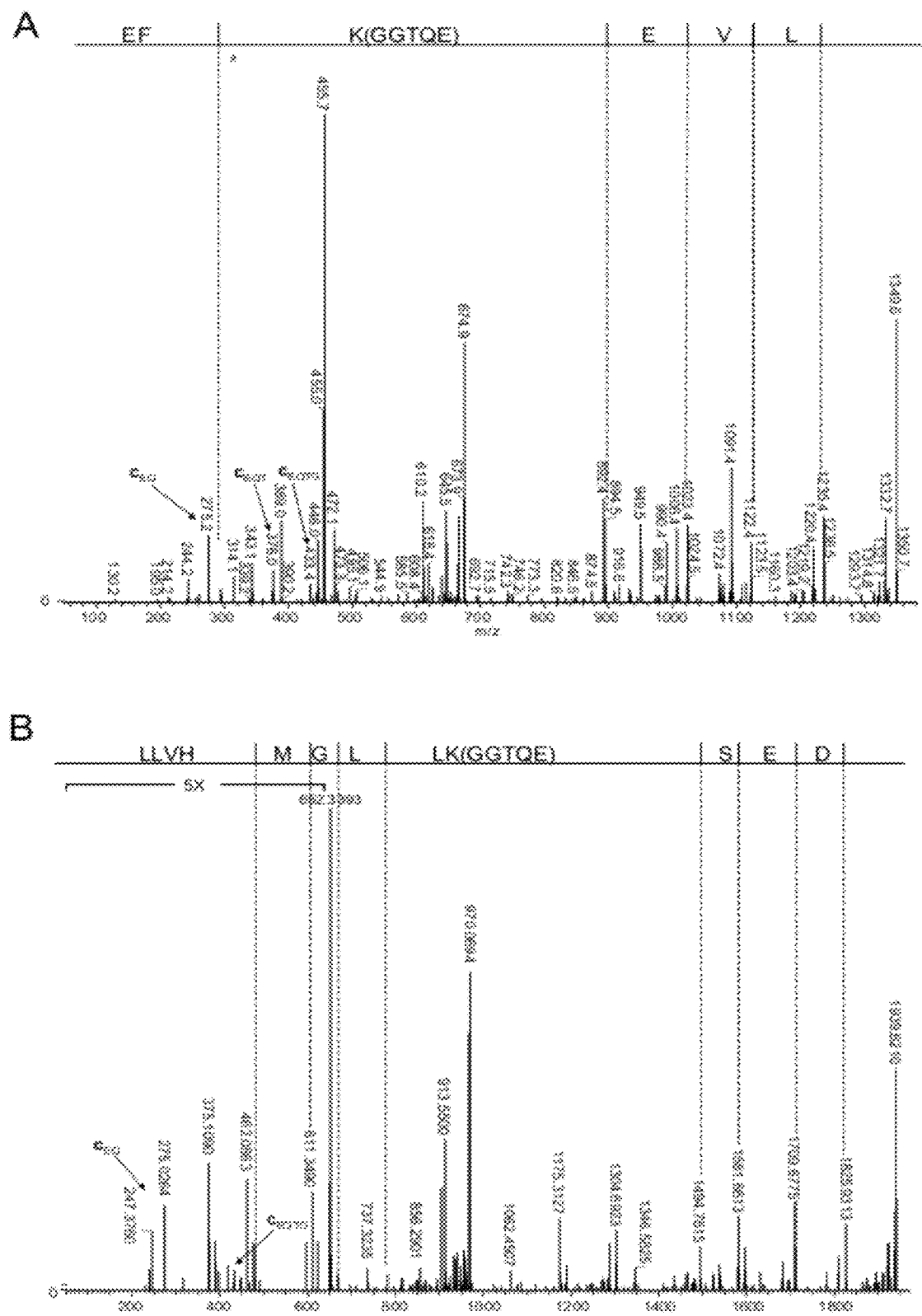
FIG. 13 illustrates mass spectrometry identification of E2-ligase and RanGAP substrates SUMOylated with SUMO1 in vitro SUMOylation experiments (see FIG. 11). The ETD mass spectrum of the tryptic SUMO peptide from E2-ligase (top) enabled the identification of lysine14 as the modified residue. The ETD mass spectrum of the tryptic SUMO peptide from RanGAP1 (bottom) enabled the identification of lysine524 as the modified residue. Fragment ions identified by $c_{EQ}$, $c_{EQT}$ and $c_{EQTG}$ (SEQ ID NO: 33) correspond to side chain cleavages specific to SUMO1 mutant.
Figure 13A:
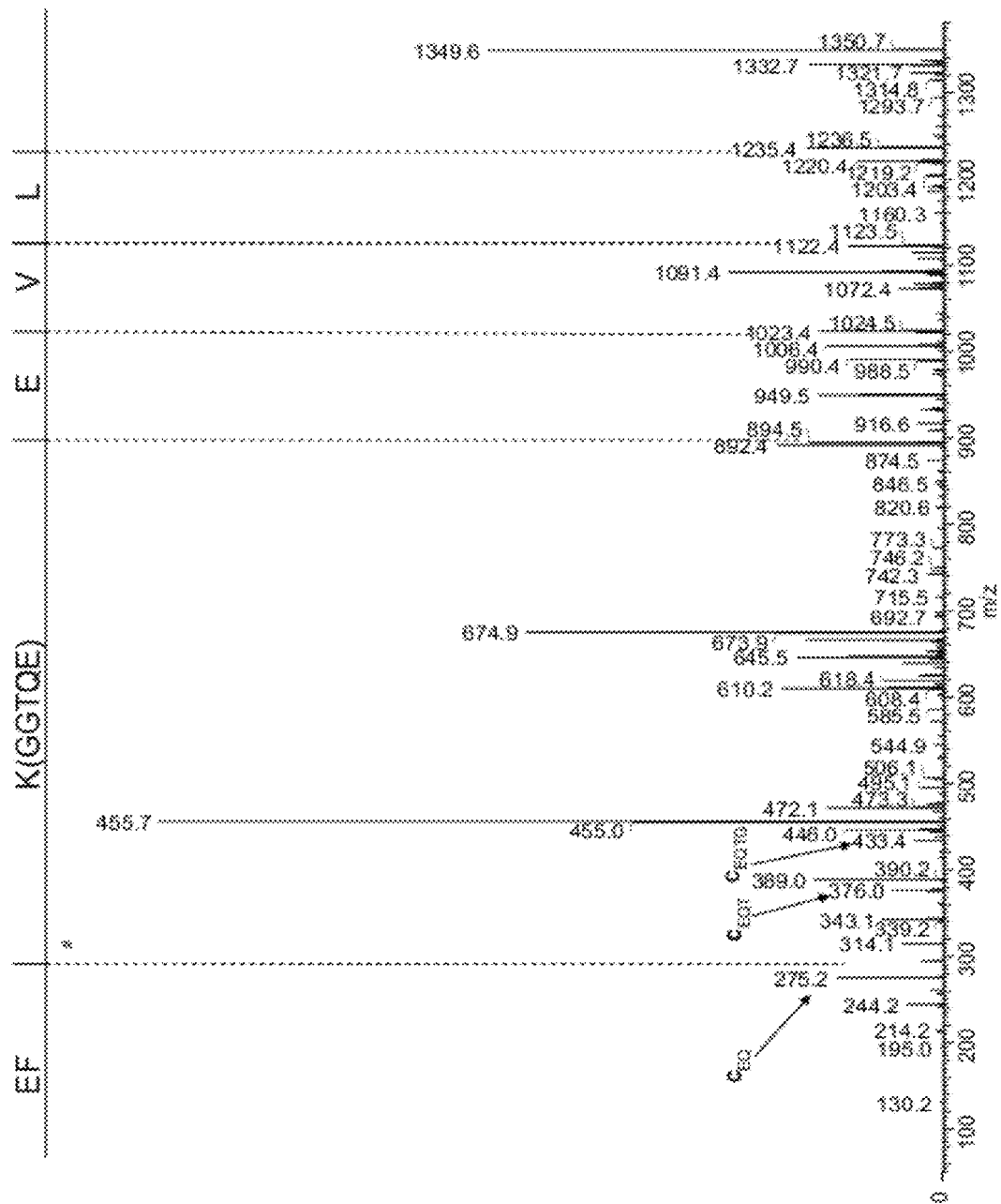
Figure 13B:
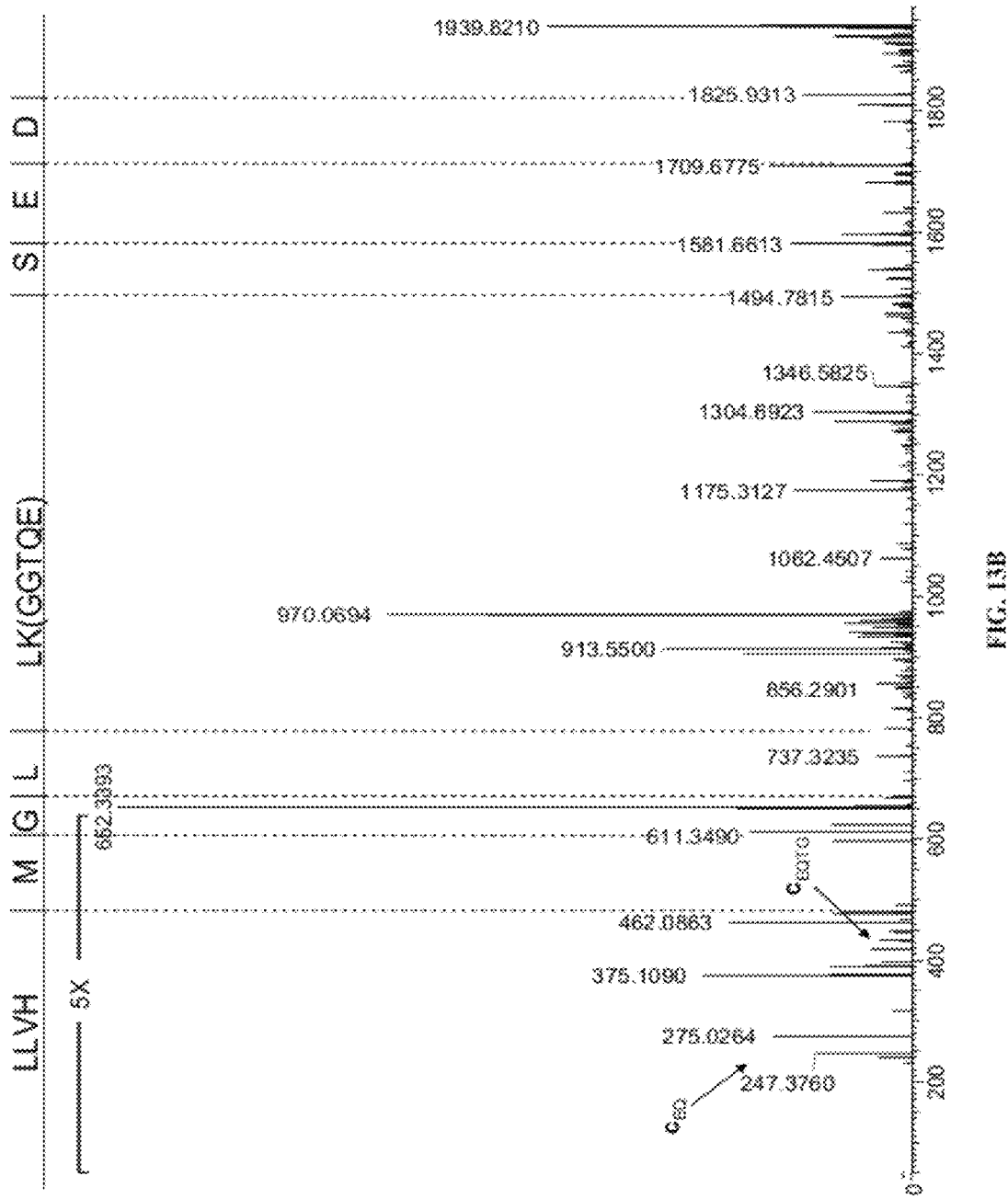

The modified tryptic peptides can be identified by mass spectrometry and peptide sequencing (tandem mass spectrometry) using collisional activation or other relevant ion dissociation mechanisms, for example, electron transfer dissociation, electron capture dissociation and the like. Recombinant SUMO isoform mutants can be used during in vitro SUMOylation experiments to follow the incorporation of relevant modified protein substrates, as illustrated in FIGS. 6 through 8. Identification of the modified residue can be achieved using tandem mass spectrometry as illustrated in FIGS. 12 and 13. In specific embodiments, the discovery relates to the use of tandem mass spectrometry with collisional activation and/or electron transfer dissociation to identify specific reporter ions for each SUMO isoform, as illustrated in FIGS. 12 and 13.

Figure 9:
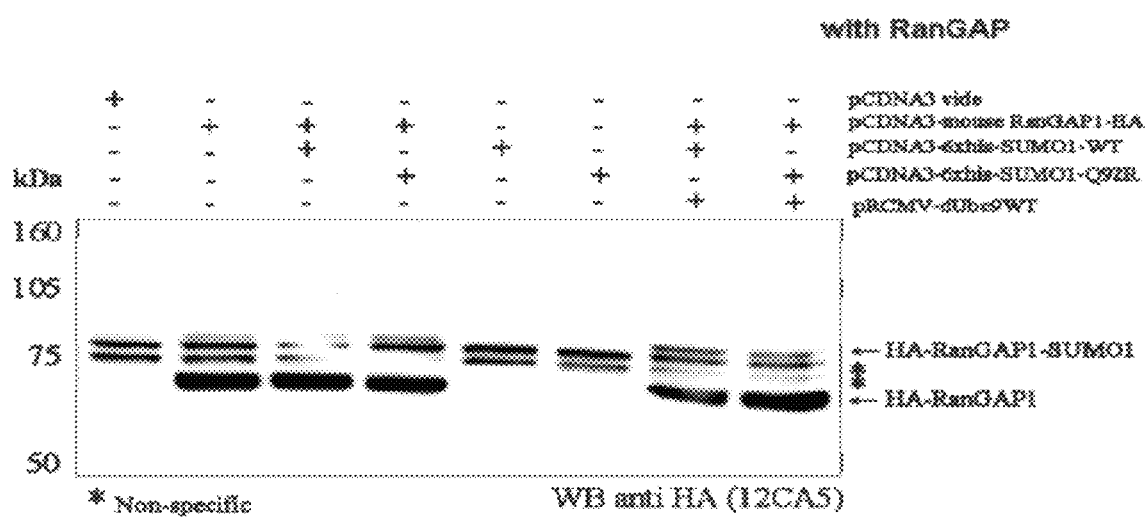
FIG. 9 illustrates immunoblot of in vivo SUMOylation assay using transfected HA-RanGAP as protein substrate. Immunoblots are performed using an antibody that recognized the HA epitope. Immunoblots are presented for His6-SUMO1 (wild type, and mutant Q92R). In each case the SUMOylated HA-RanGAP is observed as the highest molecular weight band.

SUMO isoform mutants can also be co-transfected in mammalian cells with target protein substrates. For example, RanGAP1, a known SUMOylation target forms a tight complex in association with NUP358 and UBE2I/UBC9. The ubiquitin-conjugating enzyme E2 interacts with UBE2I favoring the conjugation of SUMO1 to RANGAP1, and subsequently stabilizes interactions of SUMOylated RANGAP1 with RANBP2/NUP358. The SUMO1/RANGAP1/UBC9/NUP358 complex associates with nuclear pore complexes (Joseph, J., Tan, S. H., Karpova, T. S., McNally, J. G., and Dasso, M. (2002). SUMO-1 targets RanGAP1 to kinetochores and mitotic spindles. The Journal of cell biology 156, 595-602; Swaminathan, S., Kiendl, F., Korner, R., Lupetti, R., Hengst, L., and Melchior, F. (2004). RanGAP1*SUMO1 is phosphorylated at the onset of mitosis and remains associated with RanBP2 upon NPC disassembly. The Journal of cell biology 164, 965-971). The SUMO isoform mutants are also functional and can be conjugated to RanGAP1 following transfection of these proteins in HEK273 cells, as illustrated in FIG. 9.

Changes in protein SUMOylation in response to chemical or environmental stimulation, and across cell phenotypes can be monitored by measuring the abundance variation of relevant branched tryptic peptides comprising the five amino acid SUMO reporter sequence. For example, this approach could be used to monitor the overall change in SUMOylation of the substrate promyelocytic leukemia (PML) protein in response to $As_2O_3$ or interferon-γ. PML is a protein localized to PML-nuclear bodies, a dynamic sub-nuclear organelle tightly bound to the nuclear matrix that hosts many constitutive and transient proteins involved in the regulation of apoptosis, cellular senescence, proliferation, genomic stability and antiviral responses (Bernardi, R., and Pandolfi, P. P. (2007). Structure, dynamics and functions of promyelocytic leukaemia nuclear bodies. Nature reviews 8, 1006-1016).

The fusion of the PML gene to the retinoic acid receptor α (PML-RARα) is a common gene translocation event that initiates acute promyelocytic leukemia (APL) through impaired SUMOylation and repression of cell differentiation programs (Zhu, J., Zhou, J., Peres, L., Riaucoux, F., Honore, N., Kogan, S., and de The, H. (2005). A SUMOylation site in PML/RARA is essential for leukemic transformation. Cancer cell 7, 143-153).

Figure 14:
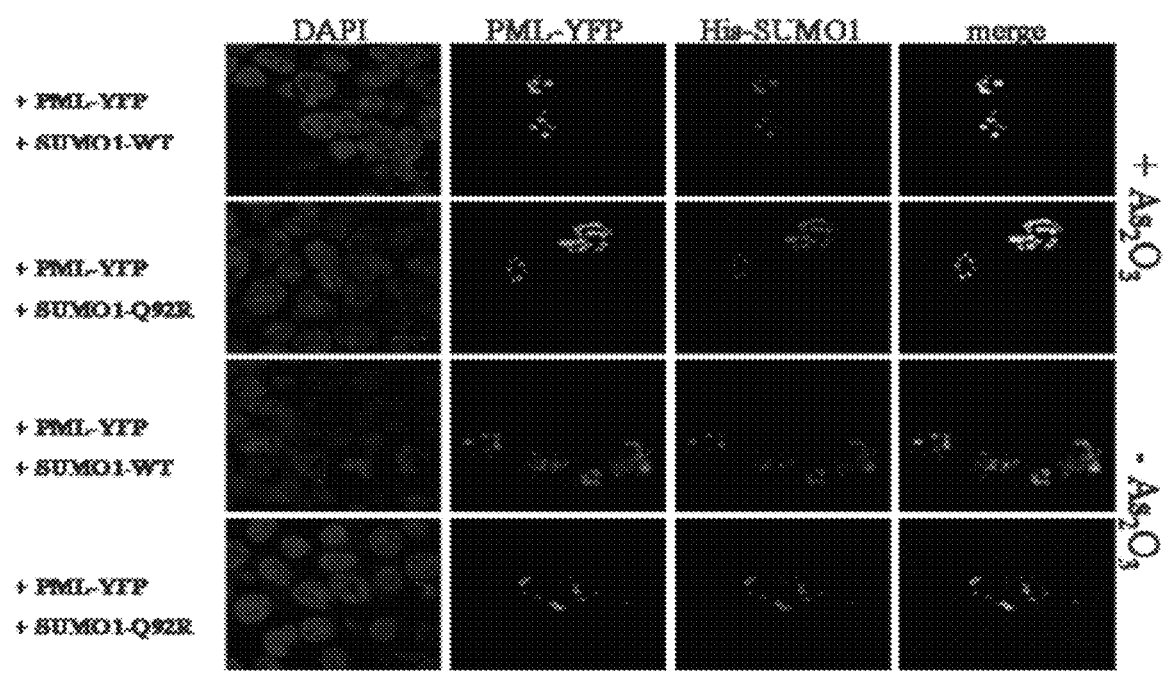
FIG. 14 illustrates $His_6$SUMO1 (Q92R) mutant which display similar functional properties to wild type counterparts from immunofluorescence experiments. Immunofluorescence microscopy of HEK293 human cells showing co-localization of PML-Yellow Fluorescence Protein with $His_6$ SUMO1 WT (top) and Q92R mutant (bottom) to nuclear bodies. Increase formation of PML-nuclear bodies is observed upon incubation with 1 μM $As_2O_3$. DAPI staining (nucleus).
Figure 15:
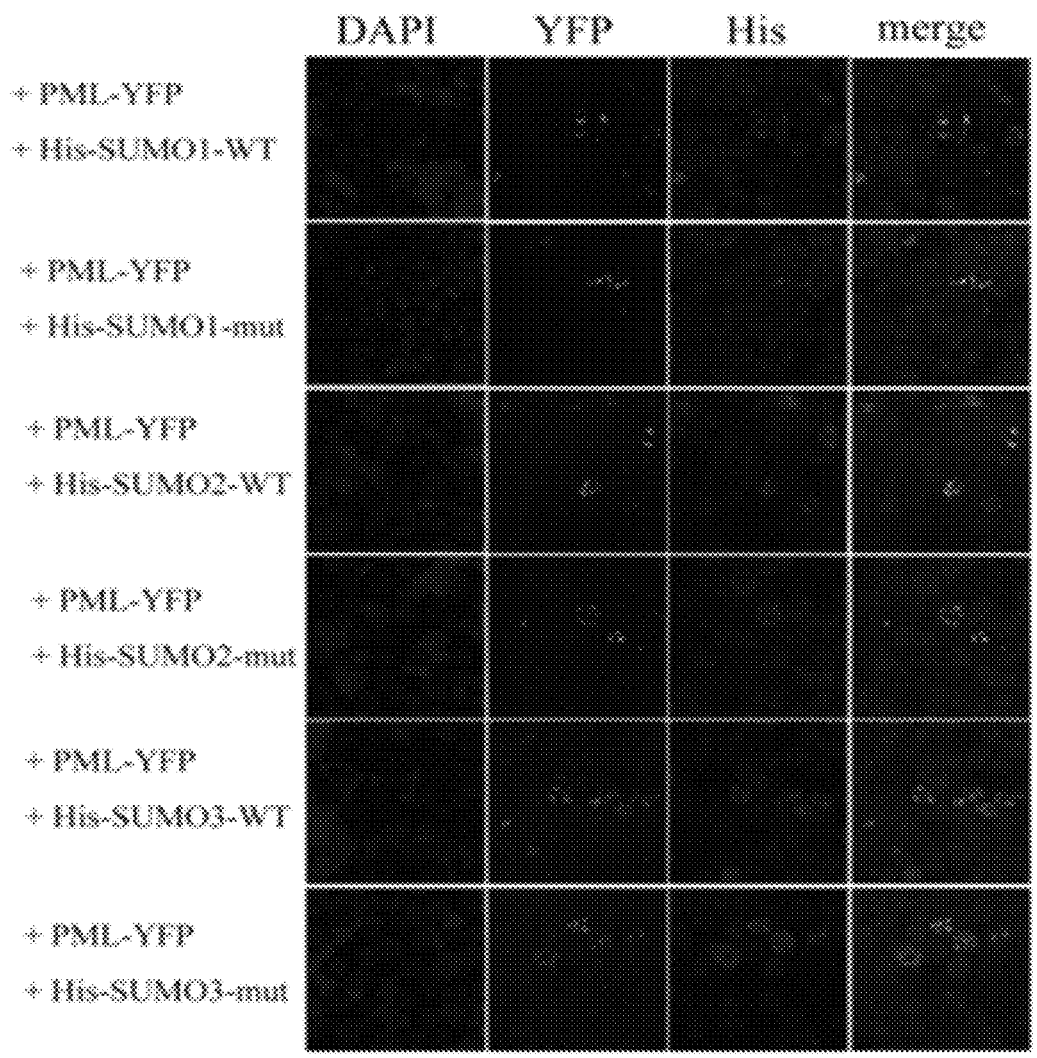
FIG. 15 illustrates all $His_6$SUMO mutants displayed similar functional properties to wild type counterparts from immunofluorescence experiments. Immunofluorescence microscopy of HEK293 human cells showing co-localization of PML-Yellow Fluorescence Protein with His6-SUMO1 WT, His6-SUMO1 mutant, His6-SUMO2 WT, His6-SUMO2 mutant, His6-SUMO3 WT, and His6-SUMO3 mutant to nuclear bodies, DAPI staining (nucleus).

SUMO isoform mutants have similar properties to their corresponding wild type counterparts. SUMOylated PML from either wild type or mutant SUMO isoforms are recruited to PML-nuclear bodies upon incubation with 1 μM $As_2O_3$, as illustrated in FIGS. 14 and 15.

Monitoring changes in protein SUMOylation can also be important to identify potential substrates targeted by specific E3-ligase. In a large-scale protein SUMOylation experiments, this can be achieved by monitoring changes in the covalent attachment of SUMO isoforms in affinity-enriched protein extracts following depletion by shRNA of potential E3-ligase enzymes.

The SUMOylation appears to be involved in many aspects of cancer from initiation to metastasis. One additional aspect of the present discovery includes a method of detecting in a subject susceptibility to develop misregulated expression of SUMO. The method would include taking a biological sample from the subject that contains a sufficient amount of a nucleic acid, for example DNA and sequencing predetermined regions of the DNA, which encodes encoding a SUMO polypeptide. By comparing this sequence with a corresponding sequence from a non-susceptible control subject, a SUMO mutation known to be indicative of the susceptibility can be identified.

The methods of the present discovery can be used to differentiate between mutant SUMO isoforms. This method involves providing a mutant strain expressing mutated SUMO-1, SUMO-2 and SUMO-3 polypeptides; incubating mutated the SUMO polypeptides with SUMO protein substrates to produce a SUMOylated protein substrates; enriching the SUMOylated protein substrates with affinity chromatography; digesting the SUMOylated protein substrates with trypsin to provide SUMOylated tryptic fragments; enriching the SUMOylated fragments with antibody that specifically binds to SUMOylated moiety; and identifying by mass spectrometry the SUMOylation sites and the type of SUMO isoform attached to the modified lysine residue.

IV: Antibodies and Kits

The present discovery also provides antibodies capable of immunospecifically binding to mutated SUMO proteins and polypeptides of the discovery. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be may be used for immunoaffinity enrichment of the mutated SUMO or they may be used in a kit for detecting in a subject the susceptibility to develop a condition or an increased likelihood of developing a condition characterized by impaired regulation of protein SUMOylation or by impaired protein SUMOylation.

Polyclonal antibodies directed toward SUMO protein, mutants and fragments thereof may be prepared according to standard methods. In a preferred embodiment, monoclonal antibodies are prepared, such antibodies reacting immunospecifically with predetermined epitopes of the SUMO protein. In preferred embodiments, the antibodies are immunologically specific to mutated SUMO proteins and polypeptides. Monoclonal antibodies may be prepared according to general methods known in the art. Polyclonal or monoclonal antibodies that immunospecifically interact with wild-type and/or mutant SUMO proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

One advantageous use of antibodies of the present discovery is in the use of a kit for monitoring the global sumoylation activity of a cell or the SUMOylation of specific protein substrates. This information could be used for purposes of diagnosis, prognosis or for predicting the response to treatment. Examples of diseases include but are not limited to cancer and neurodegenerative diseases. The kit would comprise a substantially pure antibody that specifically binds to a mammalian mutated SUMO polypeptide and a means for detecting the binding of the antibody to the mammalian SUMO polypeptide.

V: Screening Methods

One additional aspect of the discovery includes methods of identifying biological agents or small molecules that modulate the SUMOylation activity in the cell, specifically modification of protein SUMOylation or modification of the regulation of protein SUMOylation. This could also be exploited for example to screen for inhibitors, activators or modulators of SUMO E2 conjugating enzymes, SUMO E3 ligases or SUMO proteases. The identified agents or molecules could be exploited as research reagents or for therapeutic purposes. The method could be used for in vitro screening assays using purified SUMO modifying enzymes or for in vivo cell-based assays. The method comprises a) providing plasmid vectors encoding mutated SUMO isoforms or purified mutated SUMO isoforms, as described herein b) providing a substantially pure antibody that specifically binds to mutated SUMO polypeptide and c) a means for detecting the binding of the antibody to the mammalian SUMO polypeptide.

Alternatively, there is provided a method of monitoring whether an agent and/or conditions have an effect on the SUMOylation of SUMO protein substrates. This method comprises a) providing either i) plasmid vectors encoding first mutated SUMO polypeptides or ii) first purified mutated SUMO polypeptides; b) culturing a first cell line expressing mutated SUMO polypeptides to produce a reference sample comprising a first plurality of SUMOylated protein substrates; c) enriching first SUMOylated protein substrates with affinity chromatography; d) digesting the first SUMOylated protein substrates with trypsin to provide first SUMOylated tryptic fragments; e) enriching the first SUMOylated fragments with antibody that specifically binds to SUMOylated moiety to provide a first reference sample that can be profiled by mass spectrometry; f) culturing a second cell line expressing mutated SUMO polypeptides in the presence of the agent and/or conditions suspected of having an effect on the SUMOylation of the SUMO protein substrates to produce a second plurality of SUMOylated protein substrates; g) enriching the second SUMOylated protein substrates using affinity chromatography h) digesting the second SUMOylated protein substrates with trypsin to provide second SUMOylated tryptic fragments; i) enriching the second SUMOylated fragments with antibody that specifically binds to SUMOylated moiety to provide a second reference sample that can be profiled by mass spectrometry; and j) comparing the first reference profile from e) with the second reference profile from i) so as to monitor whether the agent and/or conditions has an effect on the SUMOylation of SUMO protein substrates.

Figure 21:
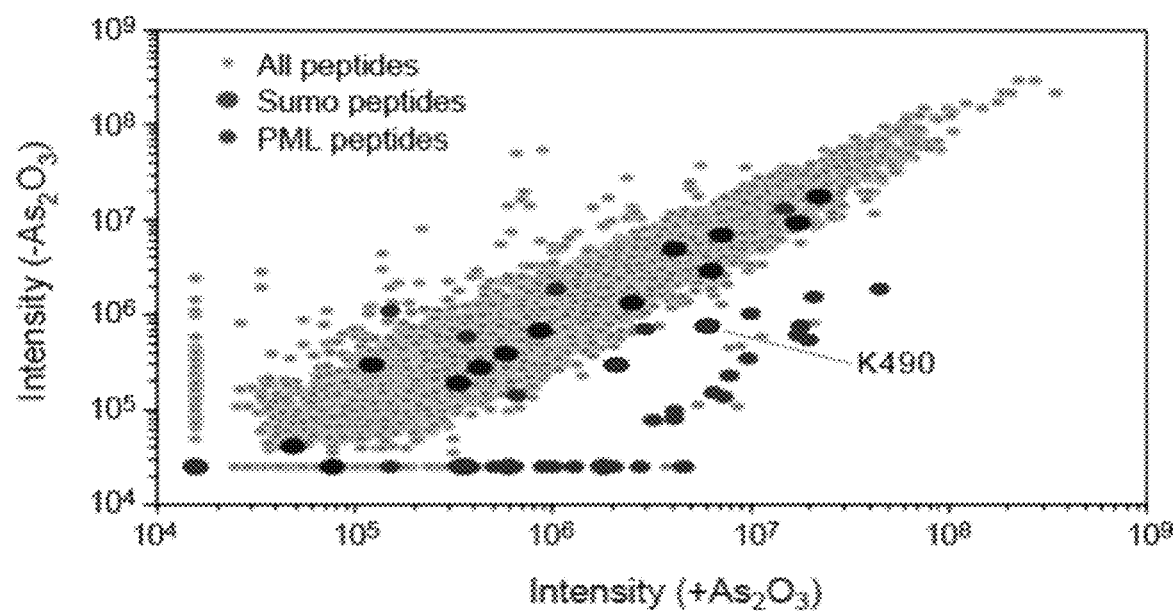
FIG. 21 is a scatter plot of tryptic peptides from NTA-purified His-SUMO3 proteins of HEK293 cells treated or not with $As_2O_3$. $As_2O_3$ PML peptides showed significant increased in abundance upon $As_2O_3$ treatment. Increased SUMOylation was observed for several PML peptides including K490.
Figure 22:
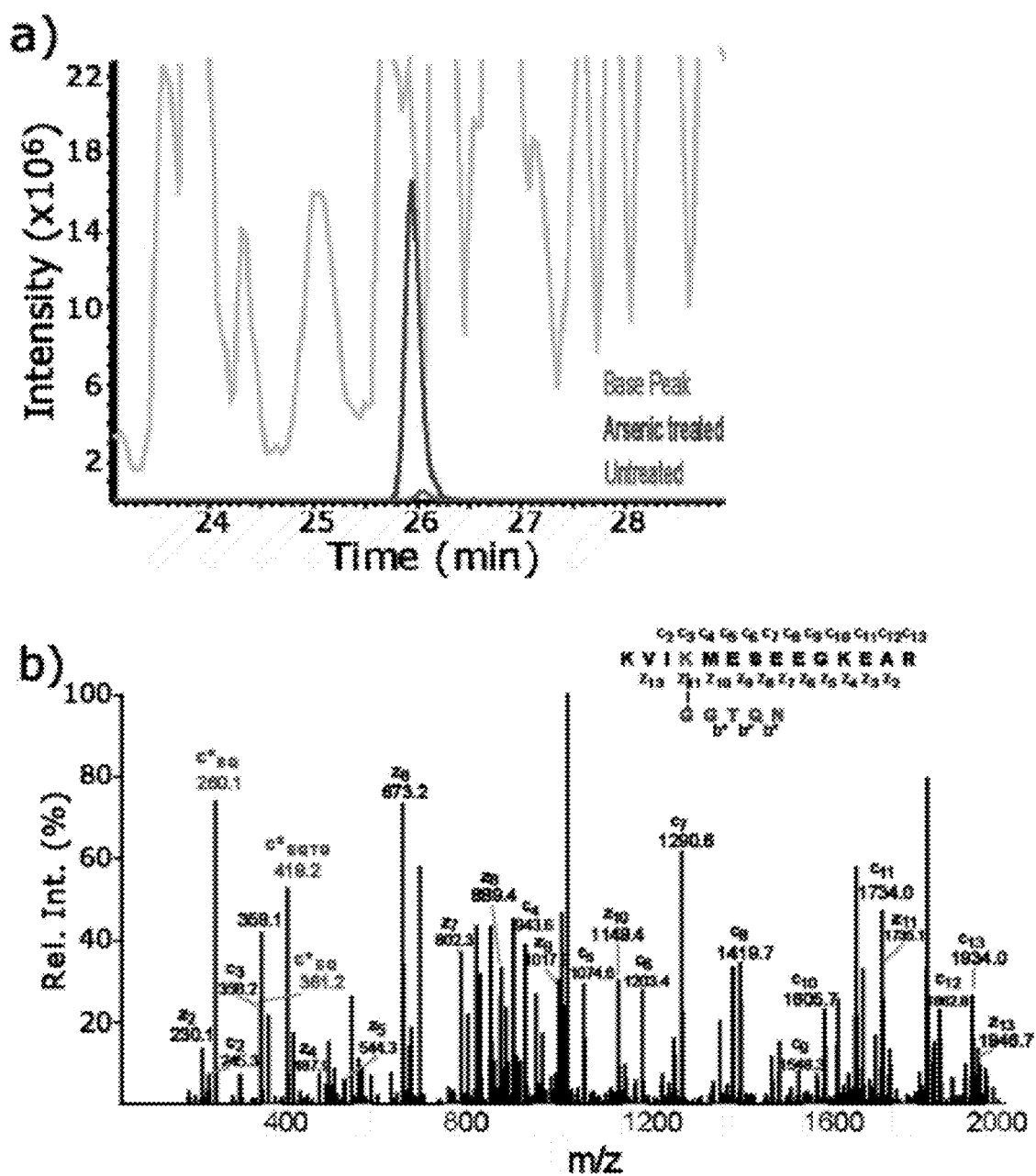
FIG. 22 illustrates a LC-MS/MS analysis of tryptic peptides from NTA-enriched SUMOylated proteins (His-SUMO3 mutant) following stimulation of HEK293 with $As_2O_3$. a) Total ion chromatogram and extracted ion chromatogram for m/z 697.73+, b) ETD MS/MS spectrum of m/z from PML showing K490 modified residue.

The affinity chromatography used in steps c) and g) is an NTA column to enrich His-tag SUMO substrates. Other affinity media could be using if SUMO constructs include other suitable moieties such as FLAG or HA tags and the like. The purpose of this method is to identify either E3 ligase and/or conditions having a direct effect on the SUMOylation of putative SUMO substrates. This is performed by comparing the abundance of SUMOylated peptides with and without cell perturbation (e.g. knock down by shRNA, environmental conditions: $As_2O_3$, interferon-gamma and the like) using mass spectrometry. The quantitative profile of each SUMOylated peptide enables a direct measurement of the change in SUMOylation in response to cell perturbations, such as cell stimuli or culture conditions. While specific substrates can be monitored directly by mass spectrometry, dot blots with SUMO-stub specific antibodies can also allow global monitoring of changes in protein SUMOylation, as illustrated in FIGS. 21 and 22.

Similarly, another method involves monitoring disease or misregulation progression and comprises a) providing either i) plasmid vectors encoding first mutated SUMO polypeptides or ii) first purified mutated SUMO polypeptides; b) culturing a first cell line expressing mutated SUMO polypeptides to produce a reference sample comprising a first plurality of SUMOylated protein substrates; c) enriching first SUMOylated protein substrates with affinity chromatography; d) digesting the first SUMOylated protein substrates with trypsin to provide first SUMOylated tryptic fragments; e) enriching the first SUMOylated fragments with antibody that specifically binds to SUMOylated moiety to provide a first reference sample that can be profiled by mass spectrometry; f) culturing a second cell line expressing mutated SUMO polypeptides in the presence of a therapeutic agent to produce a second plurality of SUMOylated protein substrates; g) enriching the second SUMOylated protein substrates using affinity chromatography; h) digesting the second SUMOylated protein substrates with trypsin to provide second SUMOylated tryptic fragments; i) enriching the second SUMOylated fragments with antibody that specifically binds to SUMOylated moiety to provide a second reference sample that can be profiled by mass spectrometry; and j) comparing the first reference profile from e) with the second reference profile from i) so as to monitor the effect the therapeutic agent has on the disease or misregulation progression.

This application is similar to that described above, except that it would involve a therapeutic agent. For example, if a tumor suppressor is misregulated during the progression of cancer through changes in its protein SUMOylation, different drugs candidates can be screened by mass spectrometry based on their ability to restore the normal pattern in protein SUMOylation. This method is particularly useful for diagnosis, prognosis or for predicting the response to treatment.

Also, another method can be used to identify inhibitors, activators or modulators of SUMO E2 conjugating enzymes, SUMO E3 ligases or SUMO proteases. This method comprises: a) providing either i) plasmid vectors encoding first mutated SUMO polypeptides or ii) first purified mutated SUMO polypeptides; b) culturing a first cell line expressing mutated SUMO polypeptides to produce a reference sample comprising a first plurality of SUMOylated protein substrates; c) enriching first SUMOylated protein substrates with affinity chromatography; d) digesting the first SUMOylated protein substrates with trypsin to provide first SUMOylated tryptic fragments; e) enriching the first SUMOylated fragments with antibody that specifically binds to SUMOylated moiety to provide a first reference sample that can be profiled by mass spectrometry; f) culturing a second cell line expressing mutated SUMO polypeptides in the presence of inhibitors, activators or modulators of SUMO E2 conjugating enzymes, SUMO E3 ligases or SUMO proteases to produce a second plurality of SUMOylated protein substrates; g) enriching the second SUMOylated protein substrates using affinity chromatography; h) digesting the second SUMOylated protein substrates with trypsin to provide second SUMOylated tryptic fragments; i) enriching the second SUMOylated fragments with antibody that specifically binds to SUMOylated moiety to provide a second reference sample that can be profiled by mass spectrometry; and j) comparing the first reference profile from e) with the second reference profile from i) so as to identify inhibitors, activators or modulators of SUMO E2 conjugating enzymes, SUMO E3 ligases or SUMO proteases.

In any of the above methods, the expression of protein substrates having SUMOylation sites require a cell line that is capable of expressing the mutant SUMO. This can be done by transfecting the mutant constructs into mammalian cells or generating cell lines that stably express the mutant SUMO. Once the cell lines are established, monitoring whether an agent and/or conditions have an effect on the SUMOylation patterns of the protein substrates requires that one imparts change a change in the SUMOylation patterns of the proteins substrates using, for example, pharmacological inhibitors, RNAi towards E3-ligase or other potential protein targets. This will provide two cell extracts (control and perturbation) from which one can enrich SUMO tryptic peptides, and compare the relative abundance using mass spectrometry. Thus, step b) above can be used with the following step: incubating a first mutated polypeptide to produce a reference sample comprising a first plurality of SUMOylated protein substrates. Also, step f) above, can be used with the following step: incubating a second mutated SUMO polypeptide. The methods can be used in vivo or in vitro. For in vitro use, the method may involve incubating SUMO modifying enzymes with potential protein substrates, i.e. one substrate at a time, whereas in vivo may be used with cell lines where all the putative substrates would be effected by the cellular perturbation.

An additional aspect of the discovery that is contemplated is the use of a solid support for identifying a SUMO mutation in a subject or a biological sample derived from the subject. The solid support comprises a probe for identifying a nucleic acid molecule, as described herein. The nucleic acid probe is used for the specific identification of a SUMO mutation in a subject. The nucleic acid probe is one that comprises a sequence which anneals with or specifically hybridizing to a nucleic acid molecule of as described herein.

EXAMPLES

Mutant SUMO isoforms were developed and characterized to facilitate the identification and quantitation of protein SUMOylation in mammalian cells. Protein SUMOylation is a highly dynamic modification regulated by a complex network of SUMO-activating enzyme (SAE1/SAE2), conjugating enzymes (Ubc9) and SUMO-E3 ligases (PIAS1, PIAS3, PIASxα, PIASxβ, PIASy, RanBP2 and Pc2) for the transfer of SUMO isoforms to specific protein substrates (Kim, K. I., and Baek, S. H. (2006). SUMOylation code in cancer development and metastasis. Molecules and cells 22, 247-253; Guo, B., Yang, S. H., Witty, J., and Sharrocks, A. D. (2007). Signalling pathways and the regulation of SUMO modification. Biochemical Society transactions 35, 1414-1418).

The dynamic changes in protein SUMOylation in reponse to different cell stimuli is counter balanced by SUMO-specific proteases (SUSP's or SENPs) cleaving this modification on specific SUMO substrates (FIG. 1). Gene constructs of SUMO isoforms were engineered to include a His6 affinity tag (SEQ ID NO: 31) and a mutated amino acid at position 5 from the C-terminus of the expressed protein (FIG. 2).

A—Molecular Biology

In a human cell, SUMO proteins are translated from 3 genes: SUMO1, SUMO2 and SUMO3. To facilitate the identification of SUMOylated protein substrates by mass spectrometry, cDNA mutants were generated from each of the SUMO isoforms. The cDNA sequences of the wild type and mutant sequences together with their translated protein products are presented in FIG. 2. The mutant SUMO cDNA isoforms comprise a N-terminus His6x (SEQ ID NO: 31) tag along with a site mutation at the C-terminus that incorporates a convenient Arg residue for subsequent cleavage by trypsin.
1) Generation of Expression Vectors:

SUMO wild type and mutants expression vectors were generated by site-directed mutagenesis of SUMO isoforms from plasmids (M. Chelbi-Alix) within the SUMO1, SUMO2, SUMO3 cDNA (pCNA3.0-His6X-SUMO1, pCDNA3.0-His6X-SUMO2 and pCDNA3-His6X-SUMO3). We amplified SUMO cDNA by high fidelity PCR with primer forward with the restriction sites Kpn I, NcoI, start codon and primers reverses with STOP codon and XhoI restriction site. (Table 1).

TABLE 1

Primer sequences

Primer forward:

| | | |
|---|---|---|
| | 5'gacccaagcttggtaccatggctcatc 3' | (SEQ ID NO: 15) |

Primers reverse:

| | | |
|---|---|---|
| SUMO1 WT | 5'ctaccgctcgagttaaccccccgtttgttcctgataaacttc 3' | (SEQ ID NO: 16) |
| SUMO1 mutant | 5'ctaccgctcgagttaaccccccgtttgttcccgataaacttc 3' | (SEQ ID NO: 17) |
| SUMO2 WT | 5'ctaccgctcgagttaacctcccgtctgctgttggaacacatc 3' | (SEQ ID NO: 18) |
| SUMO2 mutant | 5'ctaccgctcgagttaacctcccgtctgctgtcggaacacatc 3' | (SEQ ID NO: 19) |
| SUMO3 WT | 5'ctaccgctcgagttaacctcccgtctgctgctggaacacgtc 3' | (SEQ ID NO: 20) |
| SUMO3 mutant | 5'ctaccgctcgagttaacctcccgtctggttccggaacacgtc 3' | (SEQ ID NO: 21) |

Figure 3:
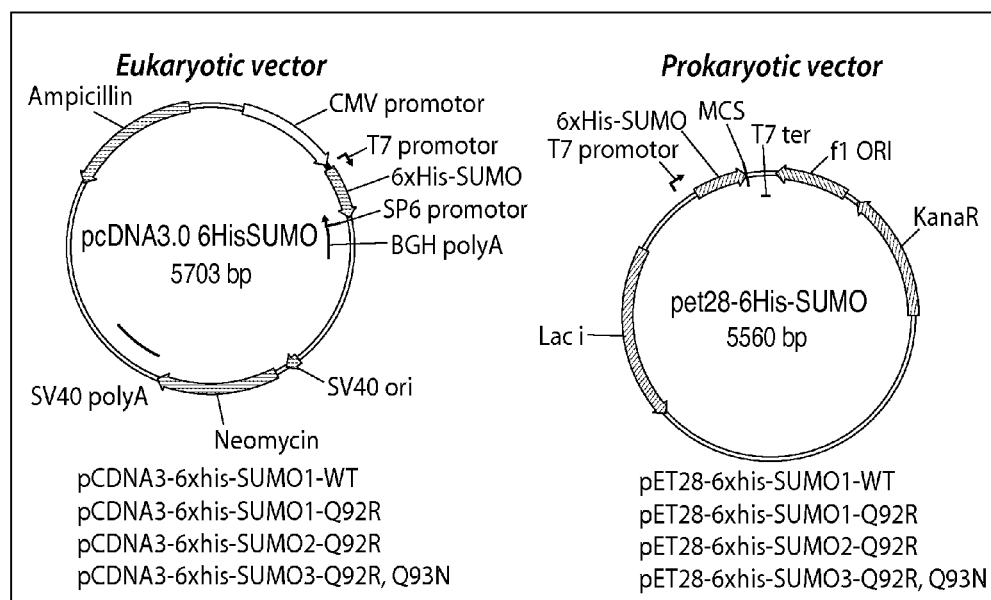
FIG. 3 is a map of eukaryotic and prokaryotic expression vectors.

To generate prokaryotic expression vectors (pET28-His6-SUMO1 WT, pET28-His6-SUMO1 mutant, pET28-His6-SUMO2 WT, pET28-His6-SUMO2 mutant, pET28-His6-SUMO3 WT, pET28-His6-SUMO3 mutant), we ligated the digested NcoI/XhoI PCR product with the digested NcoI/XhoI pET28b vector (FIG. 3).

Figure 4:
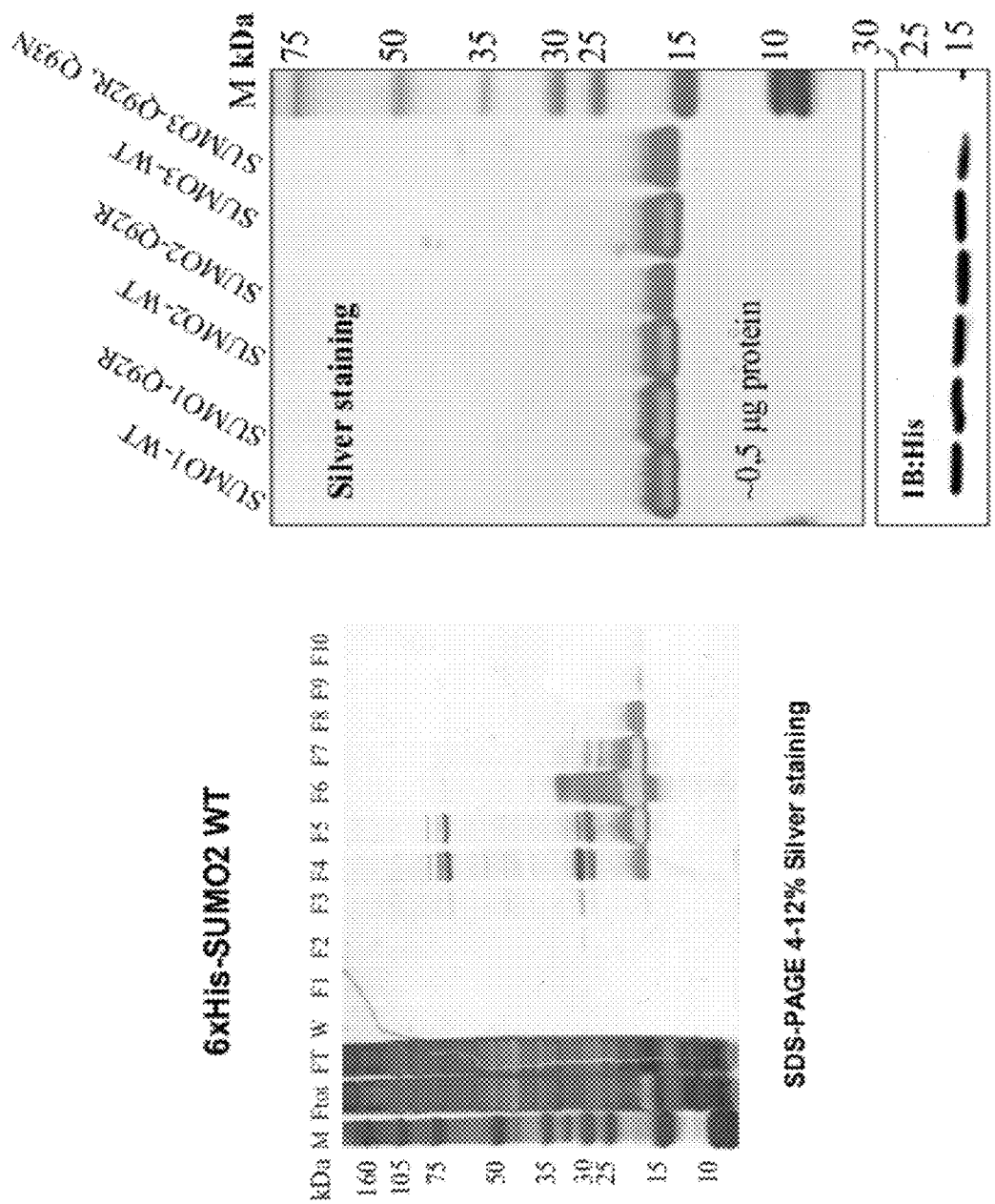
FIG. 4 illustrates SDS-PAGE samples of (A) His6-SUMO2 purification on NTA column, (B) His6-SUMO wild type and mutant proteins are visualized after silver staining and western-blot with the anti-His antibody.

The eukaryotic expression vectors (pCDNA3-His6-SUMO1 WT, pCDNA3-His6-SUMO1 mutant, pCDNA3-His6-SUMO2 WT, pCDNA3-His6-SUMO2 mutant, pCDNA3-His6-SUMO3 WT, pCDNA3-His6-SUMO3 mutant) were obtained following ligation of the digested KpnI/XhoI PCR product with the digested KpnI/XhoI pcDNA3 vector (FIG. 3).
2) His6-SUMO Recombinants Proteins Production and Purification:

E. Coli BL21(DE3) cells transformed with pET28-His6-SUMO expressing all His6-SUMO forms were grown overnight at 37° C. in Luria Broth (LB) broth. Overnight cultures were diluted 100-fold into LB supplemented with 25 μg/mL of kanamycin and grown at 37° C. to 0.5 DO at 600 nm, then induced with isopropylthiogalactoside (IPTG) at final concentration of 1 mM. Cells were harvested after 5 hours and lysed twice in liquid nitrogen and 37° C. bath followed by sonication in a buffer containing 20 mM phosphate pH 7.6, 500 mM NaCl and 30 mM imidazole. Cell debris was removed by centrifugation at 16 000 g for 20 minutes and the filtered supernatant was loaded in 5 mL Ni$^{2+}$-NTA HiTrap Chelating HP column (GE Healthcare). The column was washed according to the manufacturer instructions, followed by an imidazole gradient 50 mM-500 mM. The different fractions were separated by SDS-PAGE and visualized by silver staining (FIG. 4A). His6-SUMO recombinant proteins eluted in 200-300 mM imidazole (Fractions 5-7) and were subsequently concentrated using a Centricon 30 kDa cut-off membrane (Millipore). The eluates containing the recombinant His6-SUMO proteins was collected and pf frozen at −80° C. with 5% glycerol (FIG. 4B).

3) Stable Cell Lines Expressing SUMO Mutants

HEK293T cells were grown in Dulbecco's modified Eagle medium supplemented with 10% fetal bovine serum, 50 U of penicillin and 50 μg/mL of streptomycin sulphate at 37° C. in 5% $CO_2$. Cells were transfected using calcium phosphate precipitation with pCDNA3-His6-SUMO plasmids. 48 h after transfection, G418 antibiotic was added at 500 μg/mL. After a week of selection, we cloned the resistant cells to obtain a clone G418 resistant and which over-express His-SUMO protein. The expression was tested by His-SUMO pull down and immunoblots anti-His.
B—In Vitro SUMOylation Assay To confirm the viability and functionality of the mutant SUMO isoforms, in vitro conjugation assay were evaluated with known SUMO substrates such as RanGAP and E2 ligase. In each case, the SUMOylated protein products were analyzed by mass spectrometry to identify the site of SUMOylation.
1) Development of a SUMOylation In Vitro Assay Protein SUMOylation involves a three steps conjugation as shown in FIG. 6.

For in vitro SUMOylation, the reaction mixture comprised 20 μL of reaction buffer (20 mM $NH_4CO_3$ pH 9, 20 mM NaCl, 0.5 mM DTT), 1 μg recombinant and purified SUMO proteins, 0.5 μg of substrate E2-25K (Boston Biochem) or RanGAP fragment (Boston Biochem), 0.1 μg SASE1/SAE2 heterodimer (Boston Biochem), 0.5 μg conjugating enzyme hUbC9 (Boston Biochem) with or without Mg-ATP solution (Boston Biochem) at 5 mM. The reaction mixture was incubated at 37° C. for 1 hour and subsequently stopped by adding an equal volume of Laemmli Buffer. The reaction mixture was analysed separated by SDS-PAGE and visualized using Western Blotting (2 μl), coomassie staining (10 μL) or silver staining (5 μL) as shown in FIGS. 7 and 8.
SDS-PAGE Separation:

Protein extracts were subjected to electrophoresis through a 4-12% NuPAGE Bis-Tris polyacrylamide gel (Invitrogen, Burlington, ON, Canada) under denaturing conditions. After electrophoresis, proteins were fixed within the polyacrylamide gel by incubating the entire gel in 5% (v/v) acetic acid in a 1:1 (v/v) water:ethanol solution. For silver staining, the gel was first sensitized for 1 minute using an aqueous solution of 0.02% sodium thiosulfate ($Na_2S_2O_3$) unless otherwise indicated. Staining was performed by incubating the gel in 0.1% (v/v) silver nitrate ($AgNO_3$) in water for 25 minutes at 4° C. Finally, the gel was developed in 3% (w/v) sodium carbonate ($Na_2CO_3$, pH: 11.4) containing 0.05% formalin (v/v) in water. The staining was then stopped with a solution of 5% (v/v) acetic acid in water. For Coomassie blue staining, proteins were fixed after gel separation and stained in a one-step procedure by incubating the entire gel in 0.1% (w/v) Coomassie Brilliant Blue R-250 in a 1:8:11 (v/v/v) acetic acid: methanol:water mixture for 1 hour at room temperature (RT). The gel was finally rinsed three times in a 1:4:5 (v/v/v) acetic acid:methanol:water solution at RT to visualize protein bands.

Destaining and in-Gel Digestion—

Protein bands were excised from the gel and destained in 200 µl of destaining solution composed of 30 mM potassium hexacyanoferrate (III) ($K_3Fe(CN)_6$) and 100 mM sodium thiosulfate ($Na_2S_2O_3$) in a 1:1 ratio for all silver stained gel bands. For Coomassie blue stained gels, the destaining process was performed by incubating the gel pieces in 200 µl of a 1:1 (v/v) water:MeCN solution. Proteins were then reduced with 10 mM DTT in 50 mM ammonium bicarbonate ($NH_4HCO_3$) pH 8.5 at 56° C. for 1 hour and alkylated using 55 mM iodoacetamide in 50 mM ammonium bicarbonate pH 8.0 at RT for 1 hour in the dark. Proteins were digested overnight with trypsin (Promega, sequencing grade, 10 ng/µL) in 50 mM ammonium bicarbonate pH 8.0 at 37° C. Peptides were extracted with 5% (v/v) trifluoroacetic acid (TFA) in a 1:1 (v/v) water:MeCN mixture. Following evaporation to dryness, peptides were resuspended in 30 µL of 0.2% formic acid (FA) in water and analyzed by mass spectrometry.

2) Mass Spectrometry Analyses of In Vitro SUMOylation Products

Suspected SUMOylated protein bands detected from silver stained gels were excised, in-gel digested and analyzed by mass spectrometry (MS). All MS analyses were performed using an LTQ-Orbitrap hybrid mass spectrometer with a nanoelectrospray ion source (ThermoElectron, San Jose, Calif.) coupled to a nano-flow LC system (Eksigent, Dublin) equipped with a Finnigan AS autosampler (Thermo Electron, San Jose, Calif.). Protein digests were separated using a 10 cm length, 150 µm i.d. analytical column and a 4 mm length, 360 µm i.d. trap column packed in-house with 3 µm $C_{18}$ particles (Jupiter 300 Å, Phenomenex, Torrance, Calif.). The mobile phase consisted of 0.2% FA in water (solvent A) and 0.2% FA in MeCN (Solvent B). The pump flow rate was set to 0.6 µL/min and peptide elution was achieved using a linear gradient of 5 to 40% B for the first 53 min followed by a rapid increase to 60% B for the next 3 min. The conventional MS spectra (survey scan) were acquired at high resolution (M/ΔM: 60,000 full width half maximum) over the acquisition range of m/z 400-1600. Full scan tandem mass ($MS^2$) spectra were analyzed in the linear trap using either collision induced dissociation (CID) or electron transfer dissociation (ETD). For ETD spectra fluoranthene anions were produced from a chemical ionization source and introduced to the ion trap prior to reaction with the selected precursor ions. Peptides were analyzed in data-dependent mode where, for each 1 s survey scan, the 3 most intense precursor ions with intensity above 10,000 counts were selected for $MS^2$ sequencing with a total duty cycle of 2.5 s. In order to prevent the reacquisition of product ion spectra from a same precursor ion, a dynamic exclusion window of 0.5 Da was applied for 90 s. Mass calibration used either an internal lock mass (protonated $(Si(CH_3)_2O))_6$; m/z 445.12057) or external calibration using Calmix (caffeine, MRFA, and ultramark) and typically provided mass accuracy within 5 ppm for all nanoLC-MS experiments.

Figure 10:
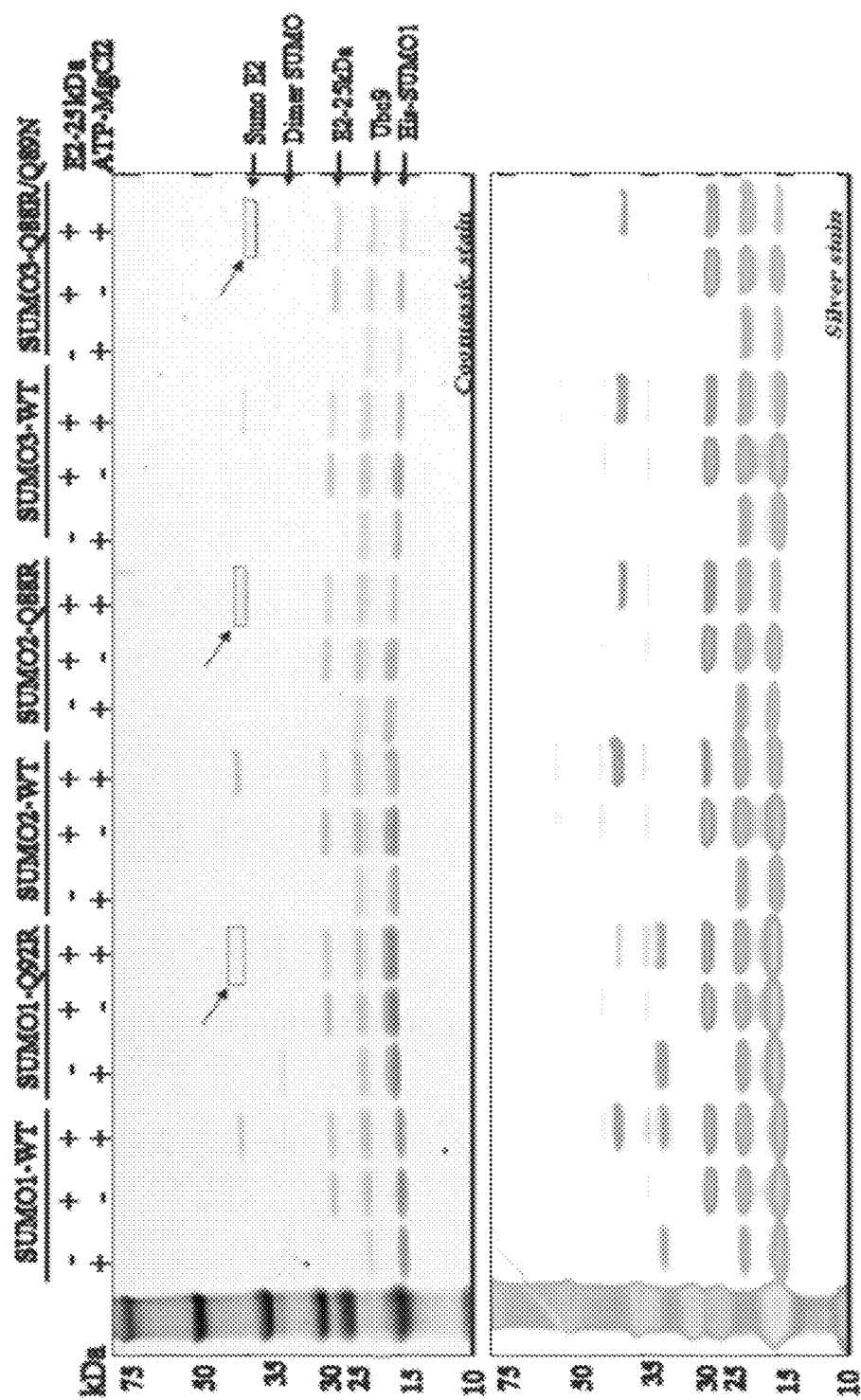
FIG. 10 illustrates Coomassie and silver stained gels of in vitro SUMOylation assay using Ubiquitin-conjugating enzyme E2 as protein substrate. Gel lanes are shown for different recombinant His6-SUMO1 (wild type and mutant Q92R), His6-SUMO2 (wild type and mutant Q88R), and His6-SUMO3 (wild type and mutant Q92R/Q93N). In each case the SUMOylated E2 is observed as the highest molecular weight band. Dash boxes indicate band excised and in-gel digested with trypsin prior to MS analysis, as illustrated in FIG. 12.
Figure 11:
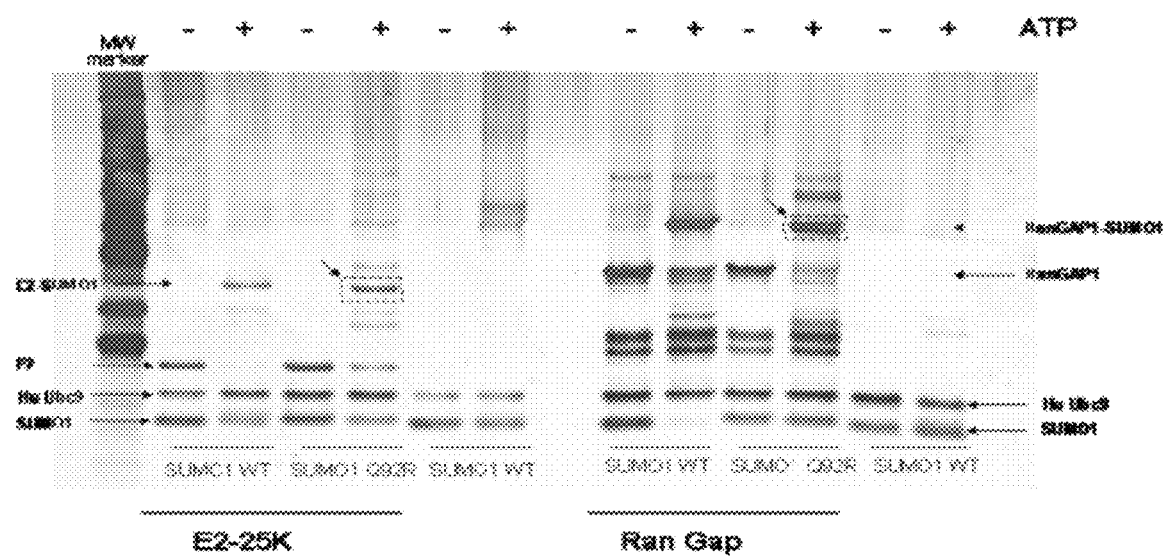
FIG. 11 illustrates silver-stained gel of in vitro SUMOylation assay using E2-ligase and RanGAP1 as protein substrate with and without activating ATP. Bands excised for mass spectrometry analyses, as illustrated in FIG. 13, are identified by the dash boxes.
Figure 13B:
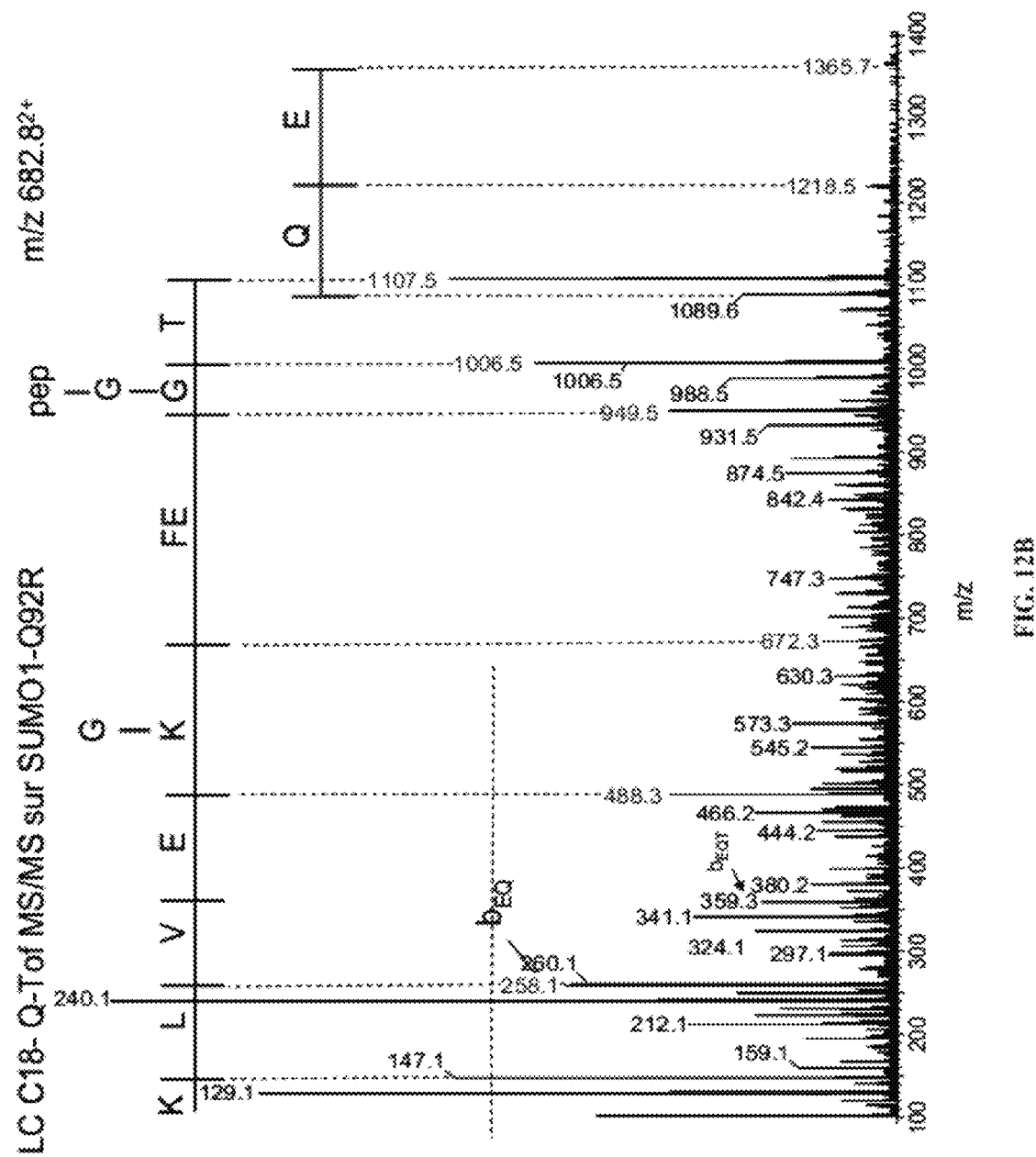
FIGS. 13A and 13B disclose "EQTG" as SEQ ID NO: 33.

For example, tandem mass spectra are prevented for SUMOylation E2-ligase using collision-induced disassociation (FIG. 12) allowing the identification of SUMOylation sites on each of the mutant isoforms conjugated to E2-ligase from band excised in FIG. 10. The tandem mass spectra of E2-ligase and RanGAP substrates (from band excised in FIG. 11) conjugated with SUMO1 obtained using ETD are presented in FIG. 13. The use of ETD simplifies the interpretation of fragment ions observed in the tandem mass spectrum compared to their corresponding CID spectra (FIG. 12 top panel).

C—Sumoylation In Vivo Assay

1) In Vivo Assay on HA Tag of RanGAP1 Protein by Immunoblotting

An assay was developed to confirm in vivo SUMOylation of protein with the eukaryote construct bearing the mutation. RanGap1 was transfected in HEK293T cells (FIG. 10).

2) In Vivo Assay on PML Protein by Immunofluorescence Microscopy and by Denaturated his-SUMO Pull Down The functional activity of the wild type and SUMO mutants was also determined from immunofluorescence microscopy by monitoring the recruitment of the SUMOylated promyelocytic leukaemia (PML) substrate to nuclear bodies following treatment of HEK293 cells with $As_2O_3$ (FIG. 14). The visualization of all SUMO mutants using this immunofluorescence assay also confirmed the functional activity of all three SUMO isoforms (FIG. 15).

Comparison of His-SUMO pull down assays (Jaffray and Hay, Methods, 38, 35, 2006) on HEK293T cells co-transfected with PML III isoform cDNA along with each wild type or mutant SUMO cDNAs indicated comparable protein recovery yields confirming that mutant and wild type form behave similarly. Also SUMO mutant isoforms provided comparable recovery yields during His-SUMO pull down assay when HEK293 cell cultures were incubated with $As_2O_3$ (FIG. 16).

D—Sumoylated Protein Purification and SUMO1 Conjugated Peptide Enrichment

Figure 17:
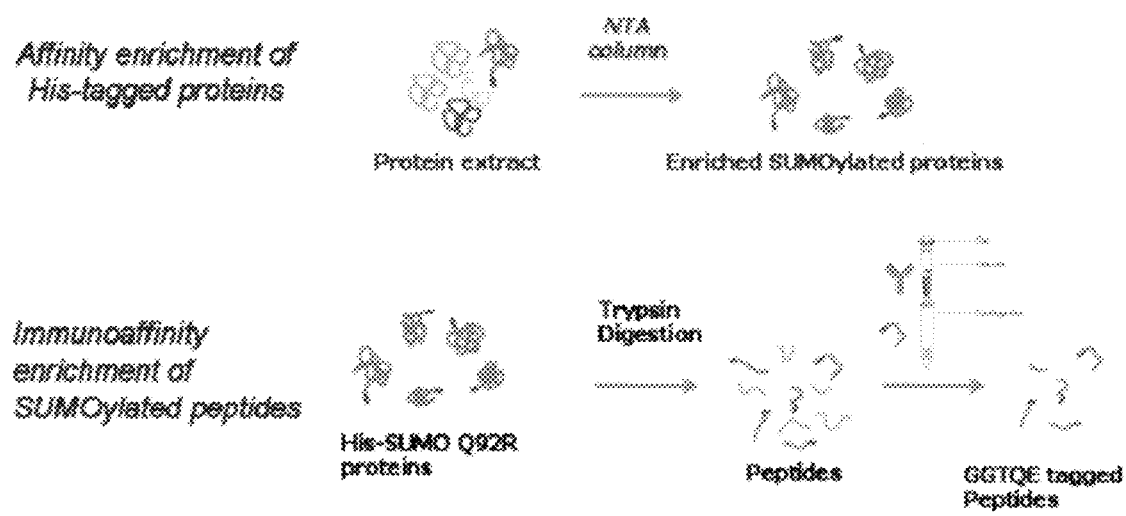
FIG. 17 is a diagram showing a dual affinity approach using SUMO isoforms comprising a His-tag at the N-terminus and mutations near the end of the C-terminus of the expressed protein. The latter mutations introduce an arginine residue near the C-terminus and do not compromise the function of the respective SUMO isoforms. The His-tag segment is used for affinity purification on nickel-agarose immobilized metal affinity chromatography media, NTA column (top). The arginine residue at the C-terminus is strategically located to favour the release of a short amino acid segment covalently attached to the lysine of SUMOylated protein targets once digested with trypsin. Purification of corresponding tryptic peptides with this short amino acid sequence is achieved using either polyclonal or monoclonal antibody reagents (bottom).

An enrichment method was developed to facilitate the isolation of peptides bearing SUMOylation sites. This was achieved using a two pronged affinity approach. First, a Nickel-loaded agarose beads (NTA) is used to enrich $His_6$-SUMO1 sumoylated proteins (FIG. 17 top). Enriched His6-SUMO proteins are subsequently digested with trypsin to expose a EQTGG (SEQ ID NO: 34) (SUMO1) side chain on a modified lysine that is recognized by a specific rabbit polyclonal antibody (Custom antibody from Genscript). The polyclonal antibodies were raised against the epitope GGTQE (SEQ ID NO: 32) from SUMO1 mutant obtained by conjugating the synthetic peptide FK{GGTQE}VELC to Keyhole Limpet Hemocyanin (KLH) carrier protein via the Cys residue (FIG. 17 bottom). Similarly, polyclonal antibodies were generated for each SUMO mutant and provided a convenient immunoaffinity approach to isolate all SUMO isoforms. A specific combination of amino acid residues unique to each SUMO isoform identifies the nature of the SUMO modification at the relevant lysine residue with characteristic reporter ions when analyzed by mass spectrometry (FIG. 5).

1) Enrichment of SUMOylated Peptide for Mass Spectrometry Analyses

Figure 18:
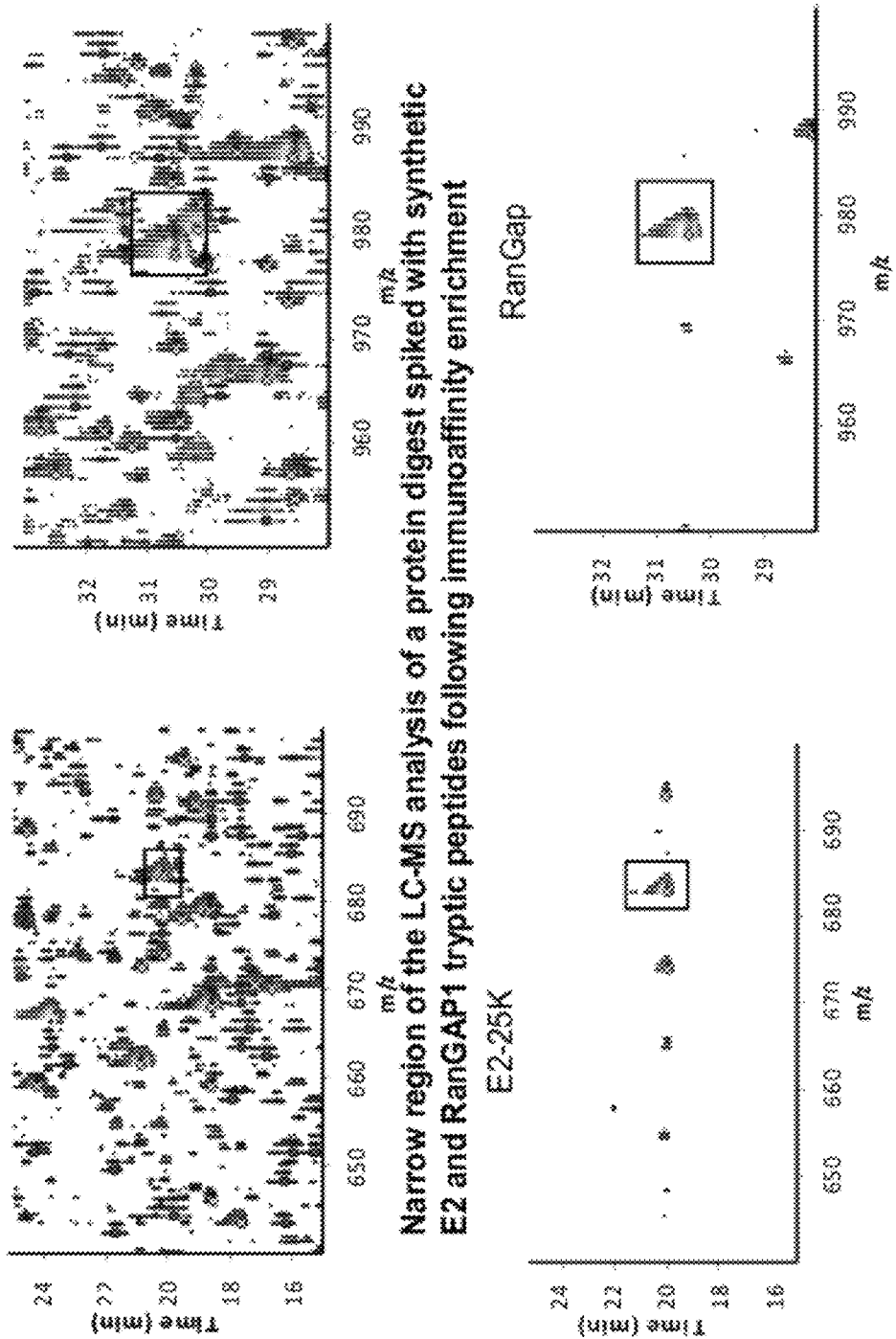
FIG. 18 illustrates LC-MS analysis of synthetic SUMO peptides with (bottom) and without (top) immunoaffinity purification with polyclonal antibodies. A total of 50 pmoles of synthetic E-2 ligase and RanGAP1 SUMO peptides were spiked into 9 μg of protein tryptic digest (bovine serum albumin, bovine glutamate dehydrogenase, rabbit aldolase, yeast alcohol dehydrogenase, bovine catalase, human lactotransferrin, E. coli glycerokinase, and bovine lactoperoxidase).
Figure 19:
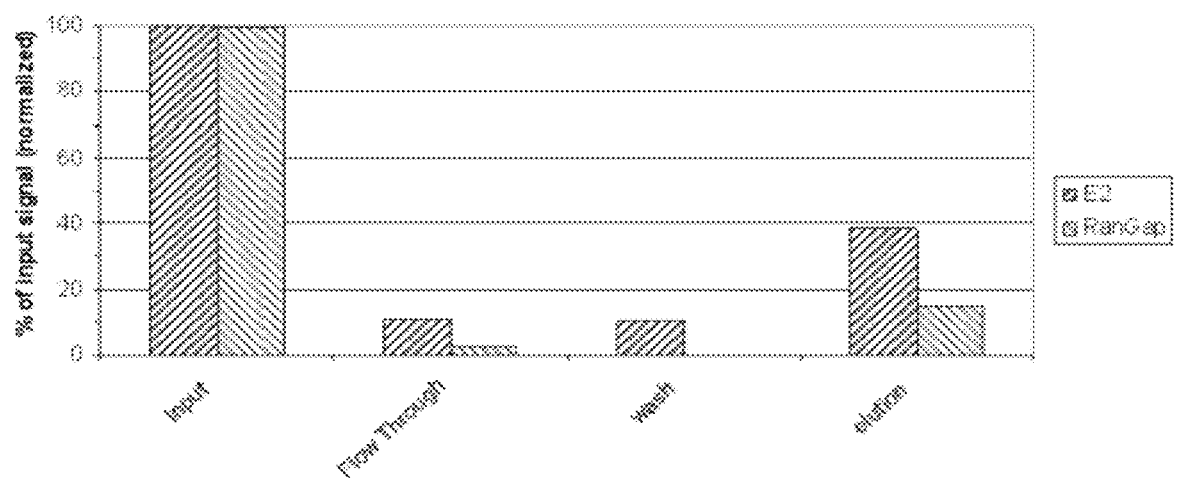
FIG. 19 is a histogram showing recovery yield of synthetic SUMO peptides with polyclonal antibodies. A total of 50 pmoles of synthetic E-2 ligase and RanGAP1 SUMO peptides were spiked into 9 μg of protein tryptic digest (bovine serum albumin, bovine glutamate dehydrogenase, rabbit aldolase, yeast alcohol dehydrogenase, bovine catalase, human lactotransferrin).

The specificity of the polyclonal antibody was evaluated with mixtures of synthetic SUMO peptides spiked into complex protein digests. Two synthetic SUMO peptides corresponding to structures identical to those found in E2-ligase and RanGAP1 were spiked at levels of 50 pmoles into 9 μg of protein digests. A comparison of the LC-MS analyses of these samples are shown in FIG. 18 for the corresponding samples with and without immunoaffinity enrichment. A narrow region of the contour profile (m/z vs time) of this analysis clearly shows the selective enrichment of these two SUMO peptides following antibody purification (FIG. 18, bottom) compared to the original protein digest sample (FIG. 18, top). FIG. 19 shows the recovery yield of synthetic SUMO peptides with polyclonal antibodies.

2) Purification of SUMOylated Proteins from Large Scale Experiments

Figure 20:
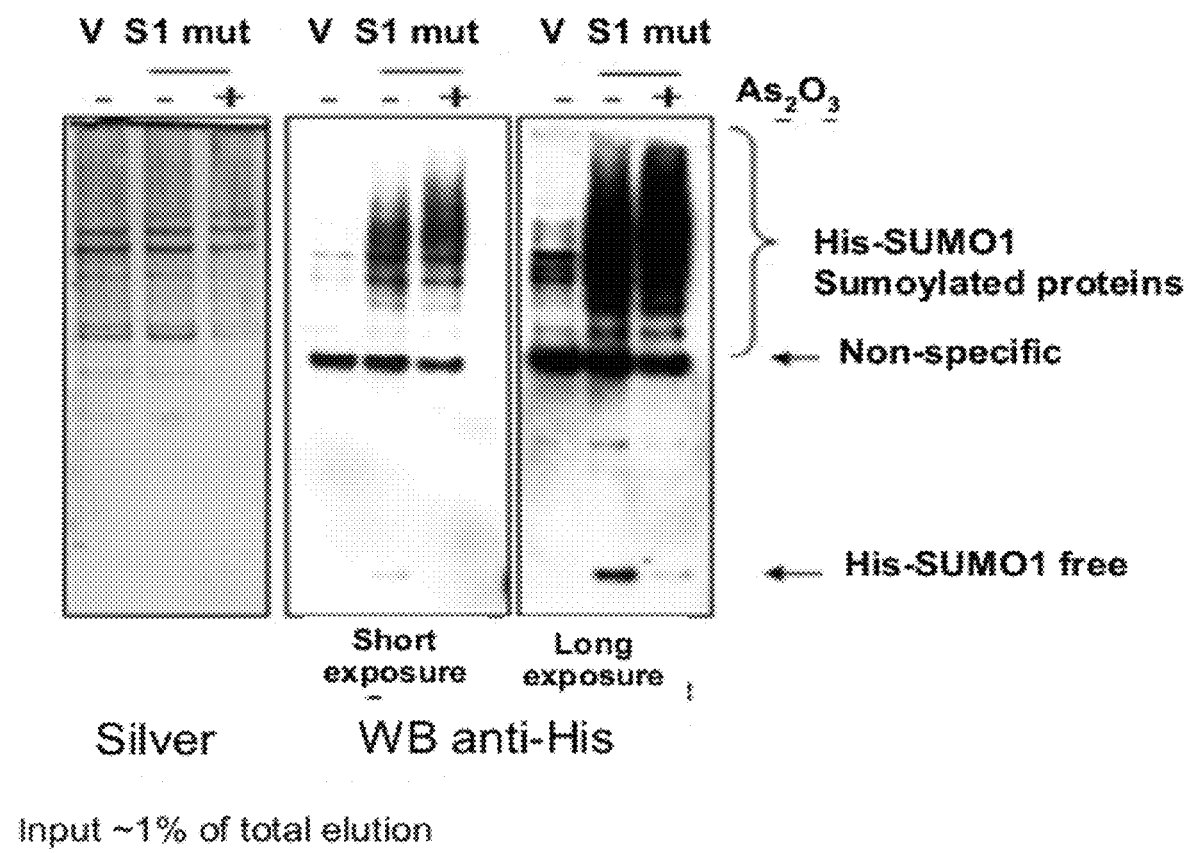
FIG. 20 illustrates gel electrophoresis separation of His6-SUMO1 mutant proteins following NTA purification. Silver-stained SDS-PAGE and immunoblot anti-His show an enrichment of His6-SUMO1 proteins as indicated from the trail of protein bands at the top of the gel. Enhanced protein SUMOylation is observed following cell stimulation with $As_2O_3$.

SUMOylated proteins were purified from $10^9$ cells of stably expressing His6-SUMO1 mutant; half of cell culture was treated with 1 μM $As_2O_3$ during 4 hours. Cells were harvested, washed with PBS and lysed with 15 mL of Buffer A (6 M guanidinium-HCl, 0.1 M NaH2PO4, 0.01 M Tris-HCl, pH 8.0, 10 mM-mercaptoethanol). The lysate was sonicated, centrifuged at 16 000 g for 30 minutes and filtered on 0.45 μm and mixed with 500 μL $Ni^{2+}$-NTA agarose beads (Invitrogen) pre-washed with lysis buffer and incubated overnight at room temperature on rotating wheel. The NTA beads were successively washed with the following solutions: buffer A, buffer B (8 M Urea, 0.1 M $NaH_2PO_4$, 0.01 M Tris-HCl, pH 6.3, 10 mM-mercaptoethanol), buffer B plus 0.2% Triton X-100, twice with buffer B. His SUMO proteins were eluted from the NTA beads using 200 mM imidazole, 0.15 M Tris-HCl, pH 6.7, 5% Glycerol. An example of the enriched His6-SUMO1 mutant proteins is shown on FIG. 20 following SDS-PAGE separation and gel visualisation using silver staining and anti-His immonublot.

As seen in FIG. 21, LC-MS/MS analyses of tryptic peptides from NTA-purified His-SUMO3 proteins of HEK293 cells treated or not with As2O3 revealed differentially SUMOylated proteins. This scatter plot compares the abundance of more than 4500 peptide ions, of which approximately 45 correspond to SUMOylated tryptic peptides (blue circles). Peptide corresponding to PML a known SUMO substrates are shown by red circles (red circles with blue outline indicate PML peptides that are SUMOylated). An example of this is shown for K490 baring peptide that showed a 8-fold increase in SUMOylation upon arsenic (As2O3) treatment. This result is consistent with previous literature on this SUMOylation site (Weisshaar, S. R. et al. Arsenic trioxide stimulates SUMO-2/3 modification leading to RNF4-dependent proteolytic targeting of PML. *FEBS letters* 582, 3174-3178 (2008)).

As seen in FIG. 22, LC-MS/MS analysis of PML K490 tryptic peptide from enriched SUMOylated proteins (SUMO3) following stimulation of HEK293 with As2O3 (from analysis shown in FIG. 21). a) Total ion chromatogram and extracted ion chromatograms for m/z 697.73+ b) ETD MS/MS spectrum of m/z from PML showing K490 modified residue. Confirmation of the SUMOylation site was obtained through the detection of characteristic fragment ions highlighted by the c* fragments together with fragment ions z11 at m/z 1735 and c4 at m/z 943.6

FIG. 23 shows examples of identified SUMOylated proteins with their modification sites.

Figure 24:
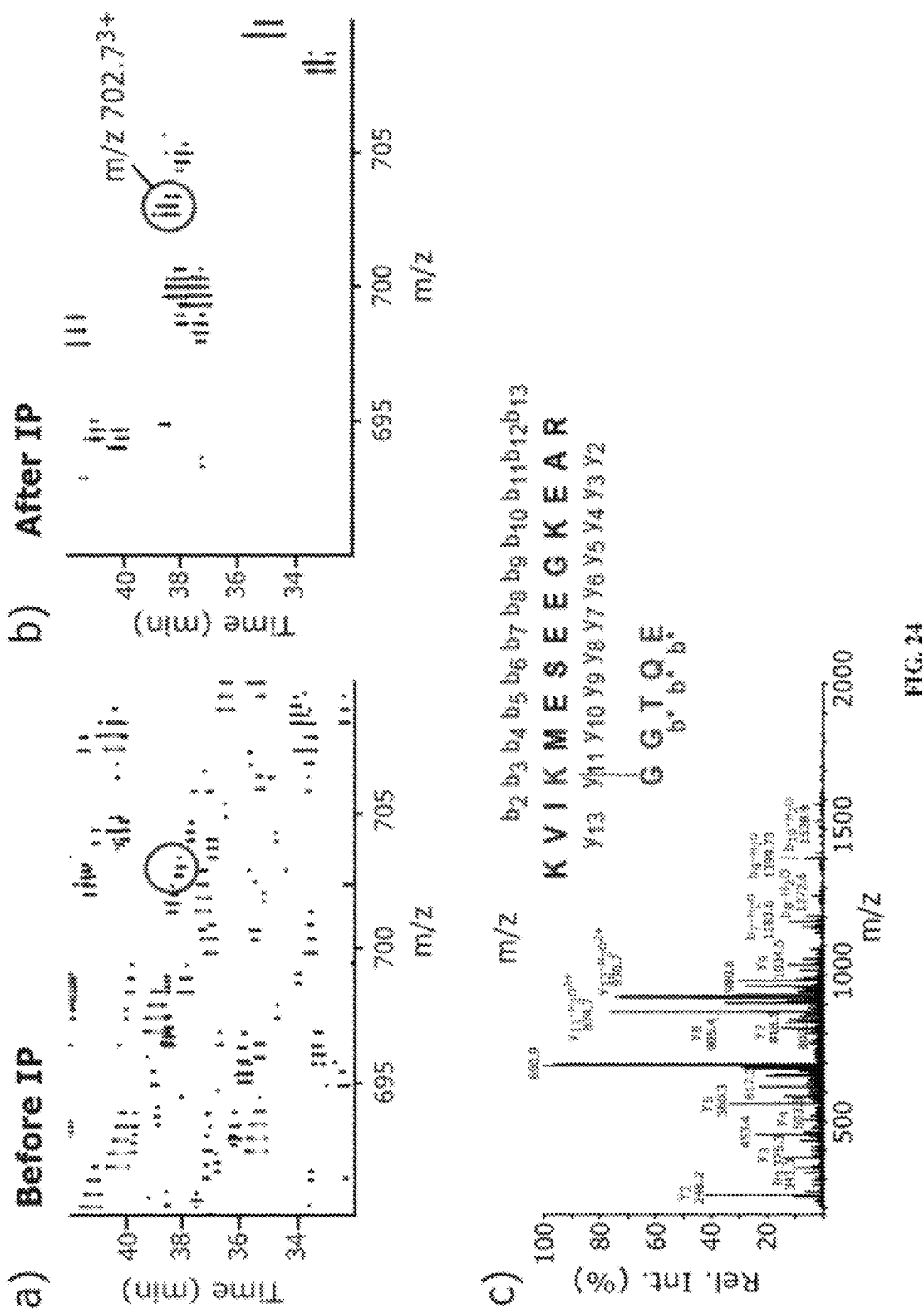
FIG. 24 illustrates a narrow contour map of tryptic digest of NTA purified HIS-SUMO1 from HEK293 (a) without and (b) with immunoaffinity purification (IP). (c) CID MS-MS of m/z $702.7^{3+}$ from PML peptide with SUMOylated K490 residue.
Figure 24A:
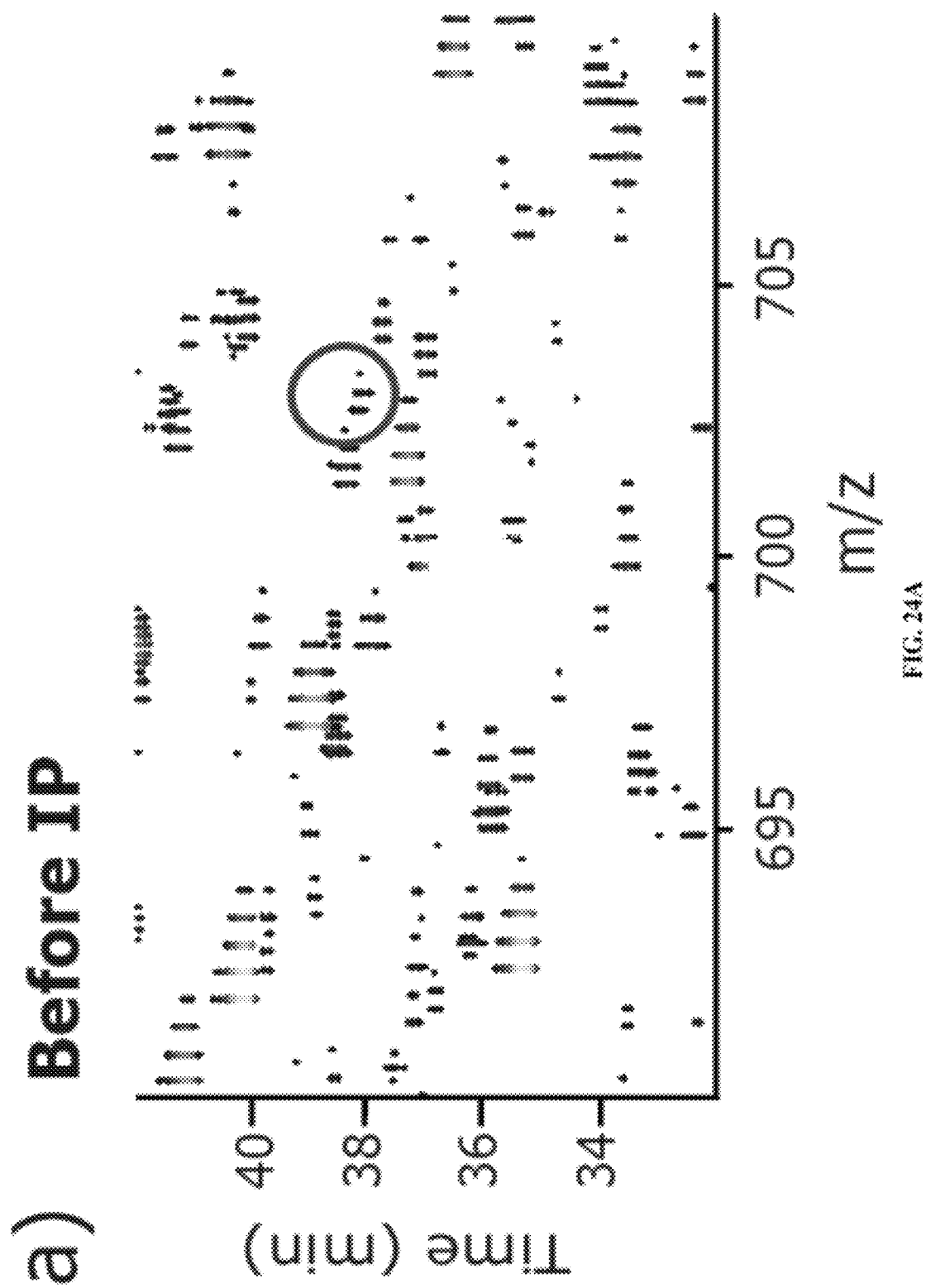
Figure 24B:
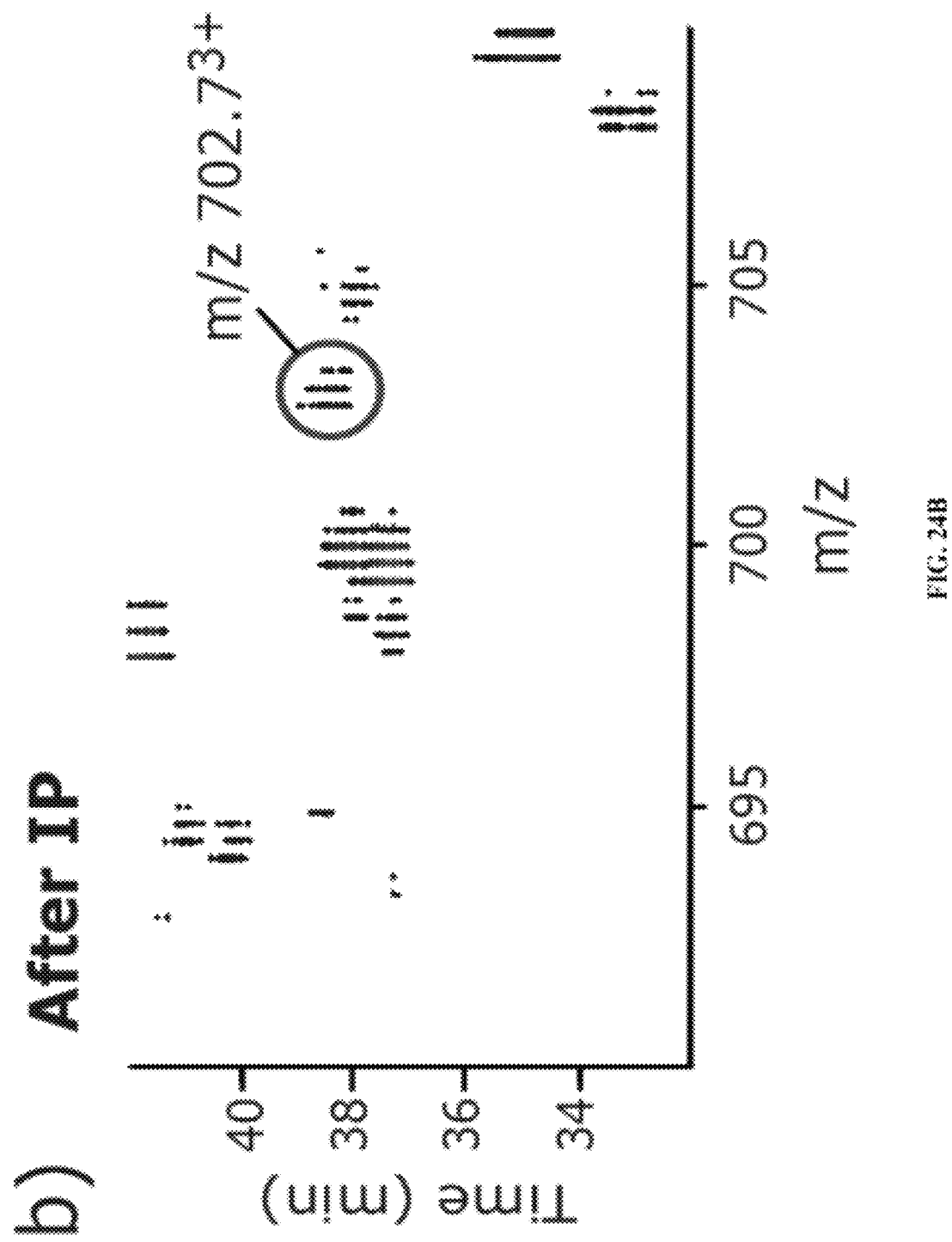
Figure 24C:
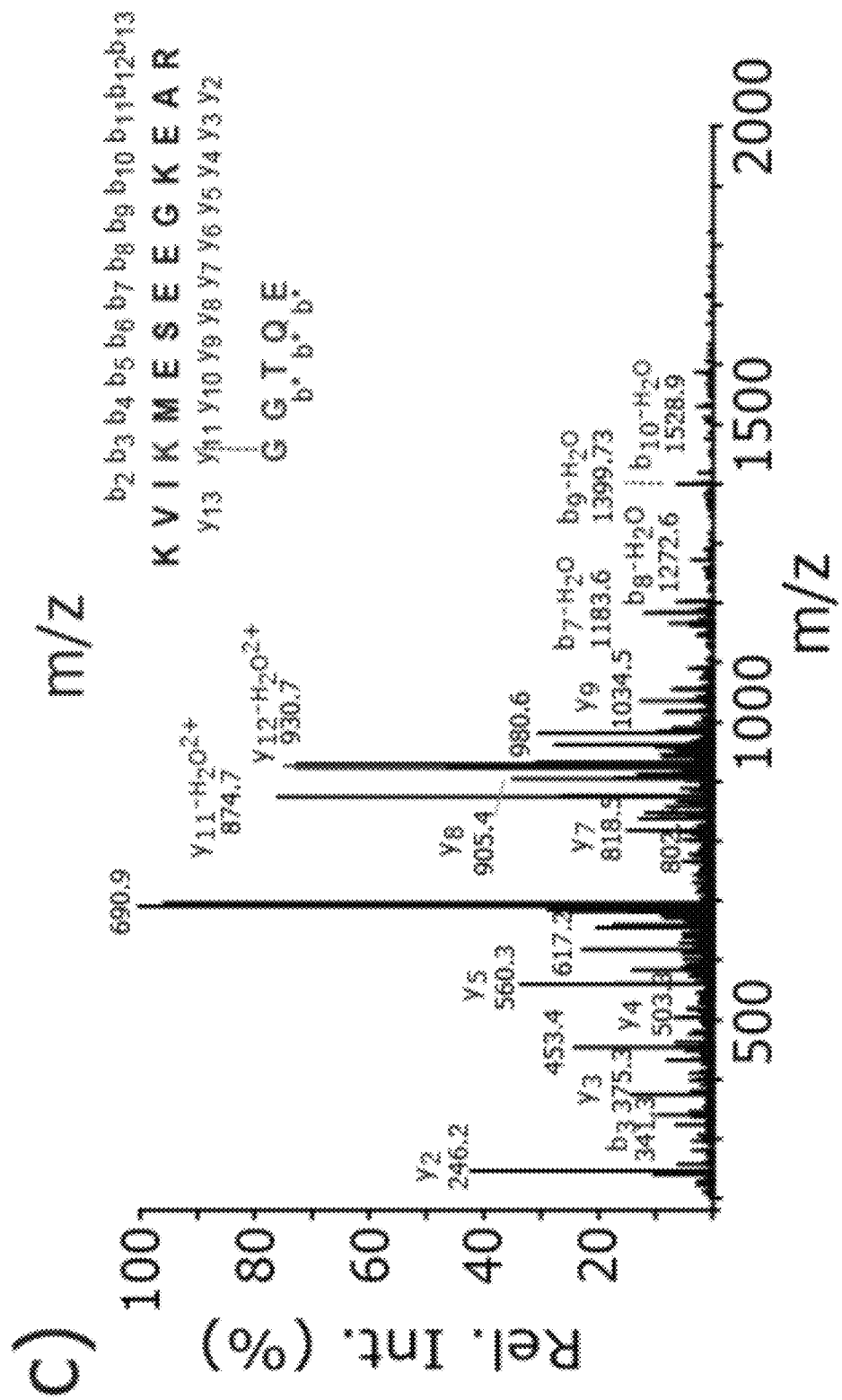

As illustrated in FIG. 24, LC-MS-MS analysis of SUMO tryptic peptides were obtained from dual affinity enrichment (ie NTA+immunoaffinity) of HEK293 SUMO1 mutant. Narrow contour map of tryptic digest of NTA purified HIS-SUMO1 from HEK293 (a) without and (b) with immunoaffinity enrichment. (c) CID MS-MS of m/z $702.7^{3+}$ from PML peptide with SUMOylated K490 residue. This figure shows that PML is SUMOylated by SUMO1 at K490. This peptide could not be identified by MS/MS with NTA only (a) compared to dual affinity enrichment (b). The MS/MS shown in (c) validate the assignment.

Figure 25:
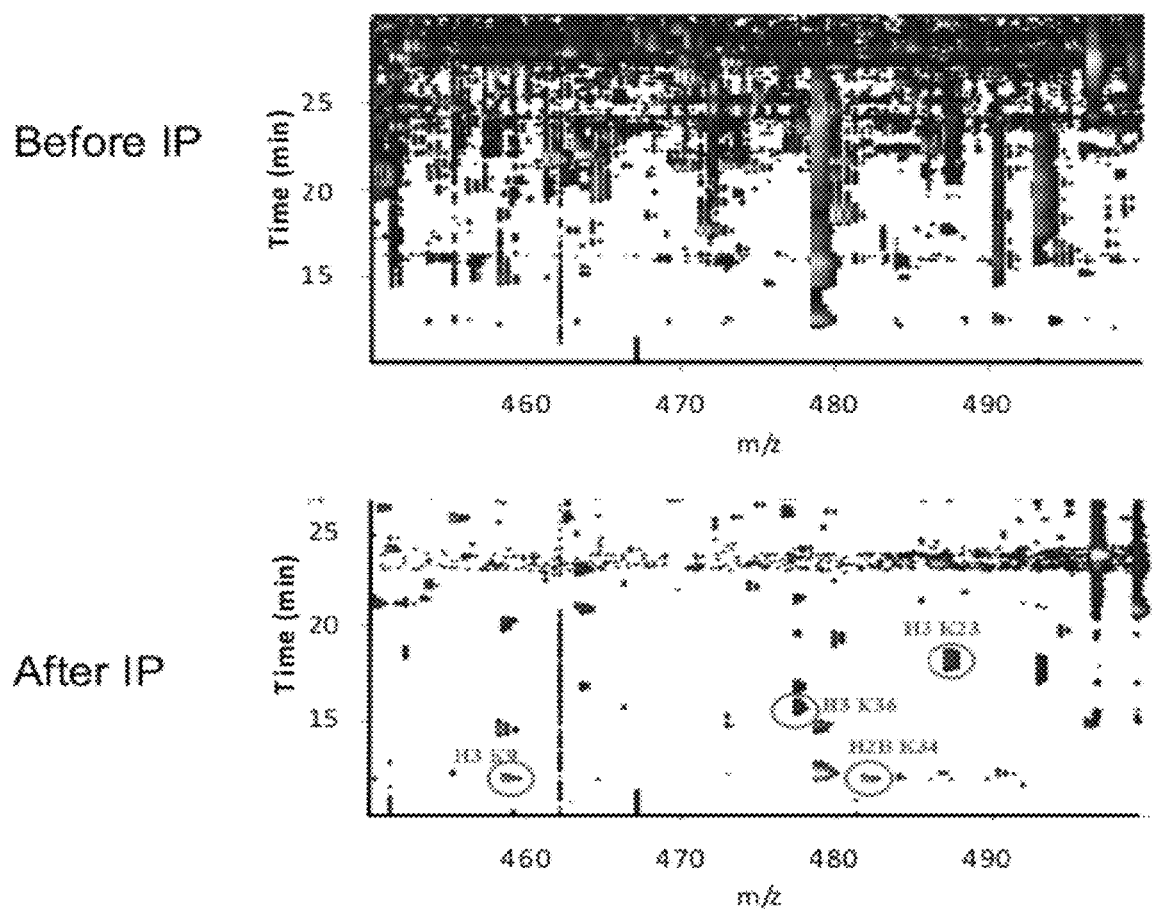
FIG. 25 illustrates in vitro SUMOylation of purified human histones with His-SUMO1 mutant. LC-MS analysis of in vitro SUMOylation reaction before (top) and after (bottom) immunoaffinity purification (IP) with anti SUMO1 mutant antibody (targeting the GGTQE tag (SEQ ID NO: 32)). Clear enrichment of SUMOylated peptides is evidenced after immunoaffinity isolation. Identification of the corresponding SUMOylation site was achieved using LC-MS/MS from the same analysis.

FIG. 25 illustrates the in vitro SUMOylation of purified human histones with His-SUMO1 mutant. LC-MS analysis of in vitro SUMOylation reaction before (top) and after (bottom) immunoaffinity isolation with anti SUMO1 mutant antibody (targeting the GGTQE tag (SEQ ID NO: 32)). Clear enrichment of SUMOylated peptides is evidenced after immunoaffinity isolation. Identification of the corresponding SUMOylation site was achieved using LC-MS/MS from the same analysis. This figure demonstrates that low abundance SUMO peptides can be identified from in vitro experiments. IN this case several histone sites were confirmed to be modified by SUMO1 using MS/MS. One of these sites corresponding to lysine 23 on histone H3 (H3K23) was also detected from in vivo HEK293 SUMO mutant (Table of FIG. 23).

FIG. 26 summarizes the results from the in vitro SUMOylation of histones where sites are shown for each histone.

It is understood that the examples and embodiments described herein are for illustrative purposes only and that various modifications or changes in light thereof will be suggested to persons skilled in the art and are to be included within the present discovery and scope of the appended claims.

We claim:

1. An antibody that binds to (i) the peptide EQTGG of SEQ ID NO: 34, QQTGG of SEQ ID NO: 36, and/or NQTGG of SEQ ID NO: 37, covalently linked to the lysine residue at position 3 from the SUMOylated protein substrate fragment EFKEVLK of SEQ ID NO:38 from Ubiquitin Conjugating Enzyme E2-25K (E2-25K) and (ii) the peptide EQTGG of SEQ ID NO: 34, QQTGG of SEQ ID NO: 36, and/or NQTGG of SEQ ID NO: 37, covalently linked to the lysine residue from the fragment FKVELC of SEQ ID NO:39.

2. The antibody of claim 1 wherein the antibody is a monoclonal antibody or a polyclonal antibody.

3. A kit comprising the antibody of claim 1; and optionally a means for detecting the antibody bound to the mutated SUMOylated protein substrate fragment.

4. The kit of claim 3 wherein the antibody is a monoclonal antibody or a polyclonal antibody.

5. The antibody of claim 2 wherein the antibody is a monoclonal antibody.

6. The antibody of claim 1 wherein the antibody specifically binds to (i) the peptide EQTGG of SEQ ID NO: 34 covalently linked to the lysine residue at position 3 from the SUMOylated protein substrate fragment EFKEVLK of SEQ ID NO: 38 from E2-25K and (ii) the peptide EQTGG of SEQ ID NO: 34 covalently linked to the lysine residue from the fragment FKVELC of SEQ ID NO: 39.

7. The antibody of claim 1 wherein the antibody specifically binds to (i) the peptide QQTGG of SEQ ID NO: 36 covalently linked to the lysine residue at position 3 from the SUMOylated protein substrate fragment EFKEVLK of SEQ ID NO: 38 from E2-25K and (ii) the peptide EQTGG of SEQ ID NO: 34 covalently linked to the lysine residue from the fragment FKVELC of SEQ ID NO: 39.

8. The antibody of claim 1 wherein the antibody specifically binds to (i) the peptide NQTGG of SEQ ID NO: 37 covalently linked to the lysine residue at position 3 from the SUMOylated protein substrate fragment EFKEVLK of SEQ ID NO: 38 from E2-25K and (ii) the peptide EQTGG of SEQ ID NO: 34 covalently linked to the lysine residue from the fragment FKVELC of SEQ ID NO: 39.

9. The antibody of claim 1 wherein the antibody specifically binds to (i) the peptide EQTGG of SEQ ID NO: 34, the peptide QQTGG of SEQ ID NO: 36 and the peptide NQTGG of SEQ ID NO: 37 covalently linked to the lysine residue at position 3 from the SUMOylated protein substrate fragment EFKEVLK of SEQ ID NO: 38 from E2-25K and (ii) the peptide EQTGG of SEQ ID NO: 34 covalently linked to the lysine residue from the fragment FKVELC of SEQ ID NO: 39.

10. The antibody of claim 1 wherein the antibody is present in a composition that further comprises a trypsinized protein extract.

11. The antibody of claim 1 wherein the antibody is bound to a solid support.

12. The antibody of claim 11 wherein the solid support is a bead.

13. A method for identifying a SUMOylated protein substrate, the method comprising:
(i) culturing a cell expressing a mutated SUMO-1, mutated SUMO-2 and/or mutated SUMO-3 polypeptide under conditions suitable to allow the formation of a mutated SUMOylated protein substrate, wherein said mutated SUMO-1 polypeptide comprises a Q to R substitution at a position corresponding to residue 92 of native human SUMO-1, said mutated SUMO-2 polypeptide comprises a Q to R substitution at a position corresponding to residue 88 of native human SUMO-2, and said mutated SUMO-3 polypeptide comprises a Q to R substitution and a Q to N substitution at positions corresponding to residues 87 and 88, respectively, of native human SUMO-3;

(ii) obtaining an extract comprising the mutated SUMOylated protein substrate from said cell;

(iii) performing a proteolytic digestion using trypsin on said extract to release a fragment of the mutated SUMOylated protein substrate;

(iv) purifying the fragment using any one of the antibody of claim 1;

(v) identifying the purified fragment; and (vi) identifying the SUMOylated protein substrate based on the fragment identified in (v).

14. The method of claim 13 wherein step (v) comprises performing Liquid chromatography-mass spectrometry (LC-MS).

15. The method of claim 13 wherein step (v) comprises performing tandem mass spectrometry.

16. The method of claim 13 wherein said method further comprises enriching the mutated SUMOylated protein substrate prior to step (iii).

17. The method of claim 16 wherein said mutated SUMO-1, mutated SUMO-2 and/or mutated SUMO-3 polypeptide further comprises an affinity tag, and wherein said enriching comprises an affinity chromatography.

18. The method of claim 17 wherein said affinity tag is a polyhistidine tag, and wherein said enriching comprises an immobilized metal affinity chromatography.

\* \* \* \* \*

SEQUENCE LISTING

```
<160> NUMBER OF SEQ ID NOS: 39

<210> SEQ ID NO 1
<211> LENGTH: 327
<212> TYPE: DNA
<213> ORGANISM: Homo sapiens
<220> FEATURE:
<221> NAME/KEY: CDS
<222> LOCATION: (1)..(324)

<400> SEQUENCE: 1 atg gct cat cat cat cat cat cat ggt gga tcc atg tct gac cag gag      48
Met Ala His His His His His His Gly Gly Ser Met Ser Asp Gln Glu
1               5                   10                  15 gcc aaa cct tca act gag gac ttg ggg gat aag aag gaa ggt gaa tat      96
Ala Lys Pro Ser Thr Glu Asp Leu Gly Asp Lys Lys Glu Gly Glu Tyr
```

| | | | | | | | | | | | | | | | | |
|---|---|---|---|---|---|---|---|---|---|---|---|---|---|---|---|---|
| | | | 20 | | | | | 25 | | | | | 30 | | | |
| att | aaa | ctc | aaa | gtc | att | gga | cag | gat | agc | agt | gag | att | cac | ttc | aaa | 144 |
| Ile | Lys | Leu | Lys | Val | Ile | Gly | Gln | Asp | Ser | Ser | Glu | Ile | His | Phe | Lys | |
| | | 35 | | | | | 40 | | | | | 45 | | | | |
| gtg | aaa | atg | aca | aca | cat | ctc | aag | aaa | ctc | aaa | gaa | tca | tac | tgt | caa | 192 |
| Val | Lys | Met | Thr | Thr | His | Leu | Lys | Lys | Leu | Lys | Glu | Ser | Tyr | Cys | Gln | |
| 50 | | | | | 55 | | | | | 60 | | | | | | |
| aga | cag | ggt | gtt | cca | atg | aat | tca | ctc | agg | ttt | ctc | ttt | gag | ggt | cag | 240 |
| Arg | Gln | Gly | Val | Pro | Met | Asn | Ser | Leu | Arg | Phe | Leu | Phe | Glu | Gly | Gln | |
| 65 | | | | | 70 | | | | | 75 | | | | | 80 | |
| aga | att | gct | gat | aat | cat | act | cca | aaa | gaa | ctg | gga | atg | gag | gaa | gaa | 288 |
| Arg | Ile | Ala | Asp | Asn | His | Thr | Pro | Lys | Glu | Leu | Gly | Met | Glu | Glu | Glu | |
| | | | | 85 | | | | | 90 | | | | | 95 | | |
| gat | gtg | att | gaa | gtt | tat | cag | gaa | caa | acg | ggg | ggt | taa | | | | 327 |
| Asp | Val | Ile | Glu | Val | Tyr | Gln | Glu | Gln | Thr | Gly | Gly | | | | | |
| | | | 100 | | | | | 105 | | | | | | | | |

<210> SEQ ID NO 2
<211> LENGTH: 108
<212> TYPE: PRT
<213> ORGANISM: Homo sapiens

<400> SEQUENCE: 2

Met Ala His His His His His His Gly Gly Ser Met Ser Asp Gln Glu
1               5                   10                  15

Ala Lys Pro Ser Thr Glu Asp Leu Gly Asp Lys Lys Glu Gly Glu Tyr
                20                  25                  30

Ile Lys Leu Lys Val Ile Gly Gln Asp Ser Ser Glu Ile His Phe Lys
            35                  40                  45

Val Lys Met Thr Thr His Leu Lys Lys Leu Lys Glu Ser Tyr Cys Gln
        50                  55                  60

Arg Gln Gly Val Pro Met Asn Ser Leu Arg Phe Leu Phe Glu Gly Gln
65                  70                  75                  80

Arg Ile Ala Asp Asn His Thr Pro Lys Glu Leu Gly Met Glu Glu Glu
                85                  90                  95

Asp Val Ile Glu Val Tyr Gln Glu Gln Thr Gly Gly
            100                 105

<210> SEQ ID NO 3
<211> LENGTH: 327
<212> TYPE: DNA
<213> ORGANISM: Homo sapiens
<220> FEATURE:
<221> NAME/KEY: CDS
<222> LOCATION: (1)..(324)

<400> SEQUENCE: 3

| | | | | | | | | | | | | | | | | |
|---|---|---|---|---|---|---|---|---|---|---|---|---|---|---|---|---|
| atg | gct | cat | cat | cat | cat | cat | cat | ggt | gga | tcc | atg | tct | gac | cag | gag | 48 |
| Met | Ala | His | His | His | His | His | His | Gly | Gly | Ser | Met | Ser | Asp | Gln | Glu | |
| 1 | | | | 5 | | | | | 10 | | | | | 15 | | |
| gcc | aaa | cct | tca | act | gag | gac | ttg | ggg | gat | aag | aag | gaa | ggt | gaa | tat | 96 |
| Ala | Lys | Pro | Ser | Thr | Glu | Asp | Leu | Gly | Asp | Lys | Lys | Glu | Gly | Glu | Tyr | |
| | | | 20 | | | | | 25 | | | | | 30 | | | |
| att | aaa | ctc | aaa | gtc | att | gga | cag | gat | agc | agt | gag | att | cac | ttc | aaa | 144 |
| Ile | Lys | Leu | Lys | Val | Ile | Gly | Gln | Asp | Ser | Ser | Glu | Ile | His | Phe | Lys | |
| | | 35 | | | | | 40 | | | | | 45 | | | | |
| gtg | aaa | atg | aca | aca | cat | ctc | aag | aaa | ctc | aaa | gaa | tca | tac | tgt | caa | 192 |
| Val | Lys | Met | Thr | Thr | His | Leu | Lys | Lys | Leu | Lys | Glu | Ser | Tyr | Cys | Gln | |
| 50 | | | | | 55 | | | | | 60 | | | | | | |
| aga | cag | ggt | gtt | cca | atg | aat | tca | ctc | agg | ttt | ctc | ttt | gag | ggt | cag | 240 |
| Arg | Gln | Gly | Val | Pro | Met | Asn | Ser | Leu | Arg | Phe | Leu | Phe | Glu | Gly | Gln | |

```
Arg Gln Gly Val Pro Met Asn Ser Leu Arg Phe Leu Phe Glu Gly Gln
65                  70                  75                  80 aga att gct gat aat cat act cca aaa gaa ctg gga atg gag gaa gaa    288
Arg Ile Ala Asp Asn His Thr Pro Lys Glu Leu Gly Met Glu Glu Glu
                85                  90                  95 gat gtg att gaa gtt tat cgg gaa caa acg ggg ggt taa                327
Asp Val Ile Glu Val Tyr Arg Glu Gln Thr Gly Gly
            100                 105

<210> SEQ ID NO 4
<211> LENGTH: 108
<212> TYPE: PRT
<213> ORGANISM: Homo sapiens

<400> SEQUENCE: 4

Met Ala His His His His His His Gly Gly Ser Met Ser Asp Gln Glu
1               5                   10                  15

Ala Lys Pro Ser Thr Glu Asp Leu Gly Asp Lys Lys Glu Gly Glu Tyr
                20                  25                  30

Ile Lys Leu Lys Val Ile Gly Gln Asp Ser Ser Glu Ile His Phe Lys
            35                  40                  45

Val Lys Met Thr Thr His Leu Lys Lys Leu Lys Glu Ser Tyr Cys Gln
50                  55                  60

Arg Gln Gly Val Pro Met Asn Ser Leu Arg Phe Leu Phe Glu Gly Gln
65                  70                  75                  80

Arg Ile Ala Asp Asn His Thr Pro Lys Glu Leu Gly Met Glu Glu Glu
                85                  90                  95

Asp Val Ile Glu Val Tyr Arg Glu Gln Thr Gly Gly
            100                 105

<210> SEQ ID NO 5
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 5 atg gct cat cat cat cat cat cat ggt gga tcc atg gcc gac gaa aag    48
Met Ala His His His His His His Gly Gly Ser Met Ala Asp Glu Lys
1               5                   10                  15 ccc aag gaa gga gtc aag act gag aac aac gat cat att aat ttg aag    96
Pro Lys Glu Gly Val Lys Thr Glu Asn Asn Asp His Ile Asn Leu Lys
                20                  25                  30 gtg gcg ggg cag gat ggt tct gtg gtg cag ttt aag att aag agg cat    144
Val Ala Gly Gln Asp Gly Ser Val Val Gln Phe Lys Ile Lys Arg His
            35                  40                  45 aca cca ctt agt aaa cta atg aaa gcc tat tgt gaa cga cag gga ttg    192
Thr Pro Leu Ser Lys Leu Met Lys Ala Tyr Cys Glu Arg Gln Gly Leu
50                  55                  60 tca atg agg cag atc aga ttc cga ttt gac ggg caa cca atc aat gaa    240
Ser Met Arg Gln Ile Arg Phe Arg Phe Asp Gly Gln Pro Ile Asn Glu
65                  70                  75                  80 aca gac aca cct gca cag ttg gaa atg gag gat gaa gat aca att gat    288
Thr Asp Thr Pro Ala Gln Leu Glu Met Glu Asp Glu Asp Thr Ile Asp
                85                  90                  95 gtg ttc caa cag cag acg gga ggt                                    312
Val Phe Gln Gln Gln Thr Gly Gly
            100
```

<210> SEQ ID NO 6
<211> LENGTH: 104
<212> TYPE: PRT
<213> ORGANISM: Homo sapiens

<400> SEQUENCE: 6

```
Met Ala His His His His His His Gly Gly Ser Met Ala Asp Glu Lys
1               5                   10                  15

Pro Lys Glu Gly Val Lys Thr Glu Asn Asn Asp His Ile Asn Leu Lys
            20                  25                  30

Val Ala Gly Gln Asp Gly Ser Val Val Gln Phe Lys Ile Lys Arg His
        35                  40                  45

Thr Pro Leu Ser Lys Leu Met Lys Ala Tyr Cys Glu Arg Gln Gly Leu
    50                  55                  60

Ser Met Arg Gln Ile Arg Phe Arg Phe Asp Gly Gln Pro Ile Asn Glu
65                  70                  75                  80

Thr Asp Thr Pro Ala Gln Leu Glu Met Glu Asp Glu Asp Thr Ile Asp
                85                  90                  95

Val Phe Gln Gln Gln Thr Gly Gly
            100
```

<210> SEQ ID NO 7
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 7

```
atg gct cat cat cat cat cat cat ggt gga tcc atg gcc gac gaa aag       48
Met Ala His His His His His His Gly Gly Ser Met Ala Asp Glu Lys
1               5                   10                  15 ccc aag gaa gga gtc aag act gag aac aac gat cat att aat ttg aag       96
Pro Lys Glu Gly Val Lys Thr Glu Asn Asn Asp His Ile Asn Leu Lys
            20                  25                  30 gtg gcg ggg cag gat ggt tct gtg gtg cag ttt aag att aag agg cat      144
Val Ala Gly Gln Asp Gly Ser Val Val Gln Phe Lys Ile Lys Arg His
        35                  40                  45 aca cca ctt agt aaa cta atg aaa gcc tat tgt gaa cga cag gga ttg      192
Thr Pro Leu Ser Lys Leu Met Lys Ala Tyr Cys Glu Arg Gln Gly Leu
    50                  55                  60 tca atg agg cag atc aga ttc cga ttt gac ggg caa cca atc aat gaa      240
Ser Met Arg Gln Ile Arg Phe Arg Phe Asp Gly Gln Pro Ile Asn Glu
65                  70                  75                  80 aca gac aca cct gca cag ttg gaa atg gag gat gaa gat aca att gat      288
Thr Asp Thr Pro Ala Gln Leu Glu Met Glu Asp Glu Asp Thr Ile Asp
                85                  90                  95 gtg ttc cga cag cag acg gga ggt                                      312
Val Phe Arg Gln Gln Thr Gly Gly
            100
```

<210> SEQ ID NO 8
<211> LENGTH: 104
<212> TYPE: PRT
<213> ORGANISM: Homo sapiens

<400> SEQUENCE: 8

```
Met Ala His His His His His His Gly Gly Ser Met Ala Asp Glu Lys
1               5                   10                  15
```

```
Pro Lys Glu Gly Val Lys Thr Glu Asn Asp His Ile Asn Leu Lys
         20                  25                  30

Val Ala Gly Gln Asp Gly Ser Val Val Gln Phe Lys Ile Lys Arg His
         35                  40                  45

Thr Pro Leu Ser Lys Leu Met Lys Ala Tyr Cys Glu Arg Gln Gly Leu
         50                  55                  60

Ser Met Arg Gln Ile Arg Phe Arg Phe Asp Gly Gln Pro Ile Asn Glu
65                  70                  75                  80

Thr Asp Thr Pro Ala Gln Leu Glu Met Glu Asp Glu Asp Thr Ile Asp
                 85                  90                  95

Val Phe Arg Gln Gln Thr Gly Gly
                100

<210> SEQ ID NO 9
<211> LENGTH: 309
<212> TYPE: DNA
<213> ORGANISM: Homo sapiens
<220> FEATURE:
<221> NAME/KEY: CDS
<222> LOCATION: (1)..(309)

<400> SEQUENCE: 9 atg gct cat cat cat cat cat cat ggt gga tcc atg tcc gag gag aag      48
Met Ala His His His His His His Gly Gly Ser Met Ser Glu Glu Lys
1               5                   10                  15 ccc aag gag ggt gtg aag aca gag aat gac cac atc aac ctg aag gtg      96
Pro Lys Glu Gly Val Lys Thr Glu Asn Asp His Ile Asn Leu Lys Val
            20                  25                  30 gcc ggg cag gac ggc tcc gtg gtg cag ttc aag atc aag agg cac acg     144
Ala Gly Gln Asp Gly Ser Val Val Gln Phe Lys Ile Lys Arg His Thr
        35                  40                  45 ccg ctg agc aag ctg atg aag gcc tac tgc gag agg cag ggc ttg tca     192
Pro Leu Ser Lys Leu Met Lys Ala Tyr Cys Glu Arg Gln Gly Leu Ser
    50                  55                  60 atg agg cag atc aga ttc agg ttc gac ggg cag cca atc aat gaa act     240
Met Arg Gln Ile Arg Phe Arg Phe Asp Gly Gln Pro Ile Asn Glu Thr
65                  70                  75                  80 gac act cca gca cag ctg gag atg gag gac gag gac acc atc gac gtg     288
Asp Thr Pro Ala Gln Leu Glu Met Glu Asp Glu Asp Thr Ile Asp Val
                85                  90                  95 ttc cag cag cag acg gga ggt                                         309
Phe Gln Gln Gln Thr Gly Gly
                100

<210> SEQ ID NO 10
<211> LENGTH: 103
<212> TYPE: PRT
<213> ORGANISM: Homo sapiens

<400> SEQUENCE: 10

Met Ala His His His His His His Gly Gly Ser Met Ser Glu Glu Lys
1               5                   10                  15

Pro Lys Glu Gly Val Lys Thr Glu Asn Asp His Ile Asn Leu Lys Val
            20                  25                  30

Ala Gly Gln Asp Gly Ser Val Val Gln Phe Lys Ile Lys Arg His Thr
        35                  40                  45

Pro Leu Ser Lys Leu Met Lys Ala Tyr Cys Glu Arg Gln Gly Leu Ser
    50                  55                  60

Met Arg Gln Ile Arg Phe Arg Phe Asp Gly Gln Pro Ile Asn Glu Thr
65                  70                  75                  80
```

```
Asp Thr Pro Ala Gln Leu Glu Met Glu Asp Glu Asp Thr Ile Asp Val
                85                  90                  95

Phe Gln Gln Gln Thr Gly Gly
            100

<210> SEQ ID NO 11
<211> LENGTH: 309
<212> TYPE: DNA
<213> ORGANISM: Homo sapiens
<220> FEATURE:
<221> NAME/KEY: CDS
<222> LOCATION: (1)..(309)

<400> SEQUENCE: 11 atg gct cat cat cat cat cat cat ggt gga tcc atg tcc gag gag aag        48
Met Ala His His His His His His Gly Gly Ser Met Ser Glu Glu Lys
1               5                   10                  15 ccc aag gag ggt gtg aag aca gag aat gac cac atc aac ctg aag gtg        96
Pro Lys Glu Gly Val Lys Thr Glu Asn Asp His Ile Asn Leu Lys Val
            20                  25                  30 gcc ggg cag gac ggc tcc gtg gtg cag ttc aag atc aag agg cac acg       144
Ala Gly Gln Asp Gly Ser Val Val Gln Phe Lys Ile Lys Arg His Thr
        35                  40                  45 ccg ctg agc aag ctg atg aag gcc tac tgc gag agg cag ggc ttg tca       192
Pro Leu Ser Lys Leu Met Lys Ala Tyr Cys Glu Arg Gln Gly Leu Ser
    50                  55                  60 atg agg cag atc aga ttc agg ttc gac ggg cag cca atc aat gaa act       240
Met Arg Gln Ile Arg Phe Arg Phe Asp Gly Gln Pro Ile Asn Glu Thr
65                  70                  75                  80 gac act cca gca cag ctg gag atg gag gac gag gac acc atc gac gtg       288
Asp Thr Pro Ala Gln Leu Glu Met Glu Asp Glu Asp Thr Ile Asp Val
                85                  90                  95 ttc cgg aac cag acg gga ggt                                           309
Phe Arg Asn Gln Thr Gly Gly
            100

<210> SEQ ID NO 12
<211> LENGTH: 103
<212> TYPE: PRT
<213> ORGANISM: Homo sapiens

<400> SEQUENCE: 12

Met Ala His His His His His His Gly Gly Ser Met Ser Glu Glu Lys
1               5                   10                  15

Pro Lys Glu Gly Val Lys Thr Glu Asn Asp His Ile Asn Leu Lys Val
            20                  25                  30

Ala Gly Gln Asp Gly Ser Val Val Gln Phe Lys Ile Lys Arg His Thr
        35                  40                  45

Pro Leu Ser Lys Leu Met Lys Ala Tyr Cys Glu Arg Gln Gly Leu Ser
    50                  55                  60

Met Arg Gln Ile Arg Phe Arg Phe Asp Gly Gln Pro Ile Asn Glu Thr
65                  70                  75                  80

Asp Thr Pro Ala Gln Leu Glu Met Glu Asp Glu Asp Thr Ile Asp Val
                85                  90                  95

Phe Arg Asn Gln Thr Gly Gly
            100

<210> SEQ ID NO 13
<211> LENGTH: 95
<212> TYPE: PRT
```

<213> ORGANISM: Homo sapiens

<400> SEQUENCE: 13

```
Met Ala Asn Glu Lys Pro Thr Glu Glu Val Lys Thr Glu Asn Asn Asn
1               5                   10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
        35                  40                  45

Glu Pro Arg Gly Leu Ser Val Lys Gln Ile Arg Phe Arg Phe Gly Gly
    50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                85                  90                  95
```

<210> SEQ ID NO 14
<211> LENGTH: 576
<212> TYPE: DNA
<213> ORGANISM: Homo sapiens
<220> FEATURE:
<221> NAME/KEY: CDS
<222> LOCATION: (1)..(285)
<220> FEATURE:
<221> NAME/KEY: CDS
<222> LOCATION: (289)..(573)

<400> SEQUENCE: 14

```
atg gcc aac gaa aag ccc aca gaa gaa gtc aag act gag aac aac aat      48
Met Ala Asn Glu Lys Pro Thr Glu Glu Val Lys Thr Glu Asn Asn Asn
1               5                   10                  15 cat att aat ttg aag gtg gcg gga cag gat ggt tct gtg gtg cag ttt      96
His Ile Asn Leu Lys Val Ala Gly Gln Asp Gly Ser Val Val Gln Phe
            20                  25                  30 aag att aag agg cag aca cca ctt agt aaa cta atg aaa gcc tat tgt     144
Lys Ile Lys Arg Gln Thr Pro Leu Ser Lys Leu Met Lys Ala Tyr Cys
        35                  40                  45 gaa cca cgg gga ttg tca gtg aag cag atc aga ttc cga ttt ggt ggg     192
Glu Pro Arg Gly Leu Ser Val Lys Gln Ile Arg Phe Arg Phe Gly Gly
    50                  55                  60 caa cca atc agt gga aca gac aaa cct gca cag ttg gaa atg gaa gat     240
Gln Pro Ile Ser Gly Thr Asp Lys Pro Ala Gln Leu Glu Met Glu Asp
65                  70                  75                  80 gaa gat aca att gat gtg ttt caa cag cct acg gga ggt gtc tac tga     288
Glu Asp Thr Ile Asp Val Phe Gln Gln Pro Thr Gly Gly Val Tyr
                85                  90                  95 atg gcc aac gaa aag ccc aca gaa gaa gtc aag act gag aac aac aat     336
Met Ala Asn Glu Lys Pro Thr Glu Glu Val Lys Thr Glu Asn Asn Asn
                100                 105                 110 cat att aat ttg aag gtg gcg gga cag gat ggt tct gtg gtg cag ttt     384
His Ile Asn Leu Lys Val Ala Gly Gln Asp Gly Ser Val Val Gln Phe
            115                 120                 125 aag att aag agg cag aca cca ctt agt aaa cta atg aaa gcc tat tgt     432
Lys Ile Lys Arg Gln Thr Pro Leu Ser Lys Leu Met Lys Ala Tyr Cys
        130                 135                 140 gaa cca cgg gga ttg tca gtg aag cag atc aga ttc cga ttt ggt ggg     480
Glu Pro Arg Gly Leu Ser Val Lys Gln Ile Arg Phe Arg Phe Gly Gly
    145                 150                 155 caa cca atc agt gga aca gac aaa cct gca cag ttg gaa atg gaa gat     528
Gln Pro Ile Ser Gly Thr Asp Lys Pro Ala Gln Leu Glu Met Glu Asp
160                 165                 170                 175
```

```
gaa gat aca att gat gtg ttt caa cag cct acg gga ggt gtc tac tga      576
Glu Asp Thr Ile Asp Val Phe Gln Gln Pro Thr Gly Gly Val Tyr
            180                 185                 190
```

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacccaagct tggtaccatg gctcatc                                         27

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctaccgctcg agttaacccc ccgtttgttc ctgataaact tc                        42

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctaccgctcg agttaacccc ccgtttgttc ccgataaact tc                        42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctaccgctcg agttaacctc ccgtctgctg ttggaacaca tc                        42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctaccgctcg agttaacctc ccgtctgctg tcggaacaca tc                        42

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctaccgctcg agttaacctc ccgtctgctg ctggaacacg tc                    42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctaccgctcg agttaacctc ccgtctggtt ccggaacacg tc                    42

<210> SEQ ID NO 22
<211> LENGTH: 42
<212> TYPE: PRT
<213> ORGANISM: Homo sapiens

<400> SEQUENCE: 22

Gly Ile Pro Pro Asp Gln Gln Arg Leu Ile Phe Ala Gly Lys Gln Leu
1               5                   10                  15

Glu Asp Gly Arg Thr Leu Ser Asp Tyr Asn Ile Gln Lys Glu Ser Thr
            20                  25                  30

Leu His Leu Val Leu Arg Leu Arg Gly Gly
        35                  40

<210> SEQ ID NO 23
<211> LENGTH: 42
<212> TYPE: PRT
<213> ORGANISM: Homo sapiens

<400> SEQUENCE: 23

Gly Val Pro Met Asn Ser Leu Arg Phe Leu Phe Glu Gly Gln Arg Ile
1               5                   10                  15

Ala Asp Asn His Thr Pro Lys Glu Leu Gly Met Glu Glu Glu Asp Val
            20                  25                  30

Ile Glu Val Tyr Gln Glu Gln Thr Gly Gly
        35                  40

<210> SEQ ID NO 24
<211> LENGTH: 42
<212> TYPE: PRT
<213> ORGANISM: Homo sapiens

<400> SEQUENCE: 24

Gly Leu Ser Met Arg Gln Ile Arg Phe Arg Phe Asp Gly Gln Pro Ile
1               5                   10                  15

Asn Glu Thr Asp Thr Pro Ala Gln Leu Glu Met Glu Asp Glu Asp Thr
            20                  25                  30

Ile Asp Val Phe Gln Gln Gln Thr Gly Gly
        35                  40

<210> SEQ ID NO 25
<211> LENGTH: 42
<212> TYPE: PRT
<213> ORGANISM: Homo sapiens

<400> SEQUENCE: 25

Gly Leu Ser Met Arg Gln Ile Arg Phe Arg Phe Asp Gly Gln Pro Ile
1               5                   10                  15

```
Asn Glu Thr Asp Thr Pro Ala Gln Leu Glu Met Glu Asp Glu Asp Thr
             20                  25                  30

Ile Asp Val Phe Gln Gln Gln Thr Gly Gly
        35                  40

<210> SEQ ID NO 26
<211> LENGTH: 10
<212> TYPE: PRT
<213> ORGANISM: Homo sapiens

<400> SEQUENCE: 26

Ile Glu Val Tyr Arg Glu Gln Thr Gly Gly
1               5                   10

<210> SEQ ID NO 27
<211> LENGTH: 10
<212> TYPE: PRT
<213> ORGANISM: Homo sapiens

<400> SEQUENCE: 27

Ile Glu Val Tyr Gln Arg Gln Thr Gly Gly
1               5                   10

<210> SEQ ID NO 28
<211> LENGTH: 10
<212> TYPE: PRT
<213> ORGANISM: Homo sapiens

<400> SEQUENCE: 28

Ile Glu Val Tyr Gln Glu Arg Thr Gly Gly
1               5                   10

<210> SEQ ID NO 29
<211> LENGTH: 10
<212> TYPE: PRT
<213> ORGANISM: Homo sapiens

<400> SEQUENCE: 29

Ile Asp Val Phe Arg Gln Gln Thr Gly Gly
1               5                   10

<210> SEQ ID NO 30
<211> LENGTH: 10
<212> TYPE: PRT
<213> ORGANISM: Homo sapiens

<400> SEQUENCE: 30

Ile Asp Val Phe Arg Asn Gln Thr Gly Gly
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis

<400> SEQUENCE: 31

His His His His His His
1               5

<210> SEQ ID NO 32
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Gly Gly Thr Gln Glu
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Gln Thr Gly
1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Gln Thr Gly Gly
1               5

<210> SEQ ID NO 35
<211> LENGTH: 95
<212> TYPE: PRT
<213> ORGANISM: Homo sapiens

<400> SEQUENCE: 35

Met Ala Asn Glu Lys Pro Thr Glu Glu Val Lys Thr Glu Asn Asn Asn
1               5                   10                  15

His Ile Asn Leu Lys Val Ala Gly Gln Asp Gly Ser Val Val Gln Phe
            20                  25                  30

Lys Ile Lys Arg Gln Thr Pro Leu Ser Lys Leu Met Lys Ala Tyr Cys
        35                  40                  45

Glu Pro Arg Gly Leu Ser Val Lys Gln Ile Arg Phe Arg Phe Gly Gly
    50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                85                  90                  95

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Thr Gly Gly
1               5
```

```
<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Gln Thr Gly Gly
1               5

<210> SEQ ID NO 38
<211> LENGTH: 7
<212> TYPE: PRT
<213> ORGANISM: Homo sapiens

<400> SEQUENCE: 38

Glu Phe Lys Glu Val Leu Lys
1               5

<210> SEQ ID NO 39
<211> LENGTH: 6
<212> TYPE: PRT
<213> ORGANISM: Homo sapiens

<400> SEQUENCE: 39

Phe Lys Val Glu Leu Cys
1               5
```